United States Patent [19]

Corbett

[11] Patent Number: 4,473,578

[45] Date of Patent: Sep. 25, 1984

[54] β-LACTAM ANTIBIOTICS AND THEIR USE

[75] Inventor: David F. Corbett, Dorking, England

[73] Assignee: Beecham Group Limited, England

[21] Appl. No.: 403,076

[22] Filed: Jul. 29, 1982

Related U.S. Application Data

[62] Division of Ser. No. 177,272, Aug. 11, 1980.

[30] Foreign Application Priority Data

Aug. 10, 1979 [GB] United Kingdom ............... 7927901
Apr. 17, 1980 [GB] United Kingdom ............... 8012724

[51] Int. Cl.³ .................. A61K 31/395; C07D/487/04
[52] U.S. Cl. .......................... 424/274; 260/245.2 T;
260/245.2 R
[58] Field of Search ............ 260/245.2 T, 245.2 R;
424/274, 270

[56] References Cited

U.S. PATENT DOCUMENTS 4,203,902  5/1980  Shih ........................ 260/245.2 T
4,347,367  8/1982  Christensen et al. ......... 260/245.2 T
4,347,368  8/1982  Christensen et al. ......... 260/245.2 T Primary Examiner—Nicholas S. Rizzo
Attorney, Agent, or Firm—Jacobs & Jacobs

[57] ABSTRACT

The compounds of the formula:

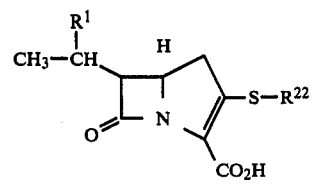

and pharmaceutically acceptable salts and in-vivo hydrolysable esters thereof wherein $R^1$ is a hydrogen atom or a group selected from OH, $OSO_3H$ or a pharmaceutically acceptable salt or $C_{1-4}$ alkyl ester thereof, $OR^2$, $SR^3$, $OCOR^2$, $OCO_2R^3$ or $OCONHR^3$, where $R^2$ is a $C_{1-6}$ alkyl group or an optionally substituted benzyl group and $R^3$ is a $C_{1-6}$ alkyl group or an optionally substituted benzyl or an optionally substituted phenyl group; and $R^{22}$ is a hydrogen atom, $C_{1-6}$ alkyl, $C_{2-6}$ alkenyl, $C_{3-6}$ alkynyl wherein the triple bond is not present on the carbon adjacent to the sulphur atom, aralkyl, $C_{1-6}$ alkanoyl, aralkanoyl, aryloxyalkanoyl or arylcarbonyl, any of such $R^{22}$ groups being optionally substituted; with the proviso that when $R^{22}$ is 2-aminoethyl $R^1$ must be $SR^3$ or $OSO_3H$ or a pharmaceutically acceptable salt of $C_{1-4}$ alkyl ester thereof; have been found to be antibacterially active. Their use is described as are processes for their preparation.

49 Claims, No Drawings

β-LACTAM ANTIBIOTICS AND THEIR USE

CROSS-REFERENCE

This is a division of Ser. No. 177,272 filed Aug. 11, 1980.

This invention relates to novel antibacterial carbapenem derivatives, to processes for their preparation and to compositions containing them.

European Patent Application Publication No. 1628 discloses a group of synthetic antibacterial agents containing a 7-oxo-1-azabicyclo[3.2.0.]hept-2-ene ring system. However all compounds described in that specification were racemic at C-5 and could only be prepared by a very long synthetic sequence. A new process has been discovered that enables new antibacterial agents to be prepared via the intermediacy of a thiol. These new antibacterial agents can be prepared by a relatively short reaction sequence from natural products and are produced as a desirable single optical isomer at C-5.

The present invention provides the compounds of the formula (I):

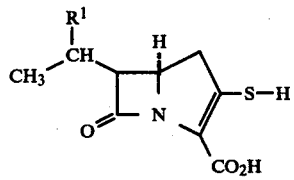

and salts and esters thereof wherein $R^1$ is a hydrogen atom or a group selected from OH, $OSO_3H$ or a salt or $C_{1-4}$ alkyl ester thereof, $OR^2$, $SR^3$, $OCOR^2$, $OCO_2R^3$ or $OCONHR^3$, where $R^2$ is a $C_{1-6}$ alkyl group or an optionally substituted benzyl group and $R^3$ is a $C_{1-6}$ alkyl group or an optionally substituted benzyl or an optionally substituted phenyl group: with the proviso that when $R^1$ is $OSO_3H$ or a salt or $C_{1-4}$ alkyl ester thereof the C-6 and C-5 hydrogen atoms are cis.

A group of compounds of interest are those of the formula (I) wherein $R^1$ is a hydrogen atom or a group selected from OH, $OSO_3H$ or a pharmaceutically acceptable salt or a methyl or ethyl ester thereof, $OR^2$, $SR^3$, $OCOR^2$, $OCO_2R^3$ or $OCONHR^3$ where $R^2$ is a $C_{1-4}$ alkyl group or a benzyl group and $R^3$ is a $C_{1-4}$ alkyl group or a benzyl, phenyl or p-nitrobenzyl group.

When used herein the term "optionally substituted benzyl" means that the phenyl ring of the benzyl group can be substituted by hydrogen, $C_{1-3}$ alkoxy, fluorine, bromine, chlorine or nitro. The term "optionally substituted phenyl" means that the phenyl group can be substituted by hydrogen, $C_{1-3}$ alkyl, $C_{1-3}$ alkoxy, fluorine, bromine, chlorine or nitro.

Suitable values for $R^1$ include hydrogen, hydroxy, $OSO_3H$ or a salt or methyl or ethyl ester thereof, methylthio, ethylthio, phenylthio, benzylthio, p-nitrobenzylthio, acetoxy, propionoxy, benzyloxy and phenylacetyloxy.

Preferred values for $R^1$ include hydrogen, hydroxy, acetoxy and $OSO_3H$ or salt or methyl or ethyl ester thereof.

Although compounds of the formula (I) and salts and esters thereof have antibacterial activity, they are primarily envisaged as starting-materials in the processes hereinafter defined.

Suitably for use as an intermediate in such processes any sulphate moiety in the group $R^1$ in the compounds of the formula (I) is in the form of a quaternary ammonium salt for example the benzyldimethyl-n-hexadecylammonium salt, or is in the form of a methyl or ethyl sulphate ester.

Suitably for use as an intermediate the compound of the formula (I) is in the form of a cleavable ester at the C-2 carboxyl. Apt cleavable esters include those cleavable by chemical methods such as hydrogenolysis or hydrolysis or by biological methods.

Suitably the carboxylic acid is esterified by a group of the sub-formula (a), (b), (c) or (d):

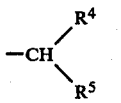 (a)

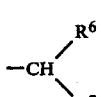 (b)

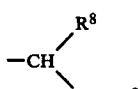 (c)

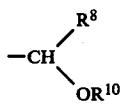 (d)

wherein $R^4$ is a hydrogen atom or an alkyl, alkenyl or alkynyl group of up to 3 carbon atoms; $R^5$ is a hydrogen atom or a methyl group; $R^6$ is a phenyl group or a phenyl group substituted by a fluorine, chlorine or bromine atom or a nitro, methyl or methoxy group; $R^7$ is a hydrogen atom or a phenyl group or a phenyl group substituted by a fluorine, chlorine or bromine atom or a nitro, methyl or methoxy group; $R^8$ is a hydrogen atom or a methyl group; $R^9$ is a $C_{1-4}$ alkyl, phenyl or $C_{1-4}$ alkoxy group or $R^8$ is joined to $R^9$ to form a phthalidyl, dimethylphthalidyl or dimethoxyphthalidyl group; and $R^{10}$ is a $C_{1-4}$ alkyl, phenyl, chlorophenyl or nitrophenyl group; or $CHR^4R^5$ is a phenacyl or bromophenacyl group.

Favourably $R^4$ is a hydrogen atom or a methyl, ethyl, vinyl or ethanyl group. Favourably $R^5$ is a hydrogen atom. Favourably $R^6$ is a phenyl, p-bromophenyl, p-methoxyphenyl or p-nitrophenyl group. Favourably $R^7$ is a hydrogen atom. Favourably $R^9$ is a methyl, t-butyl or ethoxy group or is joined to $R^8$. Favourably $R^{10}$ is a methyl group.

Preferred groups of the sub-formula (a) include the methyl and ethyl groups.

Preferred groups of the sub-formula (b) include the benzyl and p-nitrobenzyl groups.

Preferred groups of the sub-formula (c) include the acetoxymethyl, pivaloyloxymethyl, α-ethoxycarbonyloxymethyl and phthalidyl groups.

A preferred group of the sub-formula (d) is the methoxymethyl group.

Particularly preferred esterifying groups are the p-nitrobenzyl and phthalidyl groups.

When the compounds of the formula (I) and salts and esters thereof are intended for use as antibacterial agents, then suitably the compound is in the form of an in-vivo hydrolysable ester or pharmaceutically acceptable salt. Suitable in-vivo hydrolysable esters include those of sub-formula (c) as hereinbefore defined. Suitable pharmaceutically acceptable salts include those of the alkali and alkaline earth metals, of these the sodium and potassium salts are preferred. These pharmaceutically acceptable salts may be formed at the C-2 carboxl, and/or at a C-8 sulphate moiety (if present). Thus compounds of the formula (I) wherein $R^1$ is a $OSO_3H$ group or pharmaceutically acceptable salt thereof may be in the form of a di-salt such as the di-sodium salt or di-potassium salt, or may be in the form of a mono-salt of an in-vivo hydrolysable ester, or may be in the form of a mono-salt of an acid or may be in the form of a di-acid.

The compounds of the formula (I) may have the cis- or trans- geometry about the β-lactam, that is to say they have the (5R, 6R) or (5R, 6S) configuration. Alternatively the compounds of the formula (I) may be presented in the form of an cis/trans mixture.

The compounds of the formula (I) may have R or S stereochemistry at C-8 (except of course when $R^1$ is hydrogen) or may be in the form of mixtures thereof. The compounds of the formula (I) wherein $R^1$ is $OSO_3H$ or a salt or $C_{1-4}$ ester thereof are in the 8S-configuration as the necessary intermediates are more readily available.

The present invention also provides a process for the preparation of a compound of the formula (I) or salt or ester thereof which process comprises the reaction of a cleavable ester of a compound of the formula (II):

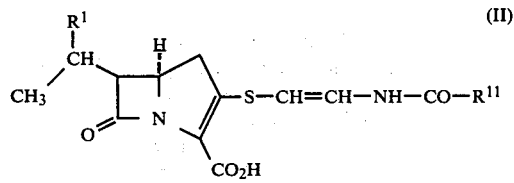

wherein $R^1$ is as defined in relation to formula (I) and $R^{11}$ is a methyl or ethyl group; with a source of hypohalous acid, and optionally thereafter:
(i) converting a cleavable ester to a free acid or salt,
(ii) converting a cleavable ester to a different cleavable ester,
with the proviso that when $R^{11}$ is an ethyl group $R^1$ must be $OSO_3H$ or a salt or $C_{1-4}$ alkyl ester thereof.

Preferably $R^{11}$ is a methyl group as the intermediates are more readily available.

Suitably the reaction is performed at a nonextreme temperature such as $-15°$ C. to $+25°$ C., preferably ambient. Solvents suitable in this reaction are inert organic solvents optionally in the presence of moisture, for example moist acetone or dioxan.

Preferred esters for use in this process are those described hereinbefore as preferred esters for compounds of the formula (I). A particularly preferred ester for use in this process is the p-nitrobenzyl ester.

Suitably the hypohalous acid is hypobromous acid or hypochlorous acid, of these hypobromous acid is preferred. Suitable sources of hypohalous acids include N-bromoacetamide, N-chloroacetamide and N-bromopropionamide.

Compounds of the formula (II) may be prepared by the methods of European Patent Application Publication Nos. 5348, 5349, 7152, 8497, Belgian Pat. No. 864570, U.K. Pat. No. 1489235 and our co-pending U.K. Application No. 8021730.

In a further aspect this invention provides a group of a novel compounds which may be formed from the compounds of the formula (I). Thus the present invention provides the compounds of the formula (III):

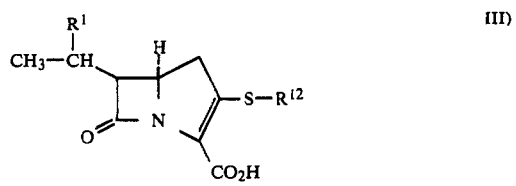

and pharmaceutically acceptable salts and in-vivo hydrolysable esters thereof wherein $R^1$ is as defined in relation to formula (I) except that any sulphate salt must be pharmaceutically acceptable and $R^{12}$ is $C_{1-6}$ alkyl, $C_{2-6}$ alkenyl, $C_{3-6}$ alkynyl wherein the triple bond is not present on the carbon adjacent to the sulphur atom, aralkyl, $C_{1-6}$ alkanoyl, aralkanoyl, aryloxyalkanoyl or arylcarbonyl, any of such $R^{12}$ groups being optionally substituted; with the proviso that when $R^{12}$ is 2-aminoethyl $R^1$ must be $SR^3$ or $OSO_3H$ or a pharmaceutically acceptable salt or $C_{1-4}$ alkyl ester thereof; and with the further proviso that when $R^1$ is $OSO_3H$ or a pharmaceutically acceptable salt or $C_{1-4}$ alkyl ester thereof the C-5 and C-6 hydrogen atoms are cis.

When $R^{12}$ is a $C_{1-6}$ alkyl group suitable substituents include amino, hydroxy, $C_{1-6}$ alkanoyloxy, $C_{1-6}$ alkoxy, benzoyl, $C_{1-6}$ alkanoyl or carboxy or an ester or pharmaceutically acceptable salt thereof.

When $R^{12}$ is a $C_{2-6}$ alkenyl group wherein the double bond is not present on the carbon adjacent to the sulphur atom, suitable substituents include carboxy or an ester or pharmaceutically acceptable salt thereof, or hydroxy or $C_{1-6}$ alkoxy.

When $R^{12}$ is a $C_{2-6}$ alkenyl group wherein the double bond is present on the carbon adjacent to the sulphur atom, suitable substituents are carboxy or an ester or pharmaceutically acceptable salt thereof.

When used herein the term "aralkyl" means a $C_{1-6}$ alkyl group substituted by an aryl group, examples of such aryl groups being naphthyl, pyrrolyl, furyl, thienyl, indolyl, thionaphthyl, benzofuryl, imidazolyl, thiazolyl, or any of such groups substituted by one or more groups selected from $C_{1-3}$ alkyl, phenyl, nitro and amino; or a phenyl group optionally substitued by a halogen atom or a $C_{1-3}$ alkoxy, nitro or acetamido group.

A group of compounds of interest is that of the formula (IV):

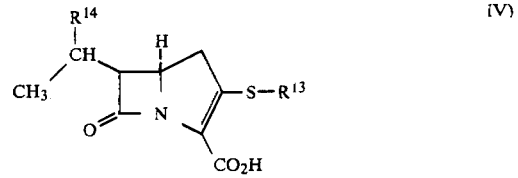

and pharmaceutically acceptable salts and in-vivo hydrolysable esters thereof wherein $R^{14}$ is a hydrogen atom or a group selected from OH, $OSO_3H$ or a pharmaceutically acceptable salt or a methyl or ethyl ester thereof, $OR^2$, $SR^3$, $OCOR_2$, $R^3$ or $OCONHR^3$ where $R^2$ is a $C_{1-4}$ alkyl group or a benzyl group and $R^3$ is a $C_{1-4}$ alkyl group or a benzyl, phenyl or p-nitrobenzyl group; and $R^{13}$ is $C_{1-4}$ alkyl, $C_{1-4}$ alkyl substituted by a phenyl group optionally substituted by a fluorine, chlorine or bromine atom or a methoxy, nitro, amino, acetamido or p-nitrobenzyloxycarbonylamino group; a $C_{2-4}$ alkyl group substituted on other than the α-carbon atom by an amino, p-nitrobenzyloxycarbonyolamino, hydroxy, p-nitrobenzyloxycarbonyloxy, methoxy, acetoxy or $C_{1-4}$ alkyloxycarbonyl group; a $C_{1-4}$ acyl group or a benzoyl, phenylacetyl or phenoxyacetyl group; or a $CH=CHCO_2H$ group or a pharmaceutically acceptable salt or ester thereof. In one aspect of the compounds of the formula (IV), the group $CH=CHCO_2H$ is esterified to form a $C_{1-4}$ alkyl ester or amino $C_{1-4}$ alkyl ester.

A similar group of compounds of interest is that of the formula (V):

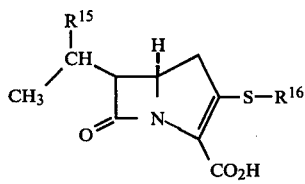

(V)

and pharmaceutically acceptable salts and in-vivo hydrolysable esters thereof wherein either:

$R^{15}$ is hydrogen or hydroxy, and $R^{16}$ is a $C_{1-6}$ alkyl group substituted by amino, benzoyl, $C_{1-6}$ alkanoyl or carboxy or ester or pharmaceutically acceptable salt thereof or $R^{16}$ is a group selected from $C_{2-6}$ alkenyl, $C_{3-6}$ alkynyl wherein the triple bond is not present on the carbon atom adjacent to the sulphur atom, aralkyl, $C_{1-6}$ alkanoyl, aralkanoyl, aryloxyalkanoyl or arylcarbonyl, any of such groups being optionally substituted; or $R^{15}$ is a group selected from $OSO_3H$ or a salt or $C_{1-4}$ alkyl ester thereof, $OR^2$, $SR^3$, $OCOR^2$, $OCO_2R^3$ or $OCONHR^3$ wherein $R^2$ and $R^3$ are as defined in relation to compounds of the formula (I); and $R^{16}$ is a group $R^{12}$ wherein $R^{12}$ is as defined in relation to compounds of the formula (III);

with the proviso that when $R^{16}$ is 2-aminoethyl $R^{15}$ must be $SR^3$ or $OSO_3H$ or a pharmaceutically acceptable salt or $C_{1-4}$ alkyl ester thereof; and with the further proviso that when $R^{15}$ is $OSO_3H$ or a pharmaceutically acceptable salt or $C_{1-4}$ alkyl ester thereof the C-5 and C-6 protons are cis.

Suitably $R^1$ in the compounds of the formula (III) is a hydrogen atom or a group selected from OH, $OSO_3H$ or a pharmaceutically acceptable salt or $C_{1-4}$ alkyl ester thereof, $OR^2$, $SR^3$, $OCOR^2$, $OCO_2R^3$ or $OCONHR^3$, wherein $R^2$ and $R^3$ are as defined in relation to formula (I).

More suitably $R^1$ is hydrogen, hydroxy, $OSO_3H$ or a pharmaceutically acceptable salt thereof, or acetoxy. Of these preferred values are hydroxy and $OSO_3H$ or a pharmaceutically acceptable salt thereof such as the sodium or potassium salt.

When $R^{12}$ is an alkyl group of substituted alkyl group suitably suc; alkyl groups contain up to 4 carbon atoms, for example $R^{12}$ aptly may be methyl, ethyl, propyl, butyl, aminomethyl, aminoethyl, aminopropyl, aminobutyl, hydroxyethyl, hydroxypropyl, hydroxybutyl, methoxymethyl, methoxyethyl, ethoxymethyl, ethoxyethyl, propoxypropyl, methoxypropyl, methoxybutyl, acetoxymethyl, acetoxyethyl, propionoxymethyl, propionoxyethyl, phenacyl, acetylmethyl, acetylethyl, propionylmethyl, propionylethyl, carboxymethyl or pharmaceutically acceptable salt thereof, methoxycarbonylmethyl, ethoxycarbonylmethyl, methoxycarbonylethyl, methoxycarbonylpropyl, methoxycarbonylbutyl, ethoxycarbonylethyl, carboxyethyl or pharmaceutically acceptable salt thereof, carboxypropyl or pharmaceutically acceptable salt thereof, carboxybutyl or pharmaceutically acceptable salt thereof, and structural isomers thereof, of these preferred values include methyl, ethyl, propyl, butyl and 2-aminoethyl.

Further suitable values for $R^{12}$ include propenyl, butenyl and $CH=CH—CO_2H$ or a pharmaceutically acceptable salt or ester thereof, for example the sodium or potassium salt or the methyl, ethyl, propyl, aminoethyl, aminopropyl, benzyl or p-nitrobenzyl ester.

When $R^{12}$ is an aralkyl group more suitably the alkyl moiety is a methylene or ethylene divalent radical. Suitable examples of the aryl moiety are phenyl optionally substituted by one or more substituents selected from a halogen atom or a $C_{1-3}$ alkoxy, nitro or acetamido group; pyrrolyl optionally substituted by a phenyl or $C_{1-3}$ alkyl group; thienyl optionally substituted by a phenyl or $C_{1-3}$ alkyl group; furyl optionally substituted by a phenyl or $C_{1-3}$ alkyl group; imidazolyl optionally substituted by one or more groups selected from phenyl, nitro, amino, $C_{1-3}$ alkyl; and thiazolyl optionally substituted by one or more groups selected from phenyl, nitro, amino and $C_{1-3}$ alkyl.

More suitably $R^{12}$ is a benzyl, bromobenzyl, chlorobenzyl, fluorobenzyl, methoxybenzyl, nitrobenzyl, acetamidobenzyl, thiazolylmethyl, aminothiazolylmethyl, nitrothiazolylmethyl or phenylthiazolylmethyl group.

Suitably also $R^{12}$ is a phenethyl, pyrrolylethyl or optionally substituted imidazolylethyl. In a suitable aspect the imidazolyl ring may be substituted at the C-2 position (that is the carbon atom α to the two nitrogen atoms) by a $C_{1-3}$ alkyl or phenyl group. In another aspect the imidazolyl ring may be further substituted at the C-4 position or the C-5 position by a $C_{1-3}$ alkyl, phenyl, nitro or amino group; preferably such substituents are on the C-4 position and the C-5 position is unsubstituted; alternatively such substituents are on the C-5 position and the C-4 position is unsubstituted.

In a further aspect $R^{12}$ is a $C_{1-6}$ alkanoyl, aralkanoyl, aroxyalkanoyl or aroyl group, for example acetyl, phenylacetyl, phenoxyacetyl or benzoyl. Of these acetyl is preferred.

The groups specified above for the C-3 substituent $R^{12}$ are also, where applicable, suitable groups for $R^{13}$ and $R^{16}$.

The groups specified above for the C-6 substituent $R^1$ are also, where applicable, suitable groups for $R^{14}$ and $R^{15}$.

Thus it is to be realised that preferred compounds of this invention include those of the formula (VI):

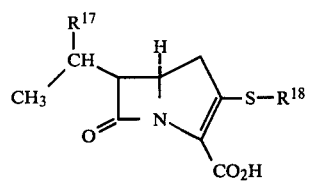

or pharmaceutically acceptable salts or in-vivo hydrolysable esters thereof wherein $R^{17}$ is OH or $OSO_3H$ or a pharmaceutically acceptable salt or $C_{1-4}$ alkyl ester thereof, and $R^{18}$ is an optionally substituted $C_{1-6}$ alkyl group.

A further preferred group of compounds is that of the formula (VII):

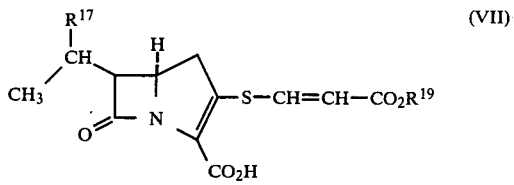

(VII)

or pharmaceutically acceptable salt or cleavable ester thereof wherein $R^{17}$ is as defined in relation to formula (VI) and $R^{19}$ represents a hydrogen atom, a pharmaceutically acceptable salting ion or a $C_{1-4}$ alkyl or amino $C_{1-4}$ alkyl group.

Suitable and preferred in-vivo hydrolysable ester groups for esterifying the C-2 carboxyl of the compounds of the formulae (III)–(VII) are those described in relation to compounds of the formula (I). Suitable pharmaceutically acceptable salts of the compounds of the formulae (III)–(VII) include those of the alkali and alkaline earth metals, of these the sodium and potassium salts are preferred. These pharmaceutically acceptable salts may be formed at the C-2 carboxyl, and/or at a C-8 sulphate moiety (if present). Thus compounds of the formulae (III)–(VII) wherein the C-6 substituent contains a $OSO_3H$ group of pharmaceutically acceptable salt thereof may be in the form of a di-salt such as the di-sodium of di-potassium salt, or may be in the form of a mono-salt of a in-vivo hydrolysable ester, or may be in the form of a mono-salt of an acid or may be in the form of a di-acid.

When the thio side-chain at the C-3 position contains an amino group it is preferred that the compounds of the formulae (III)–(VII) are zwitterionic.

The compounds of the formulae (III)–(VII) may have the cis- or trans- geometry about the β-lactam, that is to say they have the (5R,6R) or (5R, 6S) configuration. Alternatively the compounds of the formulae (III)–(VII) may be presented in the form of a cis/trans mixture.

The compounds of the formulae (III)–(VII) may have R or S stereochemistry at C-8 (except of course when the C-6 substituent is ethyl) or may be in the form of mixtures thereof. The compounds of the formulae (III)–(VII) wherein the C-6 substituent contains a $OSO_3H$ group or pharmaceutically acceptable salt thereof or $C_{1-4}$ alkyl ester thereof are in the 8S-configuration as the necessary intermediates are more readily available.

In a further aspect of this invention there is provided a process for the preparation of a compound of the formula (VIII):

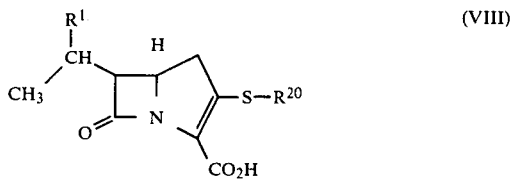

(VIII)

and pharmaceutically acceptable salts and in-vivo hydrolysable esters thereof wherein $R^1$ is as defined in relation to formula (I) except that any sulphate salt must be pharmaceutically acceptable, and $R^{20}$ is $C_{1-6}$ alkyl, $C_{3-6}$ alkenyl wherein the double bond is not present on the carbon atom adjacent to the sulphur atom, $C_{3-6}$ alkynyl wherein the triple bond is not present on the carbon adjacent to the sulphur atom, aralkyl, $C_{1-6}$ alkanoyl, aralkanoyl, aryloxyalkanoyl or arylcarbonyl, any of such $R^{20}$ groups being optionally substituted; with the proviso that when $R^1$ is $OSO_3H$ or a pharmaceutically acceptable salt of $C_{1-4}$ alkyl ester thereof the C-5 and C-6 protons are cis; which process comprises the reaction of a cleavable ester of a compound of the formula (I) with a compound of the formula (IX):

$X-R^{20}$ (IX)

wherein X is a leaving group, in the presence of an acid acceptor; and subsequently:
(i) converting any cleavable ester group which is not in-vivo hydrolysable into a free acid, a pharmaceutically acceptable salt or in-vivo hydrolysable ester group;
(ii) optionally converting any cleavable ester group which is in-vivo hydrolysable into a free acid, a pharmaceutically acceptable salt or a different in-vivo hydrolysable ester group.

Suitable acid acceptors are carbonates and bicarbonates such as anhydrous potassium carbonate. The reaction is generally carried out in a dry polar solvent such as dimethylformamide. Suitably the reaction is preformed at a non-extreme temperature, for example, −30° C. to +60° C., more suitably −10° C. to +40° C. and preferably at ambient temperature.

Suitably X is a chlorine, bromine or iodine atom or is a sulphonate ester moiety such as a tosylate or mesylate, of these values iodine and chlorine are preferred. In an alternative aspect when $R^{20}$ is a methyl or ethyl group, the leaving group X may be dimethyl ether or diethyl ether respectively. In other words X is derived from a trimethyloxonium salt or a triethyloxonium salt. Such salts are conveniently presented as their tetrafluoroborates. Such alkylations involving a trimethyloxonium or triethyloxonium salt are preferably performed in a halogenated hydrocarbon solvent for example dichloromethane or chloroform, at a depressed temperature for example −80° C. to 0° C., more suitably −70° C. to −30° C.

In another asepct of this invention there is provided a process for the preparation of a compound of the formula (X):

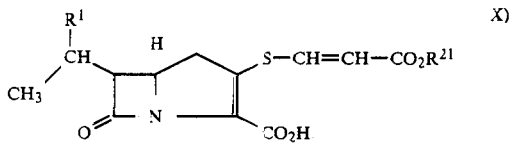

(X)

and pharmaceutically acceptable salts and in-vivo hydrolysable esters thereof wherein $R^1$ is defined in relation to formula (I) and $R^{21}$ is a hydrogen atom, a pharmaceutically acceptable salting ion or group such that $CO_2R^{21}$ is an ester group; which process comprises the reaction of a cleavable ester of a compound of the formula (I) with a compound of the formula (XI):

$$H-C\equiv C-CO_2R^{21} \qquad (XI)$$

in the presence of an acid acceptor; and subsequently:
(i) converting any cleavable ester group which is not in-vivo hydrolysable into a free acid, a pharmaceutically acceptable salt or in-vivo hydrolysable ester group;
(ii) optionally converting any cleavable ester group which is in-vivo hydrolysable into a free acid, a pharmaceutically acceptable salt or a different in-vivo hydrolysable ester group.

Suitable acid acceptors are carbonates and bicarbonates such as anhydrous potassium carbonate. The reaction is generally carried out in a dry polar solvent such as dimethylformamide. Suitably the reaction is performed at a non-extreme temperature for example −30° C. to +60° C., more suitably −10° C. to +40° C. and preferably at ambient temperature.

The group $R^1$ may be varied after the modification of the 2-position side chain. Such methods of modification can be those which are used in modifying the C-6 position substituents of natural products of the carbapenem type. Thus included herein by cross-reference are European Patent Application Publication Nos. 0004132, 0005348, 0005349 and 0007152.

In the processes hereinbefore described for the preparation of compounds of the formulae (VIII) and (X) any amino group present can be conveniently protected in conventional manner, for example as a p-nitrobenzyloxycarbonylamino group. Similarly any hydroxy group present can be conveniently protected in conventional manner, for example as a p-nitrobenzyloxycarbonyloxy group.

Methods of removing protecting groups, cleaving any ester moiety, and converting a free acid or salt to a pharmaceutically acceptable salt or ester, are as detailed in the hereinbefore mentioned European Patent Application Publications. In addition 6-ethylidene compounds of the formula (XII):

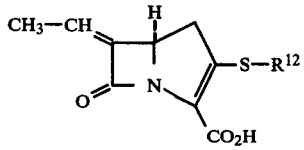

(XII)

and salts and cleavable esters thereof are envisaged as intermediates in the processes of this invention. The compounds of the formula (XII) may be readily converted to 6-ethyl compounds by known processes such as reduction.

In a particularly preferred aspect the processes of this invention are performed on hydrogenolysable esters, for example the p-nitrobenzyl ester, which may be cleaved using an approximately atmospheric pressure of hydrogen at ambient temperature with a transition metal catalyst for example palladium, preferably 5% or 10% palladium on carbon. The compounds of the formulae (I) and (III) and their pharmaceutically acceptable salts and in-vivo hydrolysable esters may be employed in the treatment of bacterial infections such as those due to *Staphylococcus aureus, Escherichia coli* and *Klebsiella aerogenes.* Thus the present invention provides a pharmaceutical composition which comprises a compound of the formulae (I) or (III) in the form of its pharmaceutically acceptable salt or in-vivo hydrolysable ester and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatvely the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections of the respiratory tract, urinary tract or soft tissues in humans, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato startch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusions in the injectably administrable compositions of this invention inclue cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The penicillin or cephalosporin is generally utilised in its conventionally administered amount.

Suitable methods of formulation include those described in the aforementioned European patent applications.

The following Examples serve to illustrate the invention.

EXAMPLE 1 p-Nitrobenzyl (5R,6S)-3-methylthio-6-[(S)-1-hydroxyethyl]-7-oxo-1-azabicyclo[3.2.0]hept-2-ene-2-carboxylate

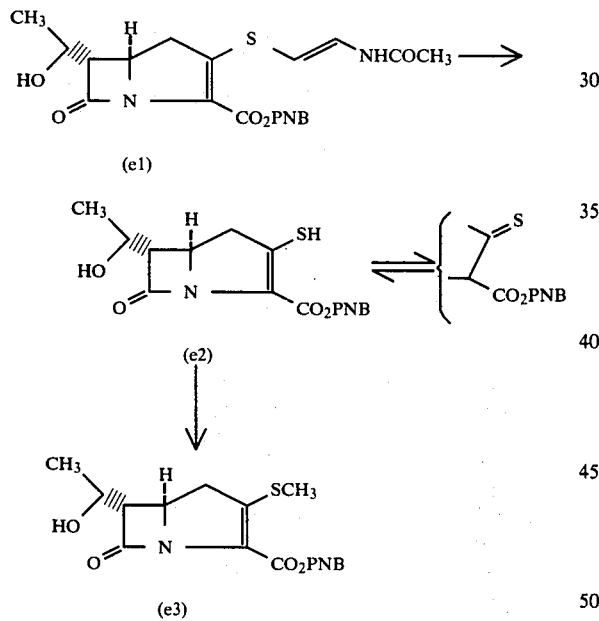

Step A

A solution of the ester (e1) (160 mg) in acetone (3 ml) containing water (10 drops) was cooled to −20°. A solution of N-bromoacetamide (55 mg) in acetone (0.5 ml) was added with stirring, and stirring was continued for 20 min at −20°. Chloroform (30 ml) was added and the solution was washed with water (30 ml). The dried (MgSO₄) organic layer was concentrated in vacuo to afford a foam (119 mg) which contained the thiol (e2); $v_{max}$. CHCl₃) 1775, 1705 cm$^{-1}$.

Step B

The product from Step A was dissolved in DMF (1 ml) and to the solution was added anhydrous potassium carbonate (25 mg) and methyl iodide (0.2 ml). After stirring the mixture vigorously for 20 min, ethyl acetate (30 ml) was added, and the organic layer was washed with water (2×30 ml) and brine (30 ml). The solution was dried (MgSO₄) and the solvent evaporated in vacuo to leave a residue which was chromatographed on silica using 2% EtOH in CHCl₃ to elute. The title methylthio-derivative (e3) was obtained as a white solid (29 mg); $v_{max}$. (KBr) 3450 (br) 1765 and 1695 cm$^{-1}$; $\lambda_{max}$. (EtOH) 320 (11,900) and 266 nm (11,300); δ(DMF-d₇) 1.29 (3H,d,J 6.5 Hz, C$\underline{H}_3$CH), 2.45 (3H,s,CH₃S), 3.22 and 3.45 (each 1H,dd,$\overline{J}$ 9 and 18 Hz, 4-CH₂), 3.50 (1H,dd,J 3 and 4 Hz, 6-CH), ca. 4.1 (1H,m,CH₃C$\underline{H}$), 4.25 (1H,dt,J 3 and 9 Hz, 5-CH), 5.17 (1H,d,J 4.5 $\overline{Hz}$, OH), 5.32 and 5.57 (each 1H,d,J 14 Hz, CH₂CO₂), 7.82 and 8.27 (each 2H,d,J 9 Hz, C₆H₄—NO₂). [M⁺, 378.0884. C₁₇H₁₈N₂O₆S requires M, 378.0882].

EXAMPLE 2

Benzyl (5R,6S)-3-methylthio-6-[(S)-1-hydroxyethyl]-7-oxo-1-azabicyclo[3.2.0]hept-2-ene-2-carboxylate

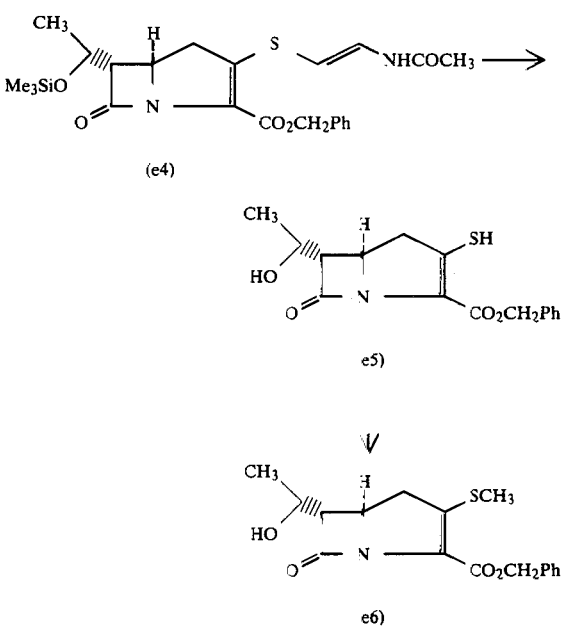

Step A

A solution of the trimethylsilyl ether (e4) (123 mg) in acetone (3 ml) containing water (3 drops) was treated with N-bromoacetamide (39 mg) at −20° with stirring. After 20 min ethyl acetate (30 ml) was added and the solution was washed with water (30 ml) followed by brine (30 ml), before drying (MgSO₄) and concentrating in vacuo. To the residue was added chloroform followed by ether and the solid which precipitated was removed by filtration. The mother liquors were concentrated in vacuo to leave a foam (86 mg) which contained the thiol (e5); $v_{max}$. (CHCl₃) 1775 and 1700 cm$^{-1}$.

Step B

The product from Step A was dissolved in DMF (1 ml), and anhydrous potassium carbonate (20 mg) followed by methyl iodide (0.5 ml) were added to the solution. After stirring the mixture for 1.5 h, ethyl acetate (30 ml) was added and the organic solution was washed with water (2×30 ml) and brine (30 ml). The dried (MgSO₄) solution was concentrated in vacuo and the residue chromatographed on silica gel using 20% petroleum ether (60°–80°) in ethyl acetate to elute. The title methylthio-derivative (e6) was obtained as a gum (3 mg); $v_{max}$. (CHCl$_3$) 3400 (br), 1780 and 1700 cm$^{-1}$; $\lambda_{max}$. (EtOH) 319 nm; δ(CHCl$_3$) 1.36 (3H,d,J 6.5 Hz, CH$_3$CH), 2.37 (3H,s,SCH$_3$), ca. 3.2 (3H,m,6-CH and 4-CH$_2$), ca. 4.15 (2H,m,5-CH and CH.CH$_3$), 5.30 (2H,AA'X,CH$_2$Ph) and 7.35 (5H,m,CH$_2$Ph). [M+, 333.1034. C$_{17}$H$_{19}$NO$_4$S requires M, 333.1033].

EXAMPLE 3 p-Nitrobenzyl
(5R,6S)-3-ethylthio-6-[(S)-1-hydroxyethyl]-7-oxo-1-azabicyclo[3.2.0]hept-2-ene-2-carboxylate

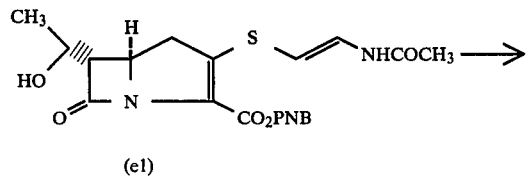

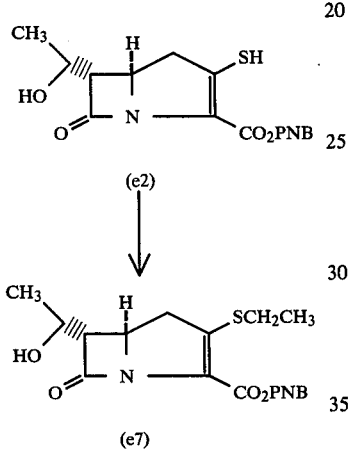

Method 1

Step A

A solution of the ester (e1) (500 mg) in acetone (10 ml) containing water (1 ml) was treated with N-bromoacetamide (154 mg) with stirring at −20° min. Work-up as described in Example 1, Step A afforded a foam (519 mg) which contained the thiol (e2).

Step B

The product from Step A was treated with ethyl iodide (0.75 ml) and anhydrous K$_2$CO$_3$ (250 mg) in DMF (5 ml) in a way analogous to that described in Example 1, Step B. Work-up as also described therein gave a product which was chromatographed on silica using a gradient elution with ethyl acetate/petroleum ether mixtures (from 80% to 100% ethyl acetate). The title ethylthio-derivative was obtained as a white crystalline solid (120 mgs); m.p. 180°-183°; $v_{max}$. (KBr) 3490, 1760 and 1700 cm$^{-1}$; $\lambda_{max}$. (EtOH) 320 (12,600) and 266 nm (11,300). δ(DMF-d$_7$) 1.26 (3H,t,J 7.5 Hz, CH$_2$), 1.27 (3H,d,J 6.5, CH$_3$CH), 2.94 (1H,q,J 7.5 Hz, SCH$_2$CH$_3$), 3.33 (1H,d,J 9 Hz, 4-CH$_2$), 3.49 (1H,dd,J 3 and 4 Hz, 6-CH), 4.09 (1H,m,CH$_3$CH), 4.24 (1H,dt,J 3 and 9 Hz, 5-CH), 5.13 (1H,d,J 5 Hz, OH), 5.29 and 5.54 (each 1H,d,J 14 Hz, CH$_2$CO$_2$), 7.82 and 8.26 (each 2H,d,J 8.5 Hz, C$_6$H$_4$—NO$_2$). [M+, 392.1045, C$_{18}$H$_{20}$N$_2$O$_6$S requires M, 392.1040].

Method 2

Step A

The ester (e1) (200 mg) was converted into the thiol derivative (e2) by the method described in Example 1, Step A.

Step B

A solution of the product from step A in dichloromethane (10 ml) was stirred vigorously with anhydrous potassium carbonate (120 mg) and triethyloxonium tetrafluoroborate (84 mg) at −10° for 20 min. The mixture was allowed to warm to room temperature for 10 min, and was then diluted with more methylene chloride (20 ml). The solution was washed with water and dilute brine, then dried (MgSO$_4$) and concentrated in vacuo. The residue was chromatographed on a column of silica gel using 20% petroleum ether in ethyl acetate followed by ethyl acetate to elute.

The ethylthio-derivative (e7), identical in all respects to the product isolated by method 1, was obtained as a white solid (19 mg).

EXAMPLE 4 p-Nitrobenzyl
(5R,6S)-3-p-bromobenzylthio-6-[(S)-1-hydroxyethyl]-7-oxo-1-azabicyclo[3.2.0]hept-2-ene-2-carboxylate

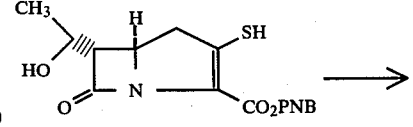

Step A

The ester (e1) (200 mg) was converted into the thiol derivative (e2) by the method described in Example 1, Step A.

Step B

The product from Step A was dissolved in DMF (2 ml) and to the solution were added anhydrous potassium carbonate (123 mg) and p-bromobenzyl bromide (223 mg). The mixture was stirred for 0.5 h at r.t. and then diluted with ethyl acetate (50 ml). The organic solution was washed with water (2×30 ml) and brine (30 ml), then dried (MgSO$_4$) and concentrated in vacuo. Chromatography of the residue on a silica-gel column using 30% petroleum ether in ethyl acetate to elute at first, gradually increasing the polarity of the eluant to 100% ethyl acetate, afforded the title p-bromobenzylthio-derivative (e8) as a solid which was further purified by trituration with ethyl acetate-ether (1:2) and filtration. The final product was obtained as a crystalline solid (35 mg); $v_{max}$. (KBr) 1770 and 1695 cm$^{-1}$; $\lambda_{max}$. (EtOH) 321 (14,300) and 266 nm (12,350); δ(DMF-d$_7$) 1.27 (3H,d,J 6.5 Hz, CH$_3$CH), ca. 3.3–3.6 (3H,m,4-CH$_2$ and 6-CH), ca. 4.1 (2H,m,5-CH and CH$_3$CH), 4.28 (2H,s,SCH$_2$), 5.19 (1H,d,J 5 Hz, OH), 5.30 and 5.57 (each 1H,d,J 14 Hz, CH$_2$CO$_2$), 7.40 and 7.58 (each 2H,d,J 8.5, C$_6$H$_4$—Br), 7.81 and 8.27 (each 2H,d,J 9 Hz, C$_6$H$_4$—NO$_2$).

EXAMPLE 5 p-Nitrobenzyl
(5R,6S)-3-p-nitrobenzylthio-6-[(S)-1-hydroxyethyl]-7-oxo-1-azabicyclo[3.2.0]hept-2-ene-2-carboxylate

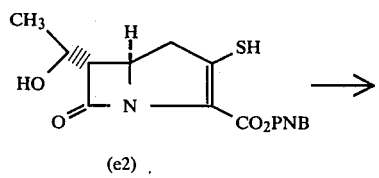

(e2)

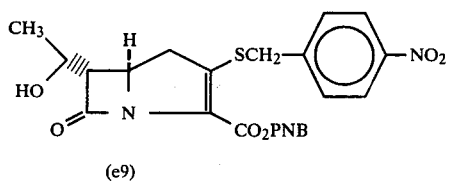

(e9)

Step A

The thiol (e2) was prepared from the ester (e1) (50 mg) by the method described in Example 1, Step A.

Step B

The product from Step A was treated with p-nitrobenzyl bromide (24 mg) and K₂CO₃ (30 mg) in a manner analogous to that described in Example 4, Step B. Work-up and chromatography as also described therein gave the title p-nitrobenzylthio-derivative (e9) (3 mg); ν$_{max.}$ (partial solution in CHCl₃) 1780 and 1710 (br) cm⁻¹.

EXAMPLE 6

Sodium (5R,6S)-3-methylthio-6-[(S)-1-hydroxyethyl]-7-oxo-1-azabicyclo[3.2.0]hept-2-ene-2-carboxylate

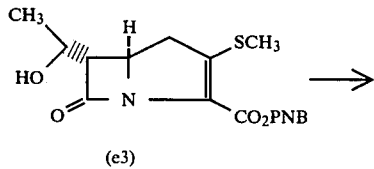

(e3)

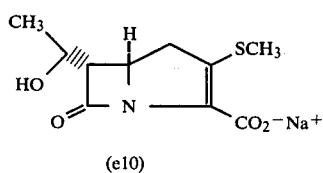

(e10)

5% Pd on C catalyst (60 mg) was shaken with hydrogen in 30% aqueous dioxan (10 ml) at ambient pressure and temperature for 0.5 h. A solution of the ester (e3) in 30% aqueous dioxan (2 ml) was added to the vessel and hydrogenation was continued for a further 3.25 h. Sodium bicarbonate (10 mg) was added and the mixture was filtered through Celite washing the pad well with water (20 ml). The filtrate was concentrated in vacuo to ca. 20 ml and the aqueous solution was washed with ethyl acetate (3×30 ml), before concentrating in vacuo to a volume of ca. 5 ml. The resulting solution was loaded onto a column (15×2.5 cm) of Biogel P2 which was eluted with water. Fractions containing the title sodium salt (e10) were identified by the chromophore at ν$_{max.}$ (H₂O) 302 nm in the UV spectrum. These were collected and combined to afford an aqueous solution of the salt (e10) (ca. 11 mg estimated by UV). The salt could be obtained as a hygroscopic solid by removal of the solvent in vacuo (aided by the addition of ethanol and toluene, respectively).

EXAMPLE 7

Sodium (5R,6S)-3-ethylthio-6-[(S)-1-hydroxyethyl]-7-oxo-1-azabicyclo[3.2.0]hept-2-ene-2-carboxylate

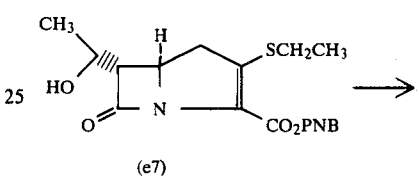

(e7)

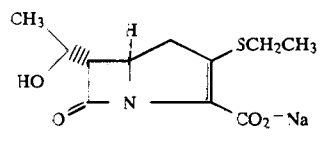

(e11)

Hydrogenolysis of the ethylthio-derivative (e7) (120 mg) was performed in the manner described in Example 6. (150 mg 5% pd-C, 26 mg NaHCO₃). After Biogel P2 chromatography (column 25×2.5 cm) the title salt (e11) (32 mg) was obtained in aqueous solution; λ$_{max.}$ 302 nm. Part of the solution was concentrated in vacuo, the final traces of water being removed by azeotroping from ethanol and then toluene, to afford the salt (e11) as a hygroscopic solid; ν$_{max.}$ (KBr) 1750 and 1590 cm⁻¹; δ(D₂O) 1.21 (3H,t,J 7.5 Hz, C$H_3$CH₂), 1.26 (3H,d,J 6.5 Hz, C$H_3$CH), 2.78 (2H,q,J 7.5 Hz, SCH₂CH₃), 3.14 (2H,m,$\overline{4}$-CH₂), 3.39 (1H,dd,J 3 and 5.5 Hz, 6-CH), 4.02 (1H,m,5-CH) and 4.15 (1H,m,CH₃C$\underline{H}$), (reference HOD at δ4.60).

EXAMPLE 8

Benzyldimethyl-n-hexadecylammonium salt of p-nitrobenzyl (5R,6R)-3-methylthio-6-[(S)-1-hydroxysulphonyloxyethyl]-7-oxo-1-azabicyclo[3.2.0]hept-2-ene-2-carboxylate

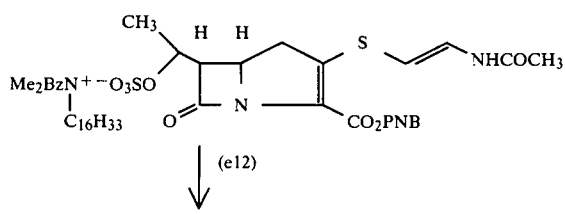

(e12)

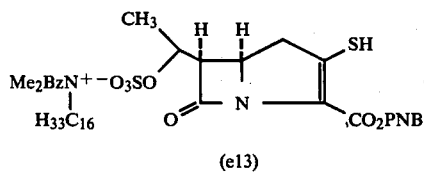
(e13)

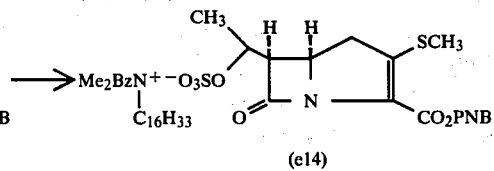
(e14)

Step A

A solution of the quaternary ammonium salt (e12) (409 mg) in 7% aqueous acetone (7.5 ml) was cooled to −20°, and a solution of N-bromoacetamide (70 mg) in acetone (1 ml) was added with stirring. After 20 min at −20° chloroform (50 ml) was added, and the solution was washed with dilute brine (At this stage it was necessary to filter the mixture through Celite in order to break up the emulsion which had formed). The organic layer was dried (MgSO4) and the solvent removed in vacuo to afford a foam (380 mg) which contained the thiol (e13); $\nu_{max}$. (CHCl3) 1775 and 1700 cm$^{-1}$.

Step B

A solution of the product from Step A in DMF (3 ml) was stirred with anhydrous potassium carbonate (75 mg) and methyl iodide (0.3 ml) at room temperature for 20 min. Chloroform (50 ml) was added and the organic solution washed with brine (2×50 ml), water (2×50 ml) and brine again (50 ml). The dried (MgSO4) solution was evaporated in vacuo and the residue chromatographed on silica gel using a gradient elution of chloroform to 30% ethanol in chloroform. Fractions containing the product (t.l.c.) were combined and concentrated in vacuo to afford the title methylthio-derivative (e14) as a foam (118 mg); $\nu_{max}$. (CHCl3) 1775 and 1700 cm$^{-1}$; $\lambda_{max}$. (EtOH) 318 and 268 nm.

EXAMPLE 9 p-Nitrobenzyl (5R,6R)-3-methylthio-6-[(S)-1-ethoxysulphonyloxyethyl]-7-oxo-1-azabicyclo[3.2.0-]hept-2-ene-2-carboxylate

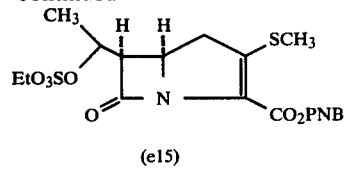
(e15)

A solution of the quaternary ammonium salt (e14) (115 mg) in dichloromethane (10 ml) was stirred with triethyloxonium tetrafluoroborate (30 mg) for 15 min at room temperature. Chloroform (20 ml) was then added and the solution was washed with water (20 ml), dried (MgSO4) and concentrated in vacuo. The product was rapidly chromatographed on silica gel (230-400 mesh ASTM) using 20% petroleum ether in ethyl acetate to elute. The title diester (e15) was obtained as a gum (29 mg); $\nu_{max}$. (CHCl3) 1780 and 1700 cm$^{-1}$; $\lambda_{max}$. (EtOH) 317 and 267 nm; δ(CDCl3) 1.42 (3H,t,J 7 Hz, CH3CH2), 1.66 (3H,d,J 6 Hz, CH3CH), 2.41 (3H,s,SCH3), 3.10 (1H,dd,J 18 and 10 Hz, 4-CH$_a$H$_b$), 3.36 (1H,dd,J 18 and 9 Hz, 4-CH$_a$H$_b$), 3.84 (1H,dd,J 6 and 10 Hz, 6-CH), 4.35 (2H,q,J 7 Hz, OCH2CH3), 4.37 (1H,m,5-CH), 5.03 (1H,m,CH3CH), 5.20 and 5.48 (each 1H,d,J 13.5, CH2CO2), 7.60 and 8.19 (each 2H,d,J 8.5 Hz, C6H4NO2).

EXAMPLE 10 p-Nitrobenzyl (5R,6R)-3-ethylthio-6-[(S)-1-ethoxysulphonyloxyethyl]-7-oxo-1-azabicyclo[3.2.0]hect-2-ene-2-carboxylate

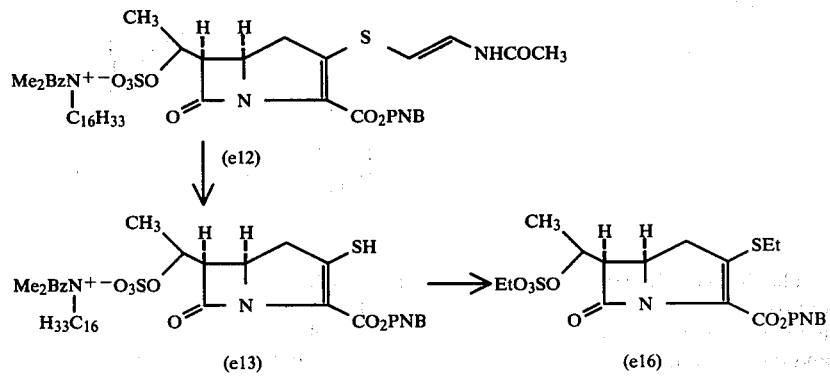

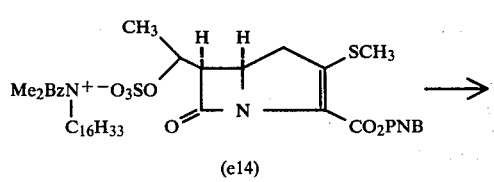
(e14)

Step A

The quaternary ammonium salt (e12) (660 mg) was converted into the thiol derivative (e13) by the method described in Example 8, Step A.

Step B

The product from Step A was dissolved in dry dichloromethane (15 ml) and to the solution was added anhydrous potassium carbonate (205 mg) and Meerwein's reagent (282 mg). The mixture was stirred for 15 min at room temperature and was then diluted with chloroform (30 ml). The organic solution was washed with very dilute brine, dried (MgSO$_4$) and concentrated in vacuo. Rapid chromatography of the residue on silica gel (230–400 ASTM) using 20% petroleum ether/ethyl acetate to elute afforded the title diester as a foam (189 mg); $\nu_{max}$.(CHCl$_3$) 1780 and 1705 cm$^{-1}$; δ(CDCl$_3$) 1.33 (3H,t,J 7 Hz, C$\underline{H}$$_3$CH$_2$S), 1.42 (3H,t,J 7 Hz, C$\underline{H}$$_3$CH$_2$O), 1.66 (3H,d,J 6 Hz, C$\underline{H}$$_3$CH), 2.90 (2H,q,J 7 Hz, CH$_3$C$\underline{H}$$_2$S), ca. 3.25 (2H,m,4-CH$_2$), 3.84 (1H,dd,J 6 and 10 Hz, 6-CH), ca. 4.30 (1H,m,5-CH), 4.35 (2H,q,J 7 Hz, CH$_3$C$\underline{H}$$_2$S), ca. 5.05 (1H,m,C$\underline{H}$CH$_3$), 5.21 and 5.48 (each 1H,d,J 14 Hz, CH$_2$CO$_2$), 7.61 and 8.20 (each 2H,d,J 8.5 Hz, C$_6$H$_4$—NO$_2$). (The n.m.r. spectrum revealed that some impurity was present in the product).

EXAMPLE 11 p-Nitrobenzyl (5R)-3-ethylthio-6-[(E)-ethylidene]-7-oxo-1-azabicyclo[3.2.0]hept-2-ene-2-carboxylate

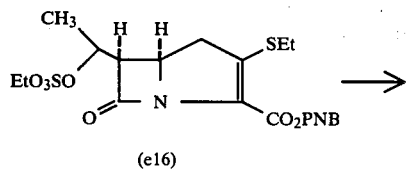

The diester (e16) (60 mg) was stirred with anhydrous potassium carbonate (41 mg) in DMF (0.5 ml) at room temperature for 30 min. Ethyl acetate (30 ml) was added and the solution was washed with water (2×30 ml) and brine (20 ml) before drying (MgSO$_4$) and evaporating in vacuo. The product was chromatographed on silica gel using 30% petroleum ether in ethyl acetate to elute. The title ethylidene derivative (e17) was isolated as a gum; $\nu_{max}$.(CHCl$_3$) 1770 and 1705 cm$^{-1}$; δ(CDCl$_3$) 1.32 (3H,t,J 7 Hz, CH$_3$C$\underline{H}$$_2$), 1.83 (3H,d,J 7 Hz, C$\underline{H}$$_3$CH), 2.84 (2H,q,J 7 Hz, SC$\underline{H}$$_2$CH$_3$), 3.04 and 3.27 (each 1H,dd,J 18 and 9 Hz, 4-CH$_2$), 4.77 (1H, brt,J 9 Hz, 5-CH), 5.23 and 5.53 (each 1H,d,J 13.5 Hz, CH$_2$CO$_2$), 6.43 (1H,qd,J 7 and 1.5 Hz, CH$_3$C$\underline{H}$), 7.17 and 8.19 (each 2H,d,J 8.5 Hz, C$_6$H$_4$—NO$_2$).

EXAMPLE 12

Benzyldimethyl-n-hexadecylammonium salt of p-nitrobenzyl (5R,6R)-3-ethylthio-6-[(S)-1-hydroxysulphonyl-oxyethyl]-7-oxo-1-azabicyclo[3.2.0]hept-2-ene-2-carboxylate

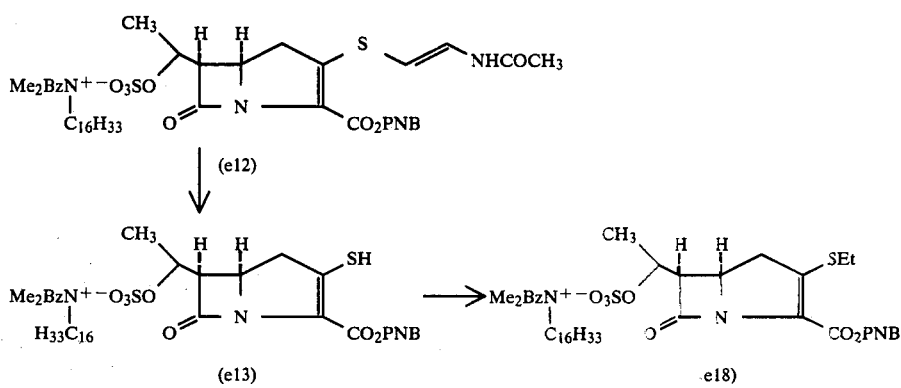

Step A

The quaternary ammonium salt (e12) (660 mg) was converted into the thiol (e13) by the method described in Example 8, Step A.

Step B

The thiol derivative (e13) was treated with ethyl iodide and potassium carbonate in DMF in a manner analogous to that described in Example 8, Step B. The title ethylthio-derivative (e18) was obtained as a foam (240 mg); $\nu_{max}$.(CHCl$_3$) 1780 and 1700 cm$^{-1}$; $\lambda_{max}$.(EtOH) 317 and 267 nm.

EXAMPLE 13

Sodium salt of p-nitrobenzyl (5R,6R)-3-ethylthio-6-[(S)-1-hydroxysulphonyloxyethyl]-7-oxo-1-azabicyclo[3.2.0]hept-2-ene-2-carboxylate

Method 1

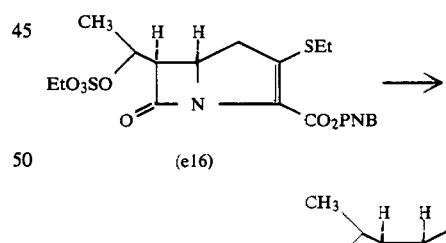

A solution of the diester (e16) (150 mg) in DMF (2 ml) was stirred at room temperature in the presence of sodium iodide (172 mg) for 4.5h. The solution was evaporated to dryness and the residue chromatographed on silica gel using a gradient elution from chloroform to 25% ethanol in chloroform. Fractions containing the required product (t.l.c. and u.v.) were combined and evaporated in vacuo to afford the title compound as a solid (23 mg); $\lambda_{max}$.(EtOH) 318 and 267 nm, (H$_2$O) 317 and 275nm; $\nu_{max}$.(KBr) 1765 and 1695 cm$^{-1}$.

Method 2

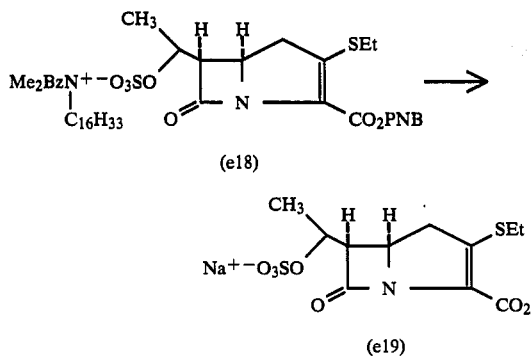

A column (10×2.5 cm) of Amberlyst A26 resin was washed successively with 100 ml quantities of methanol, water, ethanol and 30% CHCl$_3$ in EtOH. A solution of the quaternary ammonium salt (e18) (190 mg) in 30% CHCl$_3$ in EtOH (5 ml) was loaded on to the column which was then eluted successively with 100 ml portions of 30% CHCl$_3$ in EtOH, ethanol and water. Finally elution with a mixture (1:1) of 5% NaCl in H$_2$O and methanol afforded a solution of the mono sodium salt (e19). This may be further purified by silica gel chromatography as described in method 1.

EXAMPLE 14

Disodium (5R,6R)-3-ethylthio-6-[(S)-1-sulphonato-oxyethyl]-7-oxo-1-azabicyclo[3.2.0]hept-2-ene-2-carboxylate

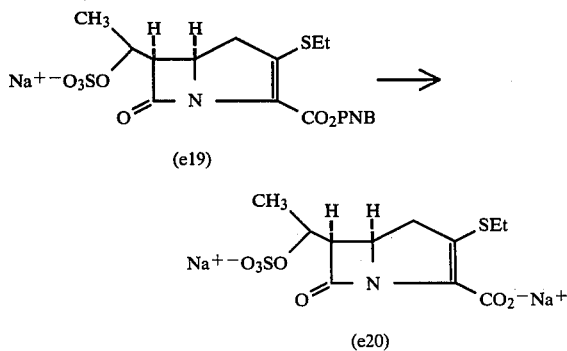

5% Pd on C catalyst (15 mg) was shaken with hydrogen in 30% aqueous dioxan (4 ml) for 30 min. A solution of the ester (e19) (7 mg) in 30% aqueous dioxan (1 ml) was introduced into the vessel and hydrogenation was continued for 3h. NaHCO$_3$ (2 mg) was added to the mixture which was filtered over Celite, washing the pad with water (10 ml), and the solution was concentrated in vacuo to ca. 10 ml. The aqueous solution was washed with ethyl acetate (3×15 ml) and then concentrated in vacuo to ca. 3 ml. The solution was loaded onto a column of Biogel P2 (2.5×10 cm) which was then eluted with water. Fractions containing the title disodium salt (e20) were identified by the absorption in the UV spectrum at $\lambda_{max}$. 298 nm.

EXAMPLE 15 p-Nitrobenzyl(5R,6S)-3-acetylthio-6-[(S)-1-acetoxyethyl]-7-oxo-1-azabicyclo[3.2.0]hept-2-ene-2-carboxylate

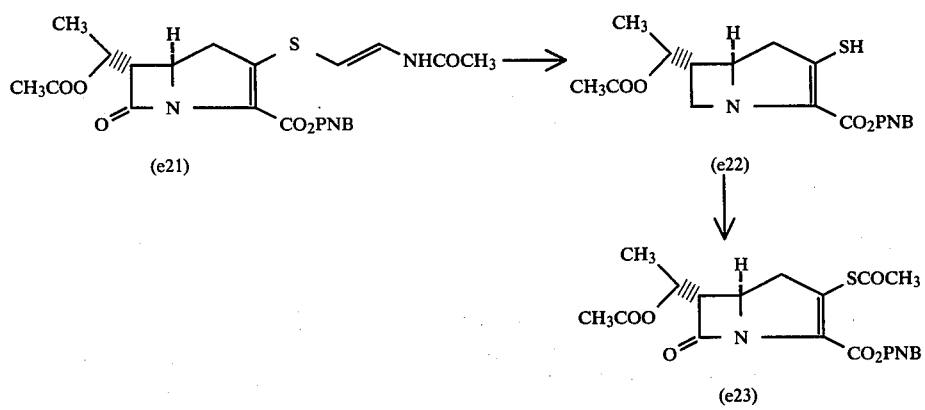

Step A

The acetoxy derivative (e21) (90 mg) was dissolved in acetone (2 ml) containing water (3 drops). The solution was cooled to −20° and a solution of N-bromoacetamide in acetone (0.5 ml) was added with stirring. After 25 min at −20° the solution was diluted with chloroform (25 ml) and washed with water (25 ml). The organic layer was dried (MgSO$_4$) and concentrated in vacuo to afford a gum, which contained the thiol (e22), $\nu_{max}$.(CHCl$_3$) 1780, 1730 and 1700 sh cm$^{-1}$.

Step B

The product was dissolved in pyridine (1 ml) and to the stirred solution was added acetyl chloride (3 drops). After 10 min the mixture was evaporated to dryness and the product was partitioned between chloroform (25 ml) and water (25 ml). The organic layer was washed with pH 3 phosphate buffer (20 ml), dilute aqueous sodium bicarbonate (20 ml) and water (20 ml), and then dried (MgSO$_4$) and concentrated in vacuo. The residue was chromatographed on silica gel using 50% petroleum ether-ethyl acetate to elute. The first-eluted component was the title diacetyl derivative (e23) (5 mg); $\nu_{max}$.(CHCl$_3$) 1790, 1740 and ca. 1700 sh cm$^{-1}$; $\nu_{max}$.(EtOH) ca. 300 sh and 267 nm. δ(CDCl$_3$)inter alia 1.43 (3H,d,J 6.5 Hz, C$\underline{H}_3$CH), 2.11 (3H,s,CH$_3$CO), 2.40 (3H,s,COCH$_3$) and ca. 5.15 (1H,m,CH$_3$C$\underline{H}$)

EXAMPLE 16 p-Nitrobenzyl(5R,6S)-3-(2-ethoxycarbonylethenylthio)-6-8(S)-1-acetoxyethyl]-7-oxo-1-azabicyclo[3.2.0]hept-2-ene-2-carboxylate

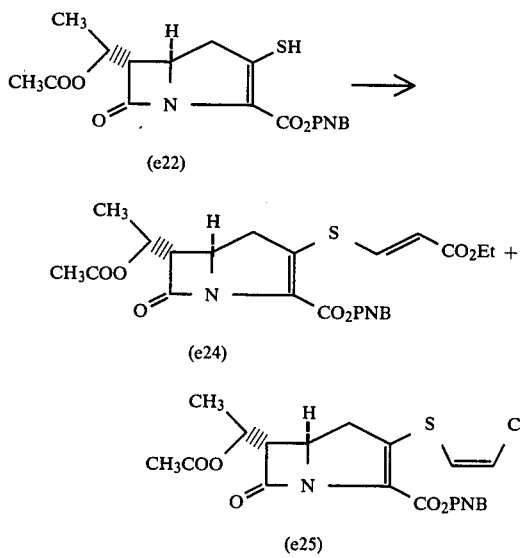

Step A

A solution of the acetoxy-derivative (e21) (330 mg) in a mixture of acetone (7 ml) and water (0.75 ml) was cooled to −20°. A solution of N-bromoacetamide (93 mg) in acetone (1 ml) was added with stirring, and stirring at −20° was continued for 20 min. Chloroform (50 ml) was added and the organic solution was washed with water (50 ml), dried (MgSO₄) and evaporated in vacuo to afford a foam, which contained the thiol/thione (e22).

Step B

The product from Step A was dissolved in DMF (3 ml) and to the solution was added ethyl propiolate (66 mg) followed by anhydrous potassium carbonate (93 mg) with stirring. After stirring for 15 min at ambient temperature, ethyl acetate (40 ml) was added and the solution was washed with water (3×30 ml) and brine (30 ml). Evaporation of the dried (MgSO₄) solution gave a residue which was chromatographed on silica gel using 20% petroleum ether in ethyl acetate to elute.

The first-eluted component (8 mg) was the (E)-isomer of the title compound (e24); $\nu_{max}$. (CHCl₃) 1790, 1735 and 1710 cm⁻¹; $\lambda_{max}$. (EtOH) 333 and 267 nm.

The next-eluted product (51 mg) was the (Z)-isomer of the title compound (e25); $\nu_{max}$. (CHCl₃) 1790, 1740 and 1710 cm⁻¹; $\lambda_{max}$. (EtOH) 335 and 267 nm; δ(CDCl₃) 1.30 (3H,t,J 7 Hz, C$\underline{H}_3$CH₂), 1.42 (3H,d,J 6.5 Hz, C$\underline{H}_3$CH), 2.08 (3H,s,CH₃C$\underline{O}$), 3.18 and 3.44 (each 1H,d,$\overline{J}$ 9 and 18 Hz, 4-CH₂), 3.49 (1H,dd,J 3 and 4 Hz, 6-CH), 4.12 (1H,dt,J 3 and 9 Hz, 5-CH) overlapping with 4.22 (2H,q,J 7 Hz, CH₃C$\underline{H}_2$), 5.24 (1H,m.CH₃C$\underline{H}$), 5.27 and 5.52 (each 1H,d,J 14 Hz, CH₂CO₂), 5.97 and 7.22 (each 1H,d,J 10 Hz, CH═CH), 7.68 and 8.21 (each 2H,d,J 9 Hz, C₆$\underline{H}_4$-NO₂).

EXAMPLE 17 p-Nitrobenzyl (5R,6S)-3-[2-(2-p-nitrobenzyloxycarbonylaminoethoxycarbonyl)ethenylthio]-6-[(S)-1-hydroxyethyl]-7-oxo-1-azabicylo [3.2.0]hept-2-ene-2-carboxylate

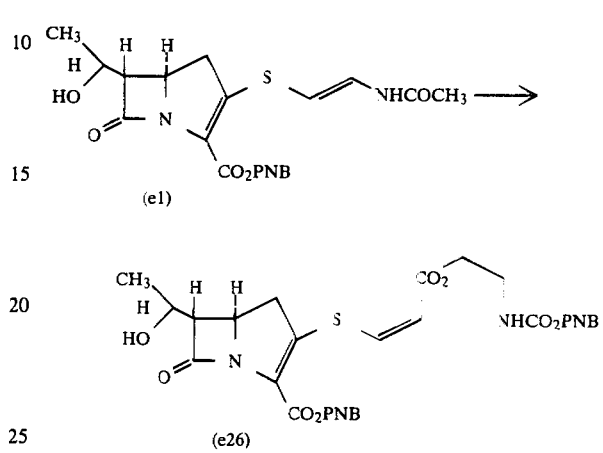

Step A

A solution of the ester (e1) (250 mg) in dioxan (5 ml) containing water (0.75 ml) was stirred with N-bromoacetamide (75 ml) for 5 minutes at ambient temperature. Chloroform (30 ml) was added and the solution was washed with 0.05 M phosphate buffer (pH7) solution (20 ml) and brine (20 ml). The solution was dried (MgSO₄) and evaporated in vacuo to afford a foamy product which contained the thiol/thione (e2).

Step B

The product from step A was dissolved in DMF (3 ml) and to the solution was added with stirring, anhydrous potassium carbonate (75 ml) followed by 2-(p-nitrobenzyloxycarbonylaminoethyl)propiolate (200 mg). After stirring for 15 minutes the reaction mixture was diluted with ethyl acetate (30 ml) and the organic solution was washed with water (3×30 ml) and brine (30 ml). Evaporation of the dried (MgSO₄) organic layer gave a product which was chromatographed on a column of silica gel using ethyl acetate followed by 10% ethanol-ethyl acetate. The major product obtained (81 mg) consisted of p-nitrobenzyl (5R,6S)-3-[2-(2-p-nitrobenzyloxycarbonylaminoethoxycarbonyl) ethenylthio]-6-[(S)-1-hydroxyethyl]-7-oxo-1-azabicyclo [3.2.0]hept-2-ene-2-carboxylate, as a mixture of the Z-isomer (e26) and the corresponding E-isomer (ca. 85:15); $\lambda_{max}$. (EtOH) 337 and 265 nm. $\nu_{max}$. (CHCl₃) 1780 and 1720 cm⁻¹; δ(DMF-d₇) 1.29 (3H, d, J 6.5 Hz, C$\underline{H}_3$CH), 3.30–3.70 (5H, m, 4-CH₂, CH₂N and 6-CH), 4.0–4.5 (4H, m, OC$\underline{H}_2$, 5-CH and CH₃C$\underline{H}$), ca. 5.2 (1H, OH), 5.23 (2H, s, C$\underline{H}_2$Ar), 5.37 and 5.60 (each 1H, d, J 14 Hz, C$\underline{H}_2$Ar), 6.06 (1H, d, J SC$\underline{H}$═ for Z-isomer) ca. 7.40–8.05 (6H, m, 4×aromatic protons and ═CHCO₂) and 8.25 (4H, d, J 9 Hz, aromatic protons). The E-isomer shows inter alia δ 6.23 (1H, d, J 16 Hz, SC$\underline{H}$═).

EXAMPLE 18

(5R,6S)-3-[2-(Z)-(2-Aminoethoxycarbonyl)ethenylthio]-6-[(S)-1-hydroxyethyl]-7-oxo-1-azabicyclo[3.2.0-]hept-2-ene-2-carboxylic acid

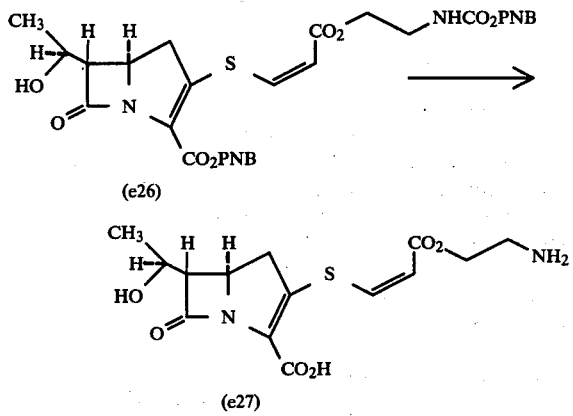

A mixture of the ester (e26) (80 mg), dioxan (10 ml), ethanol (0.8 ml), water (3 ml), 0.05 M pH7 phosphate buffer (4 ml) and 10% palladium on charcoal (110 mg) was shaken in an atmosphere of hydrogen for 2 hours. The mixture was filtered through Celite washing with water (15 ml) and the solution was then concentrated to a volume of ca. 20 ml. The aqueous solution was washed with ethyl acetate-ether (1:1;2×50 ml) and then concentrated to ca. 5 ml before loading onto a column of XAD-2 (2.5×10 cm). Elution with water gave fractions containing (5R,6S)-3-[2-(Z)-(2-aminoethoxycarbonyl)ethenylthio]-6-[(S)-1-[3.2.0]hydroxyethyl]-7-oxo-1-azabicyclo[3.2.0]hept-2-ene-2-carboxylic acid (e27); $\lambda_{max}$. (H$_2$O) 325 nm. (contains ca. 15% of corresponding E-isomer).

EXAMPLE 19 p-Nitrobenzyl (5R,6R)-3-[2-(Z)-(2-p-nitrobenzyloxycarbonylaminoethoxycarbonyl)ethenylthio]-6-[(S)-1-hydroxyethyl]-7-oxo-1-azabicyclo[3.2.0]hept-2-ene-2-carboxylate

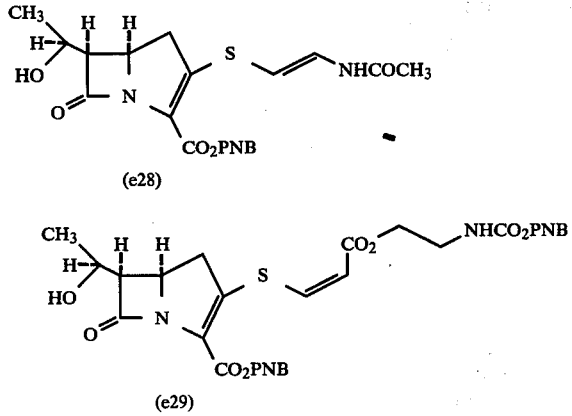

Step A

The ester (e28) (300 mg) was treated with N-bromoacetamide (92 mg) was described in Example 17.

Step B

The product from step A was treated with 2-p-nitrobenzyloxycarbonylaminoethylpropiolate (300 mg) as described in Example 17. p-Nitrobenzyl (5R,6R)-3-[2-(2-p-nitrobenzyloxycarbonylaminoethoxycarbonyl)ethenylthio]-6-[(S)-1-hydroxyethyl]-7-oxo-1-azabicyclo[3.2.0]hept-2-ene-2-carboxylate (e29) was obtained initially as a foam (166 mg) which was crystallised from acetone-ether to afford a solid (120 mg). The ratio of Z- and E- isomers was ca. 95:5 $\lambda_{max}$. (EtOH) 334 and 264 nm., $\nu_{max}$. (KBr) 1785 and 1710 cm$^{-1}$, δ(DMF-d$_7$) 1.32 (3H, d, J 6.5 Hz, C$\underline{H}_3$CH), ca. 3.3–3.8 (5H, m, 4-CH$_2$, NCH$_2$ and 6-CH), ca. 4.05–4.55 (4H, m OCH$_2$, 5-CH and CH$_3$C$\underline{H}$), 5.15 (1H, br, OH), 5.24 (2H, s, CH$_2$Ar), 5.37 and 5.59 (each 1H, d, J 14 Hz, ArCH$_2$) 6.10 (1H, d, J 10 Hz, SC$\underline{H}$= for Z-isomer) and ca. 7.4–7.95 and 8.2–8.35 (10$\underline{H}$, m, 8×aromatic protons, =C$\underline{H}$CO$_2$ and NH).

EXAMPLE 20

(5R,6R)-3-[2-(Z)-(2-Aminoethoxycarbonyl)ethenylthio]-6-[(S)-1-hydroxyethyl]-7-oxo-1-azabicyclo[3.2.0-]hept-2-ene-2-carboxylic acid

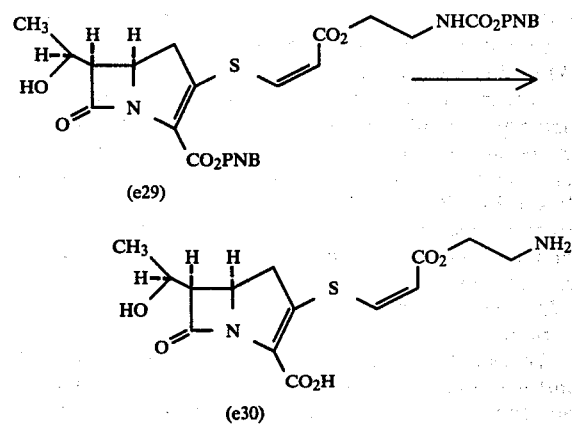

The ester (e29) (150 mg) was dissolved in a mixture of dioxan (10 ml) and 0.05 M pH7 phosphate buffer (4.5 ml), and the solution was shaken with 5% palladium on charcoal (200 mg) in an atmosphere of hydrogen for 2 hours. The mixture was filtered over Celite, washed with water (20 ml), and the solution was then concentrated in vacuo to a volume of ca. 20 ml. The solution was washed with ethyl acetate (4×25 ml), and was then freeze-dried to afford (5R,6R)-3-[2-(Z)-2-aminoethoxycarbonyl)ethenylthio]-6-[(S)-1-hydroxyethyl]-7-oxo-1-azabicyclo[3.2.0]hept-2-ene-2-carboxylic acid (e30) as a solid; $\lambda_{max}$. (H$_2$O) 325 nm., $\sigma_{max}$. (KBr) 1750, 1690 and 1565–1610 (br) cm$^{-1}$. (The product contained ca. 5% of the corresponding E-isomer).

EXAMPLE 21

The Sodium salt of p-nitrobenzyl (5R,6R)-3-[(Z)-2-p-nitrobenzyloxycarbonylethenylthio]-6-[(S)-1-hydroxysulphonyloxyethyl]-7-oxo-1-azabicyclo [3.2.0]hept-2-ene-2-carboxylate

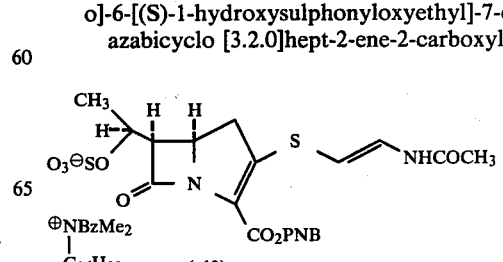

-continued

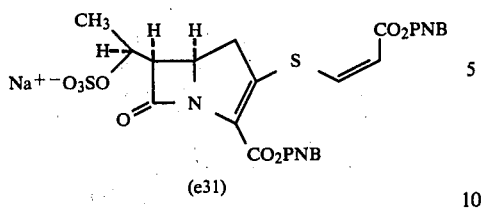

(e31)

Step A
The mono quaternaryammonium derivative (e12) (1.448 g) was dissolved in dioxan (20 ml) containing water (1.5 ml) and N-bromoacetamide (220 mg) was added with stirring. After 4.5 minutes, the solution was diluted with CHCl₃ (40 ml) and was then washed with water (50 ml) and brine (30 ml). Evaporation of the dried (MgSO₄) organic layer gave a foam which contained the thiol (e13).

Step B
A solution of the product from step A in DMF (10 ml) was stirred at room temperature with p-nitrobenzyl propiolate (500 mg) and potassium carbonate (220 mg). After 20 minutes ethyl acetate (70 ml) was added and the organic solution was washed with water (3×50 ml) and brine (50 ml). The solution was dried (MgSO₄) and evaporated in vacuo to give a crude product which was chromatographed on silica gel using chloroform followed by 5%, 10%, 15% and 20% ethanol in chloroform respectively, to elute. Fractions containing the major single component were combined and evaporated to give a foamy product (0.54 g). [ν$_{max.}$ (CHCl₃) 1785 and 1710 cm⁻¹.]

Step C
To a solution of the product from step B in acetone (5 ml) was added a solution of sodium iodide (80 mg) in acetone (1 ml). Scratching of the vessel with a glass rod induced precipitation of a white solid. More acetone was added and the solid filtered off and washed with acetone followed by ether. The solid (193 mg) consisted of the sodium salt of p-nitrobenzyl (5R, 6R)-3-[(Z)-2-p-nitrobenzyloxycarbonyl-ethenyl-thio]-6-[(S)-1-hydroxysulphonyloxyethyl]-7-oxo-1-azabicyclo [3.2.0 ]hept-2-ene-2-carboxylate (e31). λ$_{max.}$ (H₂O) 335 (20,410) and 272 (20,150), ν$_{max.}$ (KBr) 1775 and 1710 cm⁻¹, δ (DMF-d₇) 1.48 (3H, d, J 6.5 Hz, CH₃CH), ca. 3.2–3.6 (1H, m, 4-CH$_a$), 3.7–4.1 (2H, m, 6-C̄H and 4-CH$_b$), 4.25–4.80 (2H, m, 5-CH and CH₃CH), 5.41 (2H, s, CH₂Ar), 5.38 and 6.60 (each 1H, d, J 14 Hz, CH₂Ar), 6.24 (1H, d, J 10 Hz, SCH=), ca. 7.70–7.95 (m) and 8.29 (d, J 9 Hz) [Total 9H, 2×C₆H̄₄—NO₂ and =CH̄CO₂).

EXAMPLE 22

The Trisodium salt of (5R,6R)-3-[(Z)-2-carboxyethenylthio]-6-[(S)-1-hydroxysulphonyloxyethyl]-7-oxo-1-azabicyclo[3.2.0]hept-2-ene-2-carboxylic acid

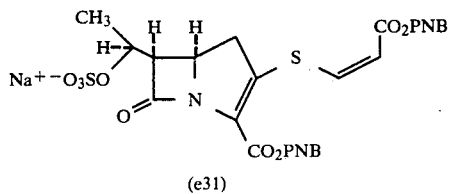

(e31)

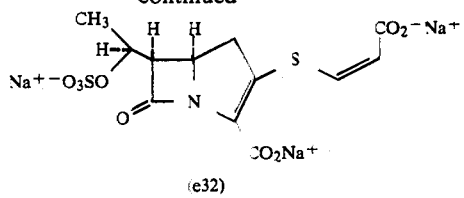

(e32)

A solution of the ester (e31) (150 mg) in 25% aqueous dioxan (20 ml) was hydrogenated in the presence of 5% palladium on carbon (200 mg) for 3.5 hours after previously prehgydrogenating the catalyst for 0.5 hours. Sodium bicarbonate (38 mg) was added to the mixture which was then filtered over Hiflo washing with water (20 ml). The filtrate was concentrated to ca. 20 ml and then washed with ethyl acetate (3×20 ml). The aqueous solution was further concentrated to ca. 5 ml and then chromatographed on a column of Biogel P2 (2.5×25 cm). Fractions containing the product were combined and evaporated in vacuo to afford the trisodium salt of (5R,6R)-3-[(Z)-2-carboxyethenylthio]-6-[(S)-1-hydroxysulphonyloxyethyl]-7-oxo-1-azabicyclo[3.2.0]hept-2-ene-2-carboxylic acid (e32) as a white solid (60 mg; λ$_{max.}$ (H₂O) 325 nm., ν$_{max.}$ (KBr) 1775, 1630 sh and 1580 cm⁻¹.

EXAMPLE 23 p-Nitrobenzyl (5R,6R)-3-[2-p-nitrobenzyloxycarbonylethenylthio]-6-[(S)-1-hydroxyethyl]-7-oxo-1-azabicyclo [3.2.0]hept-2-ene-2-carboxylate: (E) and (Z) isomers

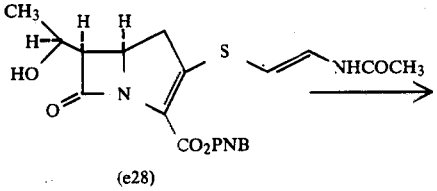

(e28)

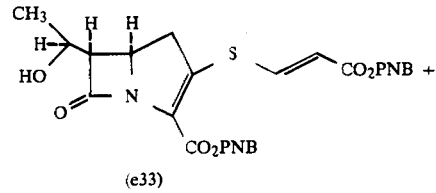

(e33)

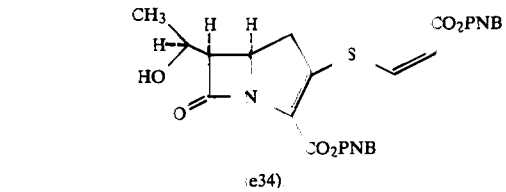

(e34)

Step A
A solution of the ester (e28) (300 mg) in a mixture of dioxan (6 ml) and water (0.9 ml) was stirred with N-bromoacetamide (90 ml) at room temperature for 4.5 minutes. Chloroform (30 ml) was added and the organic solution was washed with 0.05 M pH7 phosphate buffer (20 ml) followed by dilute brine (20 ml). Evaporation of the dried (MgSO₄) organic layer afforded a foam.

Step B

The product from step A was dissolved in DMF (3 ml) and potassium carbonate (45 mg) and p-nitrobenzyl propiolate (275 mg) were added. The mixture was stirred for 25 minutes and was then diluted with ethyl acetate (30 ml). The organic solution was washed with water (3×30 ml) and brine (20 ml), then dried (MgSO$_4$) and evaporated in vacuo. The residue was chromatographed on silica-gel using a gradient elution of 50% ethyl acetate-petrol to 100% ethyl acetate. Two main products were obtained. The first (28 mg) corresponded to p-nitrobenzyl (5R,6R)-3-[(E)-2-p-nitrobenzyloxycarbonylethenylthio]-6-[(S)-1-hydroxyethyl]-7-oxo-1-azabicyclo [3.2.0]hept-2-ene-2-carboxylate (e33); $\lambda_{max}$. (EtOH) 335 and 265 nm., $\nu_{max}$. (CHCl$_3$) 1785 and 1715 cm$^{-1}$, δ (Me$_2$CO) 1.35 (3H, d, J 6 Hz, CH$_3$CH), ca. 3.25–3.90 (3H, m, 4-CH$_2$ and 6-CH), ca. 4.45 (3H, m, 5-CH, CH$_3$CH and OH), 5.35 (2H, s, CH$_2$Ar), 5.30 and 5.55 (each 1H, d, J 14 Hz, ArCH$_2$), 6.30 (1H, d, J 15 Hz, SCH=), 7.62–8.30 (9H, m, 2×C$_6$H$_4$—NO$_2$ and =CHCO$_2$).

The second product (100 mg) was the corresponding Z-isomer (e34) $\lambda_{max}$. (EtOH) 335 (21,998) and 263 (21,785), $\nu_{max}$. (KBr) 1780 and 1710 cm$^{-1}$, δ (DMF-d$_7$) 1.31 (3H, d, J 6.5 Hz, CH$_3$CH), ca. 3.40–3.85 (3H, m, 4-CH$_2$ and 6-CH), 4.05–4.55 (2H, m, 5-CH and CHCH$_3$), 5.11 (1H, d, J 4.5 Hz, OH), 5.42 (2H, s, CH$_2$Ar), 5.39 and 5.61 (each 1H, d, J 13 Hz, CH$_2$Ar), 6.26 (1H, d, J 10 Hz, SCH=), 7.07–8.05 (5H, m, =CH.CO$_2$ and 4×aromatic protons) and 8.28 (4H, d, J 9 Hz, aromatic protons) [M, 525.0838 corresponds to M$^+$—CH$_3$C=OH].

EXAMPLE 24

The Disodium salt of (5R,6R)-3-[(Z)-2-carboxyethenylthio]-6-[(S)-1-hydroxyethyl]-7-oxo-1-azabicyclo[3.2.0]hept-2-ene-2-carboxylic acid

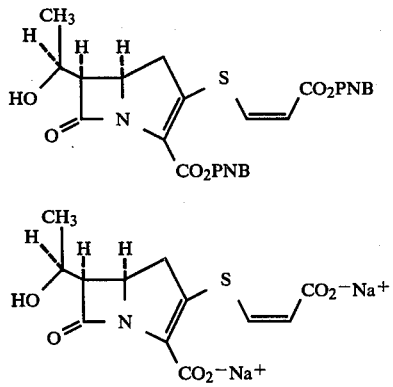

The ester (e34) (95 mg) was hydrogenolysed in the manner described in Example 22. After chromatography on Biogel P2 (10×2.5 cm) and evaporation of the solvent, the disodium salt of (5R,6R)-3-[(Z)-2-carboxyethenylthio]-6-[(S)-1-hydroxyethyl]-7-oxo-1-azabicyclo [3.2.0]hept-2-ene-2-carboxylic acid (e35) was obtained as a white solid (28 mg); $\lambda_{max}$. (H$_2$O) 325 nm., $\nu_{max}$. (KBr) 1750 and 1590 cm$^{-1}$.

DEMONSTRATION a. Antibacterial effectiveness of compounds of Examples 6 and 7 in agar.

| Organism | M.I.C. (μg/ml) Ex. 6 | M.I.C. (μg/ml) Ex. 7 |
|---|---|---|
| Citrobacter freundii E8 | 12.5 | 2.5 |
| Enterobacter cloacae N1 | 28 | 5.0 |
| Escherichia coli 0111 | 12.5 | 5.0 |
| Escherichia coli JT39 | 12.5 | 2.5 |
| Klebsiella aerogenes A | 12.5 | 2.5 |
| Proteus mirabilis C977 | 50 | 12.5 |
| Proteus morganii 1580 | 25 | 2.5 |
| Proteus rettgeri WM16 | 25 | 5.0 |
| Proteus vulgaris W091 | 25 | 5.0 |
| Pseudomonas aeruginosa A | >100 | >50 |
| Salmonella typhimurium CT10 | 12.5 | 2.5 |
| Serratia marcescens US20 | 12.5 | 5.0 |
| Shigella sonnei MB 11967 | 12.5 | 5.0 |
| Bacillus subtilis A | 25 | 5.0 |
| Staphylococcus aureus Oxford | 3.1 | 1.2 |
| Staphylococcus aureus Russell | 6.2 | 1.2 |
| Staphylococcus aureus 1517 | 100 | NG |
| Streptococcus faecalis I | >100 | >50 |
| Streptococcus pneumoniae CN33 | — | NG |
| Streptococcus pyogenes CN10 | 25 | 1.2 | b. Antibacterial effectiveness of the compound of Example 14 and MM 13902 in agar.

| Organism | Ex. 14 | MM 13902 |
|---|---|---|
| Escherichia coli JT1 | ≦0.1 | ≦0.1 |
| NCTC 15418 | ≦0.1 | ≦0.1 |
| E8 | ≦0.1 | ≦0.1 |
| 5 | ≦0.1 | ≦0.1 |
| Ba78R+ | 0.2 | 0.8 |
| JT4R+ | 0.4 | 1.6 |
| JT20R+ | 0.8 | 1.6 |
| E96R+ | ≦0.1 | 0.2 |
| JT425C+ | ≦0.1 | 0.8 |
| JT414C+ | 0.2 | 0.4 |
| Klebsiella aerogenes T219 | ≦0.1 | ≦0.1 |
| R112 | ≦0.1 | 0.2 |
| I281 | ≦0.1 | 0.2 |
| Va2R+ | 0.8 | 6.2 |
| Proteus mirabilis T318 | 0.4 | ≦0.1 |
| 889 | 0.8 | 0.2 |
| Proteus morganii I | 0.4 | 0.2 |
| T361 | 0.4 | 0.2 |
| Proteus rettgeri I | 0.4 | 0.2 |
| R110 | 0.2 | 0.2 |
| Proteus vulgaris X | 0.4 | 0.4 |
| NCTC 4395 | 0.2 | 0.1 |
| Enterobacter cloacea T749 | 6.2 | 12.5 |
| NCTC 10005 | 6.2 | 12.5 |
| Enterbacter aerogenes T660 | 0.2 | 0.4 |
| NCTC 10006 | 0.4 | 0.4 |
| Citrobacter freundii W18 | 1.6 | 6.2 |
| T221 | 1.6 | 6.2 |
| Serratia marcescens SM27 | 0.4 | 1.6 |
| Wo146 | 1.6 | 3.1 |
| Pseudomonas aeruginosa W975 | 100 | 50 |
| NCTC 10662 | 50 | 25 |
| Dalgleish | 50 | 50 |
| Staphylococcus aureus Smith | 0.4 | 1.6 |
| ATCC 25923 | 0.4 | 1.6 |
| ME9+ | 1.6 | 3.1 |
| T67+ | 0.8 | 0.8 |
| T150+ | 0.4 | 1.6 |
| Streptococcus faecalis C90 | 12.5 | 6.2 |
| T1101 | 12.5 | 6.2 |
| Bacteroides fragilis 2118 | 0.2 | 0.2 |
| B3 | 0.4 | 0.4 |
| WS12 | 0.2 | 0.2 |
| BC16 | 1.6 | 1.6 |
| VP1 8249 | 0.4 | 0.2 |
| WS41 | 0.2 | 0.4 |
| WS1 | 6.2 | 6.2 |
| BC4 | 0.8 | 1.6 |

DEMONSTRATION OF EFFECTIVENESS

| ORGANISM | MIC (μg/ml) in agar of compound of Example | | | |
|---|---|---|---|---|
| | 18 | 20 | 22 | 24 |
| *Citrobacter freundii* E8 | 3.1 | 0.2 | 25 | 1.2 |
| *Enterobacter cloacea* N1 | 3.1 | 0.2 | 0.5 | 0.5 |
| *Escherichia coli* 0111 | 3.1 | ≦0.1 | 1.2 | 0.2 |
| *Escherichia coli* JT 39 | 3.1 | 0.2 | 1.2 | 5.0 |
| *Klebsiella aerogenes* A | 3.1 | ≦0.1 | 1.2 | 0.2 |
| *Proteus mirabilis* C977 | 12.5 | 0.4 | 1.2 | 0.5 |
| *Proteus morganii* 1580 | 3.1 | — | 0.5 | 0.5 |
| *Proteus rettgeri* WM16 | 6.2 | 0.2 | 1.2 | 0.5 |
| *Proteus vulgaris* W091 | 6.2 | 0.4 | 1.2 | 0.5 |
| *Pseudomonas aeruginosa* A | 25 | 25 | >50 | >50 |
| *Salmonella typhimurium* CT10 | 3.1 | ≦0.1 | 1.2 | 0.5 |
| *Serratia marcescens* US20 | 1.2 | ≦0.1 | 5.0 | 2.5 |
| *Shigella sonnei* MB 11967 | 3.1 | 0.2 | 1.2 | 0.5 |
| *Bacillus subtilis* A | — | ≦0.1 | 0.5 | ≦0.1 |
| *Staphylococcus aureus* Oxford | ≦0.1 | ≦0.1 | 2.5 | 0.5 |
| *Staphylococcus aureus* Russell | 0.4 | — | 2.5 | 0.5 |
| *Staphylococcus aureus* 1517 | 6.2 | 0.2 | 25 | 5.0 |
| *Streptococcus faecalis* I | 12.5 | ≦0.1 | 12.5 | 2.5 |
| *Streptococcus pneumoniea* CN33 | — | ≦0.1 | — | ≦0.1 |
| *Streptococcus pyogenes* CN10 | ≦0.1 | ≦0.1 | — | ≦0.1 |
| *E. coli* ESS | 1.0 | ≦0.1 | 1.2 | ≦0.1 |

EXAMPLE 25

Sodium (5R,6S)-6-[(S)-1-acetoxyethyl]-3-[(Z)-2-ethoxycarbonyl-ethenylthio]-7-oxo-1-azabicyclo[3.2.0]hept-2-ene-2-carboxylate.

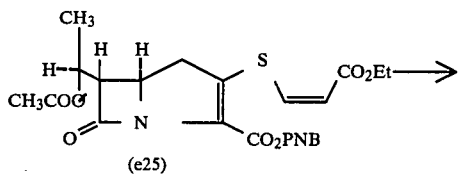

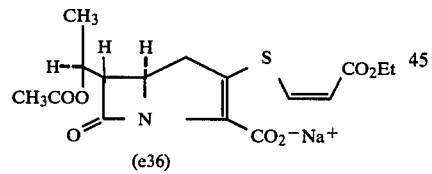

5% Pd on C catalyst (75 mg) was prehydrogented for 0.5 h in a mixture of dioxan (6 ml) and water (3 ml). A solution of the ester (e 25) (50 mg) in dioxan (1 ml) was introduced into the vessel and hydrogenation was continued for 4 h. Sodium bicarbonate (9 mg) was then added and the mixture was filtered over Celite washing the pad well with water. The solution was concentrated to ca. 10 ml and was then washed with ethyl acetate (30×3 ml) before again concentrating in vacuo to ca. 5 ml. The aqueous solution was chromatographed on a column of Biogel P2 (10×2.5 cm) and fractions containing the desired salt (e 36) were identified by u.v. These were combined and the solvent evaporated in vacuo, azeotroping out water with ethanol, and then ethanol with toluene, to afford the title compound (e 36) as an off-white solid (15 mg); $\lambda_{max}$. (H$_2$O) 323 nm; $\nu_{max}$. (KBr) 1770, 1735, 1695 and 1575 cm$^{-1}$.

EXAMPLE 26 p-Nitrobenzyl (5R,6S)-6-[(S)-1-acetoxyethyl]-3-ethylthio-7-oxo-1-azabicyclo[3.2.0]hept-2-ene-2-carboxylate.

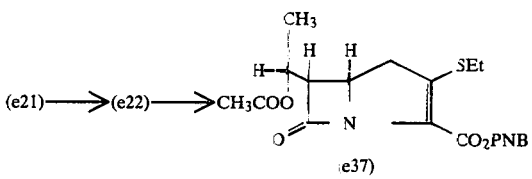

Step A

A solution of the derivative (e 21) (50 mg) in a mixture of dioxan (1 ml) and water (0.2 ml) was stirred with N-bromoacetamide (14 mg) for 15 min. at room temperature. CHCl$_3$ (20 ml) was added and the organic solution was washed with water, then dried (MgSO$_4$) and concentrated in vacuo to afford the thiol (e 22).

Step B

The product from step A was dissolved in DMF (0.5 ml) and the solution was treated with ethyl iodide (0.2 ml) and K$_2$CO$_3$ (15 mg) in the manner described in Example 1, step B. Work-up as therein described followed by chromatography on silica using 30% petrol in ethyl acetate to elute afforded the title-derivative (e 37) as an oil (17 mg); $\nu_{max}$. (CHCl$_3$) 1785, 1735 and 1700 cm$^{-1}$; $\lambda_{max}$. (EtOH) 320 and 267 nm.; δ (CDCl$_3$) 1.32 (3H, t, J 7.5 Hz, CH$_3$CH$_2$), 1.41 (3H, d, J 6.5 Hz, CH$_3$CH), 2.08 (3H, s, CH$_3$CO), 2.84 (2H, q, J 7.5 Hz, C$\underline{H}_2$S), 3.15 (2H, centre of ABX, 4-CH$_2$), 3.42 (1H, m, 6-CH), 4.09 (1H, m, 5-CH), ca. 5.25 (1H, m, CH$_3$C$\underline{H}$), 5.23 and 5.52 (each 1H, d, J 14 Hz, C$\underline{H}_2$Ar), 7.66 and 8.22 (each 2H, d, J 9 Hz, C$_6$H$_4$—NO$_2$). [M+, 434.1136. C$_{20}$H$_{22}$N$_2$O$_7$S requires 434.1145].

EXAMPLE 27 p-Nitrobenzyl (5R,6S)-3-(2-ethoxycarbonylethenylthio)-6-[(S)-1-hydroxyethyl]-7-oxo-1-azabicyclo[3.2.0]hept-2-ene-2-carboxylate.

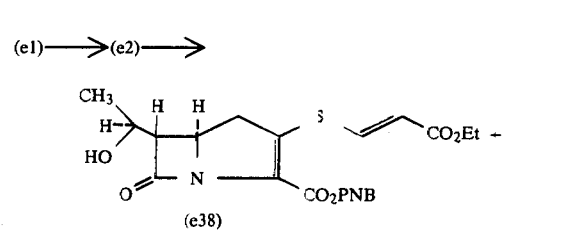

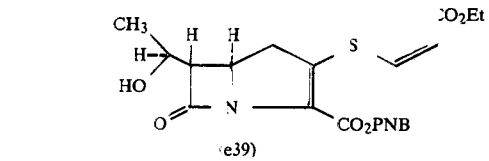

Step A

The ester (e 1) (250 mg) was converted into the thiol (e 2) by the method described in Example 17, step A.

Step B

The thiol (e 2) was treated with ethyl propiolate (110 mg) and anhydrous potassium carbonate (75 mg) in the manner described in Example 16, step B. Work-up and chromatography as described therein afforded two products.

The first product (20 mg) consisted mainly of the E-isomer of the title compound (e 38); $\nu_{max}$. (CHCl$_3$) 1780 and 1700 cm$^{-1}$; $\lambda_{max}$. (EtOH) 335 and 267 nm.; [M+, 462.1132; $C_{21}H_{22}N_2O_8S$ requires 462.1097].

The second, more polar component (48 mg) was the Z-isomer of the title compound (e 39), and was obtained as a crystalline solid; $\nu_{max}$. (KBr) 1775 and 1700 cm$^{-1}$; $\lambda_{max}$. (EtOH) 336 (21,600) and 2.64 (13,100) nm; δ (DMF-d$_7$) 1.26 (3H, t, J 7 Hz, CH$_3$CH$_2$) overlapping with 1.29 (3H, d, J 7 Hz, CH$_3$CH), ca. 3.25-3.80 (3H, m, 4-CH$_2$ and 6-CH), 4.18 (2H, q, J 7 Hz, OCH$_2$CH$_3$), ca. 4.05-4.50 (2H, m, 5-CH and CHCH$_3$), 5.24 (1H, d, J 4.5 Hz, OH), 5.38 and 5.62 (each 1H, d, J 14 Hz, CH$_2$Ar), 6.07 and 7.84 (each 1H, d, J 10 Hz, CH=CH), 7.87 and 8.28 (each 2H, d, J 9 Hz, C$_6$H$_4$—NO$_2$); [M+, 462.1089, $C_{21}H_{22}N_2O_8S$ requires 462.1093].

EXAMPLE 28 p-Nitrobenzyl (5R,6R)-3-ethylthio-6-[(S)-1-hydroxyethyl]-7-oxo-1-azabicyclo [3.2.0]hept-2-ene-2-carboxylate.

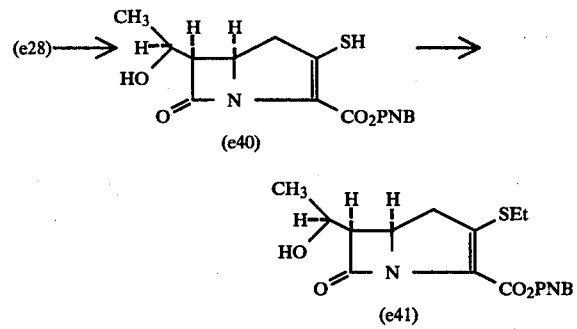

Step A

The ester (e 28) (500 mg) was treated with N-bromoacetamide (154 mg) in a mixture of dioxan (10 ml) and water (1.5 ml) using the methodology of Example 17, step A. The product contained the thiol (e 40).

Step B

A solution of the thiol (e 40) in DMF (7 ml) was stirred with ethyl iodide (0.5 ml) and anhydrous potassium carbonate (154 mg) for 25 min. at room temperature. Ethyl acetate (50 ml) was added and the solution was washed with water (50 ml) and brine (3×30 ml). The organic layer was dried (MgSO$_4$) and evaporated in vacuo to yield a crude product which was chromatographed on silica using 20% petrol in ethyl acetate to elute. The major product was the title compound (e 41), isolated as a foam (185 mg) which afforded crystals from ethyl acetate -petrol-ether m.p. 149°-151°; $\lambda_{max}$. (EtOH) 319 (12,400) and 265 nm (10,800); $\nu_{max}$. (CHCl$_3$) 1780 and 1700 cm$^{-1}$; δ (CDCl$_3$) 1.32 (3H, t, J Hz, CH$_3$CH$_2$), 1.39 (3H, d, J 6 Hz, CH$_3$CH), ca. 2.0 (1H, br, OH), 2.88 (2H, q, J 7 Hz, CH$_2$S), 3.08 (1H, dd, J 18 and 9.5 Hz, 4-CH$_a$), 3.53 (1H, dd, J 18 and 9 Hz, 4-CH$_b$), 3.56 (1H, dd, J 5.5 and 8.5 Hz, 6-CH), 4.0-4.35 (2H, m, 5-CH and CH$_3$CH), 5.20 and 5.49 (each 1H, d, J 14 Hz, CH$_2$Ar), 7.63 and 8.19 (each 2H, d, J 8.5 Hz, C$_6$H$_4$—NO$_2$).

EXAMPLE 29

Sodium (5R,6R)-3-ethylthio-6-[(S)-1-hydroxyethyl]-7-oxo-1-azabicyclo [3.2.0]hept-2-ene-2-carboxylate.

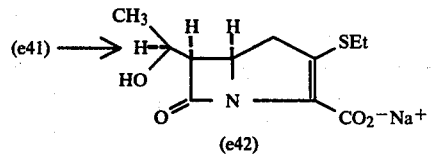

Using the method of Example 6, the ester (e 41) (95 mg) was hydrogenolysed to afford the sodium salt (e 42) as a white solid after chromatography on Biogel P2; $\lambda_{max}$. (H$_2$O) 300 nm; $\nu_{max}$. (KBr) 1745 and 1590 nm.

EXAMPLE 30

Sodium salt of p-nitrobenzyl (5R,6R)-3-[(Z)-ethoxycarbonylethenylthio]-6-[(S)-1-hydroxysulphonyloxyethyl]-7-oxo-1-azabicyclo[3.2.0-]hept-2-ene-2-carboxylate.

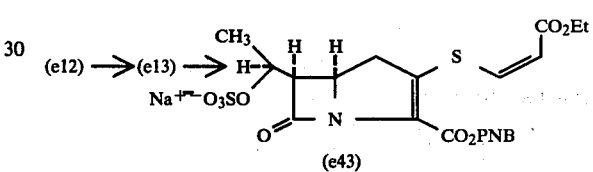

Step A

The monoquaternaryammonium salt (1.59 g) was converted into the thiol (e 13) by the method described in Example 21, step A.

Step B

The thiol (e 13) was treated with ethyl propiolate (350 mg) and potassium carbonate (247 mg) in an analogous manner to that described in Example 21, step B. Chromatography of the product as therein described afforded a foam (790 mg); $\nu_{max}$. (CHCl$_3$) 1780 and 1705 cm$^{-1}$.

Step C

The product from step B was dissolved in acetone (2.5 ml) and a solution of sodium iodide (131 mg) in acetone (1 ml) was added. The resulting white precipitate was filtered and washed with acetone and ether to afford the title compound (e 43) (400 mg); $\lambda_{max}$. (H$_2$O) 333 (20,300) and 270 (12,800 nm.) $\nu_{max}$. (KBr) 1775 and 1700 cm$^{-1}$; δ (DMF-d$_7$) 1.25 (3H, t, J 7 Hz, CH$_3$CH$_2$), 1.57 (3H, d, J 6.5 Hz, CH$_3$CH), ca. 3.10-4.0 (2H, m, 4-CH$_2$), 3.79 (1H, dd, J 5.5 and 11.5 Hz, 6-CH), 4.18 (2H, q, J 7 Hz, CH$_3$CH$_2$O), ca. 4.2-4.7 (2H, m, 5-CH and CHCH$_3$), 5.38 and 5.59 (each 1H, d, J 14 Hz, CH$_2$CO), 6.11 (1H, d, J 10 Hz, CH=CH S), 7.73 (1H, d, J 10 Hz, CH=CH.CO$_2$), 7.86 and 8.29 (each 2H, d, J 9 Hz, C$_6$H$_4$NO$_2$). The product contained ca. 10% of the corresponding E-isomer as seen from the signal at δ 6.26 (1H, d, J 15 Hz, SCH=CH).

EXAMPLE 31

Disodium salt of (5R,6R)-3-[(Z)-2-ethoxycarbonylethenylthio]-6-[(S)-1-hydroxysulphonyloxyethyl]-7-oxo-1-azabicyclo[3.2.0-]hept-2-ene-2-carboxylic acid.

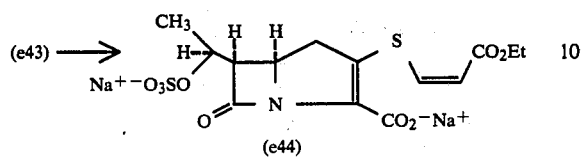

The ester (e 43) (348 mg) was hydrogenolysed as described in Example 22. After chromatography on Biogel P2 (20×3.5 cm) the aqueous solution containing the product was freeze-dried to afford the title disodium salt (e 44) (130 mg); $\nu_{max}$. (KBr) 1750, 1685, 1600 and 1570 cm$^{-1}$; $\lambda_{max}$. (H$_2$O) 324 nm.; δ (D$_2$O) 1.29 (3H, t, J 7 Hz, CH$_3$CH$_2$), 1.52 (3H, d, J 6 Hz, CH$_3$CH), 3.22 (1H, dd, J 10 and 17 Hz, 4-CH$_a$), 3.53 (1H, dd, J 9 and 17 Hz, 4-CH$_b$), 3.89 (1H, dd, J 5.5 and 9 Hz, 6-CH), 4.20 (2H, q, J 7 Hz, OCH$_2$CH$_3$), ca. 4.40 (1H, m, 5-CH), ca. 4.8 (1H, m, CH$_3$CH), 5.99 (1H, d, J 10 Hz, CH=CH.S). and 7.59 (1H, d, J 10 Hz, CH=CH.CO$_2$)

EXAMPLE 32

Sodium salt of p-nitrobenzyl (5R,6R)-3-ethylthio-6-[(S)-1-hydroxysulphonyloxyethyl]-7-oxo-1-azabicyclo[3.2.0]hept-2-ene-2-carboxylate.

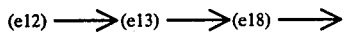

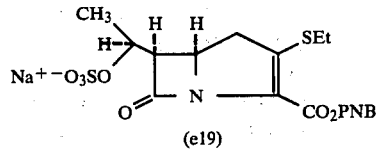

Step A

The derivative (e 12) (3.5 g) was converted into the thiol (e 13) by the method of Example 21, step A.

Step B

The thiol (e 13) was treated with ethyl iodide in the manner as described in Example 8, step B to afford the ethylthio-derivative (e 18) (1.48 g).

Step C

A solution of the quaternaryammonium compound (e 18) in acetone (15 ml) was mixed with a solution of sodium iodide (268 mg) in acetone (5 ml). A white solid crystallised out of the solution and this was filtered and washed with acetone and ether. The product (500 mg) consisted of the title compound (e 19); $\lambda_{max}$. (H$_2$O) 317 (12,470) and 273 nm (10,750); $\nu_{max}$. (KBr) 1770 and 1695 cm$^{-1}$; δ (DMF-d$_7$) 1.27 (3H, t, J 7.5 Hz, CH$_3$CH$_2$), 1.46 (3H, d, J 6 Hz, CH$_3$CH), 2.94 (2H, q, J 7.5 Hz, CH$_2$CH$_3$), 3.17 (1H, dd, J 19 and 9.5 Hz, 4-CH$_a$), 3.71 (1H, dd, J 5.5 and 11 Hz, 6-CH), 3.95 (1H, dd, J 19 and 8.5 Hz, 4-CH$_b$), ca. 4.3 (1H, m, 5-CH), ca. 4.55 (1H, m, CH$_3$CH), 5.31 and 5.55 (each 1H, d, J 13.5, CH$_2$AR) and 7.80 and 8.27 (each 2H, d, J 8.5 Hz, C$_6$H$_4$—NO$_2$).

EXAMPLE 33

Disodium salt of (5R,6R)-3-ethylthio-6-[(S)-1-hydroxysulphonyl-oxyethyl]-7-oxo-1-azabicyclo[3.2.0]hept-2-ene-2-carboxylic acid.

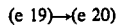

The ester (e19) (1.12 g) was hydrogenolysed with 5% Pd-C (1.5 g) in 30% aqueous dioxan (100 ml) using the procedure of Example 14. After work-up (190 mg NaHCO$_3$), as therein described, and chromatography on a column of Diaion HP20 (3.5×15 cm), eluting with water, fractions containing the product were combined and freeze-dried. The resulting solid (460 mg) consisted of the title disodium salt (e 20); $\lambda_{max}$. (H$_2$O) 300 nm (7900); $\nu_{max}$. (KBr) 1750 and 1595 cm$^{-1}$; [α]$_D$ (c.1, H$_2$O)+32°; δ (D$_2$O) 1.20 (3H, t, J 7 Hz, CH$_3$CH$_2$), 1.45 (3H, d, J 6.5 Hz, CH$_3$CH), 2.80 (2H, q, J 7 Hz, CH$_2$CH$_3$), 3.04 (1H, dd, J 10 and 18 Hz, 4-CH$_a$), 3.35 (1H, dd, J 9 and 18 hz, 4-CH$_b$), 3.78 (1H, dd, J 9 and 5 Hz, 6-CH), ca. 4.2 (1H, m, 5-CH), and ca. 4.75 (1H, m, CH$_3$CH).

EXAMPLE 34 p-Nitrobenzyl (5R,6S)-3-(2-p-nitrobenzyloxycarbonylaminoethylthio)-6-[(S)-1-hydroxyethyl]-7-oxo-1-azabicyclo[3.2.0]hept-2-ene-2-carboxylate.

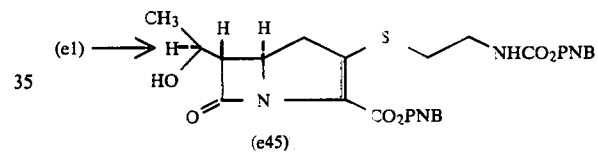

Step A

Following the procedure of Example 17, step A, the ester (e 1) (299 mg) was converted to the thiol (e 2).

Step B

The thiol (e 2) was treated with 2-p-nitrobenzyloxycarbonylaminoethyl bromide (135 mg) and potassium carbonate (62 mg) in DMF (3ml) in a similar way to that described in Example 1, step B. Work-up and chromatography on silica using ethyl acetate to elute afforded the title derivative (e 45) (31 mg); $\lambda_{max}$. (EtOH) 319 and 267 nm; $\nu_{max}$. (KBr) 1775 and 1700 cm$^{-1}$; δ (DMF-d$_7$) 1.28 (3H, d, J 6 Hz, CH$_3$CH), ca. 3.0–3.6 (7H, m, SCH$_2$CH$_2$N, 4-CH$_2$ and 6-CH), ca. 4.15 (2H, m, 5-CH and CH$_3$CH), 5.15. (1H, d, OH), 5.24 (2H, s, CH$_2$AR), 5.32 and 5.57 (each 1H, d, J 14 Hz, CH$_2$Ar), ca. 7.6–7.9 (5H, aromatic protons and NH) and 8.24 (4H, d, J 9 Hz, aromatic protons).

EXAMPLE 35

(5R,6S)-3-(2-Aminoethylthio)-6-[(S)-1-hydroxyethyl]-7-oxo-1-azabicyclo[3.2.0]hept-2-ene-2-carboxylic acid.

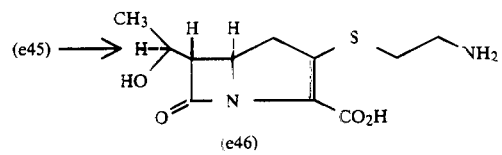

A mixture of the ester (e 34) (30 mg), 10% Pd on C (50 mg), dioxan (4ml), ethanol (0.3 ml), water (1 ml) and 0.05 M pH 7 phosphate buffer (1.3 ml) was shaken under a hyrogen atmosphere for 2 hours. The mixture was then filtered over Celite, washing with water (15 ml), and concentrated in vacuo to a volume of ca. 10 ml. The aqueous solution was washed with ethyl acetate ($\times 3$), and then concentrated in vacuo and chromatographed on a column of XAD-2 ($8 \times 1.2$ cm), eluting with water. Fractions containing the title zwitterion (e 46) were identified by the u.v. absorption at 297 nm.

EXAMPLE 36 p-Nitrobenzyl (5R,6R)-3-(2-p-nitrobenzyloxycarbonylaminoethylthio)-6-[(S)-1-hydroxyethyl]-7-oxo-1-azabicyclo[3.2.0]hept-2-ene-2-carboxylate.

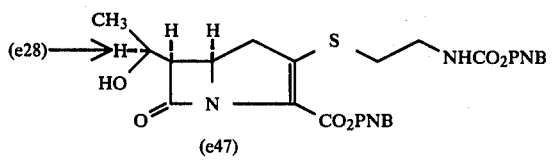

Using the procedure of Example 34 the ester (e 28) (500 mg) was converted into the title derivative (e 47), which could be crystallised from ethyl acetate-ether; $\nu_{max}$. (KBr) 1775 and 1740-1700 (br) cm$^{-1}$; $\lambda_{max}$. (EtOH) 315 (11,830) and 264 (18,740) nm.; δ (DMF-d$_7$) 1.31 (3H, d, J 6.5 Hz, CH$_3$CH), ca. 3.5-3.75 (7H, m, 4-CH$_2$, SCH$_2$CH$_2$N and 6-CH), 3.95-4.45 (2H, m, 5-CH and CHCH$_3$), 5.08 (1H, d, J 5 Hz, OH), 5.27 (1H, s, ArCH$_2$), 5.35 and 5.58 (each 1H, d, J 14 Hz, CH$_2$Ar), ca. 7.6-7.9 (5H, m, aromatic protons and NH) and 8.28 (4H, d, J 9 Hz, aromatic protons).

EXAMPLE 37

(5R,6R)-3-(2-Aminoethylthio)-6-[(S)-1-hydroxyethyl]-7-oxo-1-azabicyclo[3.2.0]hept-2-ene-2-carboxylate.

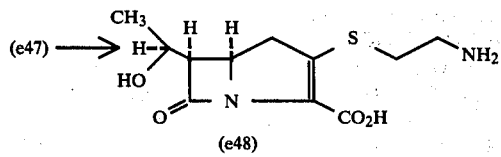

Using the process described in Example 35, the diester (e 47) (135 mg) was converted into the title compound (e 48) (11 mg); $\lambda_{max}$. (H$_2$O) 296 nm.

EXAMPLE 38

Sodium salt of p-nitrobenzyl (5R,6R)-3-(2-p-nitrobenzyloxycarbonylaminoethylthio)-6-[(S)-1-hydroxysulphonyloxyethyl]-7-oxo-1-azabicyclo[3.2.0]hept-2-ene-2-carboxylate.

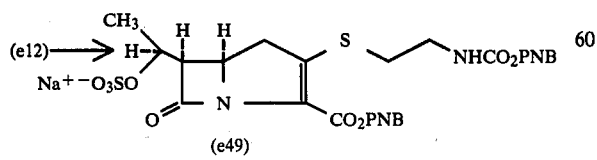

Steps A and B

Using processes analogous to those of Example 32 the ester (e 12) (1.25 g) was converted into the thiol (e 13) which was then alkylated with 2-p-nitrobenzyloxycarbonylaminoethyl bromide (300 mg).

Step C

The product was treated with sodium iodide (50 mg) in acetone (10 ml) and the resulting colloidal solution was chromatographed on silica gel using a gradient elution of CHCl$_3$ to 35% ethanol in chloroform. Fractions containing the product (e 49) were combined and concentrated in vacuo to afford the title compound as a solid (64 mg); $\lambda_{max}$. (H$_2$O) 310 sh and 274 nm; $\nu_{max}$. (KBr) 1775 and 1700 cm$^{-1}$.

EXAMPLE 39

Mono-sodium salt of (5R,6R)-3-(2-aminoethylthio)-6-[(S)-1-hydroxysulphonyloxyethyl]-7-oxo-1-azabicyclo[3.2.0]hept-2-ene-2-carboxylate.

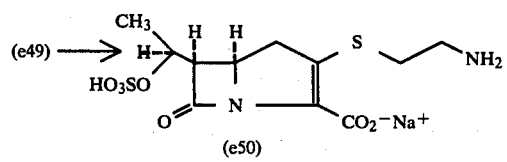

The method of Example 35 was used to hydrogenolyse the derivative (e 49) (60 mg) to afford an aqueous solution of the title compound (e 50); $\lambda_{max}$. (H$_2$O) 296 nm.

EXAMPLE 40 p-Nitrobenzyl (5R,6S)-3-(2-hydroxyethylthio)-6-[(S)-1-hydroxyethyl]-7-oxo-1-azabicyclo[3.2.0]hept-2-ene-2-carboxylate.

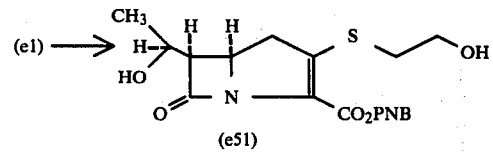

Employing the processes of Example 28, the ester (e 1) (300 mg) was converted into the derivative (e 51) by the use of 2-iodoethanol as the alkylating agent in step B. The title compound (e 51) was obtained as a white solid (67 mg); $\lambda_{max}$. (EtOH) 320 and 268 nm.; $\delta_{max}$. (KBr) 1765 and 1700 cm$^{-1}$; $\nu$(DMF-d$_7$) 1.29 (3H, d, J 6.5 Hz, CH$_3$CH), 3.06 (2H, t, J 7 Hz, SCH$_2$), ca. 3.35 (2H, m, centre of ABX, 4-CH$_2$), ca. 3.50 (1H, m, 6-CH), ca. 3.70 (2H, m, OCH$_2$), 3.95-4.40 (2H, m, 5-CH and CH$_3$CH), ca. 5.10 (2H, br, 2$\times$OH), 5.31 and 5.58 (each 1H, d, J 13.5 Hz, CH$_2$Ar) and 7.83 and 8.27 (each 2H, d, J 9 Hz, ArCH$_2$). [$\overline{M}$+, 408.1000. C$_{18}$H$_{20}$N$_2$O$_7$S requires 408.0989].

EXAMPLE 41

Sodium (5R,6S)-3-(2-hydroxyethylthio)-6-[(S)-1-hydroxyethyl]-7-oxo-1-azabicyclo[3.2.0]hept-2-ene-2-carboxylate.

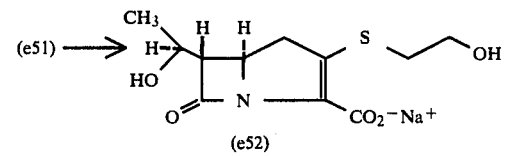

The ester (e 51) (60 mg) was hydrogenolysed in the manner of Example 6 to afford the title salt (e 52) (18 mg); $\lambda_{max}$. (H$_2$O) 302 nm.

EXAMPLE 42 p-Nitrobenzyl (5R,6R)-3-(2-hydroxyethylthio)-6-[(S)-1-hydroxyethyl]-7-oxo-1-azabicyclo[3.2.0.]hept-2-ene-2-carboxylate.

(e28) → (e53)

The methodology of Example 28 was used to convert the ester (e 28) (500 mg) into the derivative (e 53), via the thiol (e 40), employing 2-iodoethanol as the alkylating agent in step B. The product (e 53) was obtained as a foam (138 mg) which could be crystallised from ethyl acetate-ether; $\lambda_{max}$. (EtOH) 317 (11,500) and 266 (10,300) nm; $\nu_{max}$. (KBr) 1780, 1765 and 1690 cm$^{-1}$; $\delta$(DMF-d$_7$) 1.29 (3H, d, J 6 Hz, CH$_3$CH), 3.07 (2H, t, J 6 Hz, CH$_2$S), 3.2–3.85 (5H, m, 4-CH$_2$, 6-CH and OCH$_2$), ca. 3.95–4.45 (2H, m, 5-CH and CHCH$_3$), 5.05 (2H, br, 2×OH), 5.28 and 5.54 (each 1H, d, J 13 Hz, CH$_2$Ar) and 7.80 and 8.26 (each 2H, d, J 8.5 Hz, ArCH$_2$). [M$^+$, 408.1001, C$_{18}$H$_{20}$N$_2$O$_7$S requires 408.0991].

EXAMPLE 43

Sodium (5R,6R)-3-(2-hydroxyethylthio)-6-[(S)-1-hydroxyethyl]-7-oxo-1-azabicyclo[3.2.0]hept-2-ene-2-carboxylate.

(e53) → (e54)

Hydrogenolysis of the ester (e 53) (70 mg) in the manner described in Example 6 afforded the title sodium salt (e 54) (17 mg); $\lambda_{max}$. (H$_2$O) 298 nm; $\nu_{max}$. (KBr) 1750 and 1590 cm$^{-1}$.

EXAMPLE 44

Methyl (5R,6S)-3-p-bromophenacylthio-6-[(S)-1-hydroxyethyl]-7-oxo-1-azabicyclo[3.2.0]hept-2-ene-2-carboxylate.

(e55)

-continued (e56)

The derivative (e 55) (150 mg) was treated with (a) N-bromoacetamide and (b) p-bromophenacyl bromide using the method of Example 28 to afford the title compound (e 57) (42 mg); $\lambda_{max}$. (EtOH) 315 and 260 nm.; $\nu_{max}$. (CHCl$_3$) 1785, 1735 and 1700 cm$^{-1}$; $\delta$(CD Cl$_3$) 1.37 (3H, d, J 6.5 Hz, CH$_3$CH), 2.05 (3H, s, CH$_3$CO), 3.02 (1H, d, J 9 and 17 Hz, 4-CHa), 3.34 (1H, dd, J 9.5 and 17 Hz, 4-CH$_b$), 3.37 (1H, m, 6CH), 3.77 (3H, s, OCH$_3$), 4.08 (2H, s, CH$_2$S), ca. 4.05 (1H, m, 5-CH), 5.22 (1H, m, CH$_3$CH), 7.59 and 7.79 (each 2H, d, J 8 Hz, C$_6$H$_4$—Br). [M$^+$, 481.0203. C$_{20}$H$_{20}$NO$_6$SBr requires 481.0197].

A little of the product was recrystallised from ethyl acetate-petrol m.p. 160°-162°.

EXAMPLE 45 p-Nitrobenzyl (5R,6S)-6-[(S)-1-acetoxyethyl]-3-propargylthio-7-oxo-1-azabicyclo[3.2.0]hept-2-carboxylate.

(e21) → (e57)

Employing the methodology of Example 28, the ester (e 21) (500 mg) was converted into the derivative (e 57) by the use of proparagyl bromide in step B. The title compound (e 57) was obtained as an oil (235 mg); $\nu_{max}$. (CHCl$_3$) 1780, 1730 and 1700 sh; $\delta$(CDCl$_3$) 1.41 (3H, d, J 6.5 Hz, CH$_3$CH), 2.08 (3H, s, CH$_3$CO), 2.33 (1H, t, J 2 Hz, ≡CH), 3.05–3.65 (5H, m, CH$_2$C≡, 6-CH and 4CH$_2$), 4.12 (1H, dt, J ca. 3 and 9 Hz, 5-CH), ca. 5.25 (1H, m, CH$_3$CH), 5.22 and 5.50 (each 1H, d, J 14 Hz, CH$_2$AR), 7.63 and 8.21 (each 2H, d, J 9 Hz, CH$_2$Ar) [M$^+$, 444.0989. C$_{21}$H$_{20}$N$_2$O$_7$S requires 444.0979].

EXAMPLE 46

Sodium salt of p-nitrobenzyl (5R,6R)-3-propargylthio-6-[(S)-1-hydroxysulphonyloxyethyl]-7-oxo-1-azabicyclo [3.2.0]hept-2-ene-2-carboxylate.

(e12) → (e58)

By an anologous process to that described in Example 32, the mono-quaternaryammonium salt (e 12)(2.8 g) was transformed into the title mono sodium salt (e 58) which was obtained as a white solid (515 mg); $\lambda_{max}$. (H$_2$O) 310 (12,991) and 270 (11,257) nm.; $\nu_{max}$. (KBr)

1770 and 1700 cm$^{-1}$. $\delta$(DMF-d$_7$) 1.37 (3H, d, J 6 Hz, CH$_3$CH), ca. 2.95–3.40 (2H, m, 4-CHa and =CH), ca. 3.60–3.95 (4H, m, 4-CH$_b$, 6-CH and CH$_2$C≡), 4.15–4.60 (2H, m, 5-CH) and CHCH$_3$), 5.27 and 5.46 (each 1H, d, J 13 Hz, CH$_2$Ar), 7.69 and 8.23 (each 2H, d, J 9 Hz, ArCH$_2$); [α]$_D$(c.1, H$_2$O) −16°; [Found: C, 44.7; H, 3.6; N, 5.2%. C$_{19}$H$_{17}$N$_2$O$_9$S$_2$Na requires C, 45.2; H, 3.4; N, 5.5%].

EXAMPLE 47

Disodium salt of (5R,6R)-3-allylthio-6-[(S)-1-hydroxysulphonyloxy ethyl]-7-oxo-1-azabicyclo[3.2.0]hept-2-ene-2-carboxylic acid and disodium salt of (5R,6R)-3-propargylthio-6-[(S)-1-hydroxysulphonyloxyethyl]-7-oxo-1-azabicyclo[3.2.0]hept-2-ene-2-carboxylic acid.

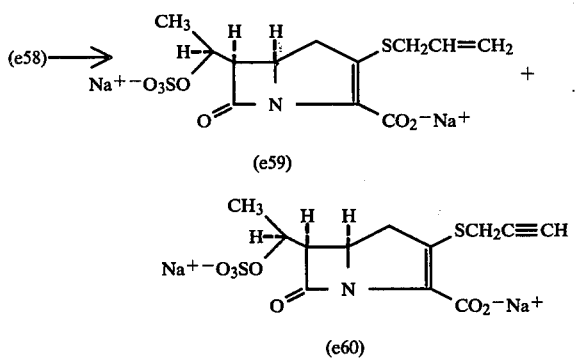

The ester (e 58) (400 mg) was hydrogenated over 5% Pd-C (500 mg) in the manner described in Example 6. The product, purified by chromatography on Biogel P2, consisted of a mixture of the title compounds (e 59) and (e 60) (130 mg) (ca. 4:1 by h. p. l. c. analysis); $\lambda_{max}$. (H$_2$O) 302 nm; $\nu_{max}$. (KBr) 1755 and 1595 cm$^{-1}$.

EXAMPLE 48 p-Nitrobenzyl (5R,6R)-3-allylthio-6-[(S)-1-hydroxyethyl]-7-oxo-1-azabicyclo[3.2.0]hept-2-ene-2-carboxylate.

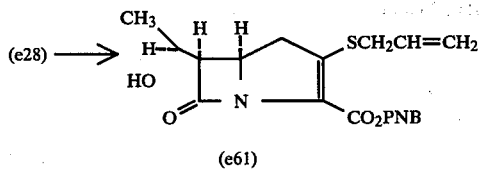

Using the process employed in Example 28 with allylbromide as the alkylating agent in step B, the ester (e 28) (300 mg) was converted to the title derivative (e 61) (115 mg) which was obtained as a crystalline solid; m.p. 137°–139°, [α]$_D$ (C. O. 5, CHCl$_3$) +24°, $\lambda_{max}$. (EtOH) 317 (12,772) and 266 (11,069) nm.; $\nu_{max}$. (CH$_2$Cl$_2$) 3590, 1780 and 1705 cm$^{-1}$; $\delta$(CDCl$_3$) 1.39 (3H, d, J 6 Hz, CH$_3$CH), 1.85 (1H, d, J 5.5 Hz, OH), 3.10 (1H, dd, J 9.5 and 19 Hz, 4-CHa), ca. 3.38–3.60 (4H, m, CH$_2$S, 4CH$_b$ and 6-CH) 4.0–4.45 (2H, m, 5-CH and CHCH$_3$), 5.10–5.60 (4H, m, ArCH$_2$ and =CH$_2$), 5.60–6.10 (1H, m, CH=), 7.63 and 8.19 (each 2H, d, J 9 Hz, C$_6$H$_4$—NO$_2$). [Found: C, 56.30; H, 4.99; N, 6.75%; M$^+$, 404.1050. C$_{19}$H$_{20}$N$_2$O$_6$S requires C, 56.42; H, 4.98; N, 6.93%; M$^+$, 404.1042].

EXAMPLE 49

Sodium (5R,6R)-3-propylthio-6-[(S)-1-hydroxyethyl]-7-oxo-1-azabicyclo[3.2.0.]hept-2-ene-2-carboxylate, and sodium (5R,6R)-3-allylthio-6-[(S)-1-hydroxyethyl]-7-oxo-1-azabicyclo[3.2.0]hept-2-ene-2-carboxylate.

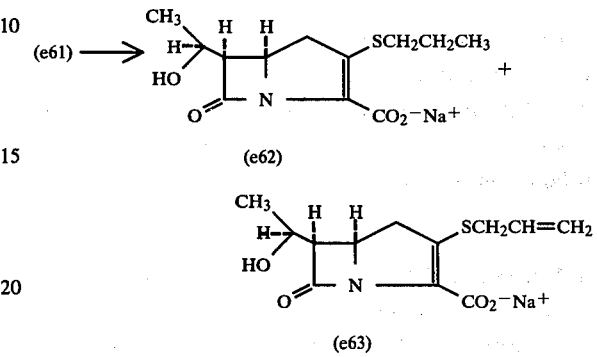

Hydrogenolysis of the ester (e 61) (80 mg) as described in Example 6 afforded a mixture (ca. 2:1 by h. p. l. c.) of the title derivatives (e 62) and (e 63); $\lambda_{max}$. (H$_2$O) 300 nm.

EXAMPLE 50

Sodium salt of p-nitrobenzyl (5R,6R)-3-allylthio-6-[(S)-1-hydroxysulphonyloxyethyl]-7-oxo-1-azabicyclo[3.2.0]hept-2-ene-2-carboxylate.

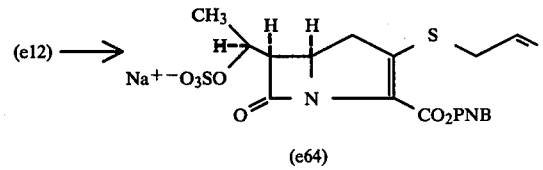

Conversion of compound (e 12) (2.8 g) to the derivative (e 64) was achieved by the process of Example 32, using allyl bromide as the alkylating agent in step B. The title compound (e 64) was obtained as a white solid (408 mg); $\lambda_{max}$. (EtOH) 317 (11,083) and 266 (9758) nm. $\nu_{max}$. (KBr) 1775, 1695 and 1260–1220 cm$^{-1}$; $\delta$(DMF-d$_7$) 1.47 (3H, d, J 6.5 Hz, CH$_3$CH), 3.22 (1H, dd, J 18 and 10 Hz, 4-CHa), 3.63 (2H, d, J 5.5 Hz, SCH$_2$), ca. 3.5–4.1 (2H, m, 6-CH and 4-CH$_b$), ca. 4.2–4.8 (2H, m, 5-CH and CHCH$_3$), 5.10–5.62 (4H, m, CH$_2$Ar and =CH$_2$), 5.75–6.20 (1H, m, HC=), 7.80 and 8.27 (each 2H, d, J 9 Hz, C$_6$H$_4$—NO$_2$).

EXAMPLE 51

Disodium salt of (5R,6R)-3-propylthio-6-[(S)-1-hydroxysulphonyloxyethyl]-7-oxo-1-azabicyclo[3.2.0]hept- 2-ene-carboxylic acid and disodium salt of (5R,6R)-3-allylthio-6-[(S)-1-hydroxysulphonyloxyethyl]-7-oxo-1-azabicyclo[3.2.0]hept-2-ene-2-carboxylic acid.

(e64) ⟶ (e59) +

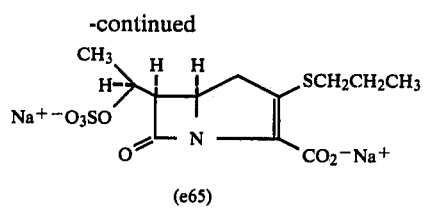

(e65)

Hydrogenolysis of the ester (e 64) (300 mg) by the method described in Example 6 afforded a mixture (ca. 3:1) of the title-compounds (e 65) and (e 59). An aqueous solution of the product was freeze-dried to give a solid (92 mg); $\lambda_{max}$. ($H_2O$) 302 nm.

EXAMPLE 52 p-Nitrobenzyl (5R,6R)-3-(3-p-nitrobenzyloxycarbonyl aminoethylthio)-6-[(S)-1-ethylthioethyl]-7-oxo-1-azabicyclo [3.2.0]hept-2-ene-2-carbxoylate.

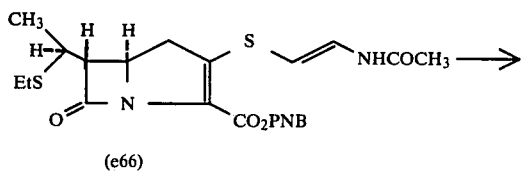

(e66)

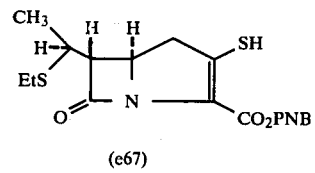

(e67)

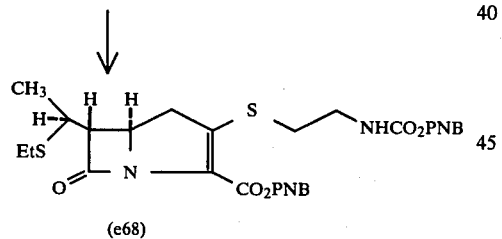

(e68)

The ethylthio-derivative (e 66) (270 mg) was treated with N-bromoacetamide (77 mg) as described in Example 17 step A to afford the thiol (e 67) Alkylation of (e 67) with 2-p-nitrobenzyloxycarbonylaminoethyl bromide (338 mg) in the manner of Example 34, step B, afforded the title derivative (e 68) (27 mg); $\lambda_{max}$. (EtOH) 319 nm.; $\nu_{max}$. ($CH_2Cl_2$) 3450, 1780 and 1705 sh cm$^{-1}$; δ(CDCl$_3$) 1.27 (3H, t, J 7 Hz, C$\underline{H}_3$CH$_2$), 1.39 (3H, d, J 6.5 Hz, C$\underline{H}_3$CH), 2.61 (2H, q, J 7 Hz, CH$_2$S), 2.90–3.60 (8H, m, 4-CH$_2$, SCH$_2$CH$_2$N, 6-CH and CHCH$_3$), 4.16 (1H, m, 5-CH), 5.20 (2H, s, CH$_2$Ar), ca. 5.25 (1H, br, NH), 5.23 and 5.52 (each 1H, d, J 14 Hz, ArCH$_2$), 7.48 and 7.64 (each 2H, d, J 14 Hz, aromatic protons) and 8.20 (4H, d, J 14 Hz, aromatic protons).

EXAMPLE 53 p-Nitrobenzyl (5R,6R)-3-(2-p-nitrobenzyloxycarbonylaminoethylthio)-6-[(R)-1-ethylthioethyl]-7-oxo-1-azabicyclo [3.2.0]hept-2-ene-2-carboxylate.

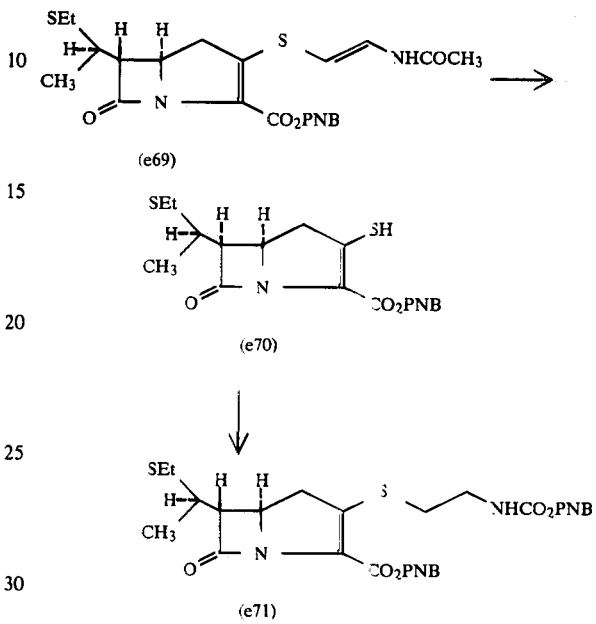

(e69)

(e70)

(e71)

Compound (e 69) (600 mg) was converted, via the thiol (e 70), into the derivative (e 71) by use of the methods outlined in Example 52. The title compound (e 71) was obtained as a crystalline solid (131 mg); m.p. 205–206°; $\lambda_{max}$. (EtOH) 319 (13,125) and 266 (21,235); $\nu_{max}$. (KBr) 1775 and 1725–1700 br cm$^{-1}$; δ(DMF-d$_7$) 1.22 (3H, t, J 7 Hz, CH$_3$CH$_2$), 1.41 (3H, d, J 6.5 Hz, CH$_3$CH), 2.64 (2H, q, J 7 Hz, CH$_2$S), ca. 3.0–3.6 (8H, m, 4CH$_2$, 6-CH, CH$_3$C$\underline{H}$ and SCH$_2$CH$_2$N), 4.17 (1H, m, 5-CH), 5.25 (2H, s, CH$_2$Ar), 5.33 and 5.58 (each 1H, d, CH$_2$Ar), ca. 7.65 (1H, br, NH), 7.67 and 7.82 (each 2H, d, J 9 Hz, aromatic protons) and 8.27 (4H, d, J 9 Hz, aromatic protons). [Found: C, 53.4; H, 4.8; N, 8.8%. C$_{28}$H$_{30}$N$_4$O$_9$S$_2$ requires C, 53.3; H, 4.8; N, 8.9%].

EXAMPLE 54

(5R,6R)-3-(2-Aminoethylthio)-6-[(R)-1-ethylthioethyl]-7-oxo-1-azabicyclo[3.2.0]hept-2-ene-2carboxylic acid.

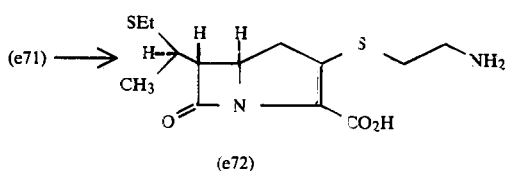

(e72)

A mixture of the thioether (e 71) (100 mg), 5% Pd on C (150 mg), 0.05 M, pH 7 phosphate buffer (5 ml) and dioxan (12 ml) was shaken in an atmosphere of hydrogen for 2 h. A further quantity (100 mg) of 5% Pd on C was added and hydrogenation was continued for a further 2.25 h. The mixture was filtered through Celite, washing the pad well with water (30 ml), and the filtrate was evaporated in vacuo to a volume of ca. 20 ml. The aqueous solution was washed with ethyl acetate (33 × 30

EXAMPLE 55 p-Nitrobenzyl (5R,6R)-3-methylthio-6-(1-ethylthioethyl)-7-oxo-1-azabicyclo[3.2.0]hept-2-ene-2-carboxylate.

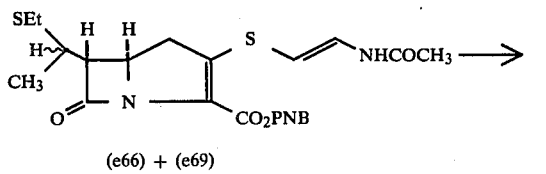

(e66) + (e69)

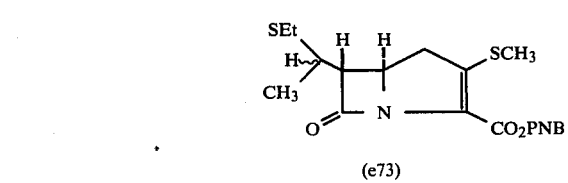

(e73)

A mixture of the esters (e 669 and ( 69) (200 mg) was converted into derivative (e 73) using the methodology of Example 17, with iodomethane as the alkylating agent in step B. The title compound (e 73) was obtained as a gum (50 mg); $\nu_{max}$. (CH$_2$Cl$_2$) 1780 and 1705 cm$^{-1}$; δ(CDCl$_3$) ca. 1.15–1.50 (3H, m, CH$_3$CH$_2$), 2.38 (3H, s, CH$_3$S), 2.59 (2H, q, J 7 Hz, SCH$_2$CH$_3$), ca. 2.85–3.60 (4H, m, 4-CH$_2$, 6-CH and CH$_3$CH), 4.15 (1H, m, 5-CH), 5.22 and 5.52 (each 1H, d, J 14 Hz, CH$_2$Ar), 7.66 and 8.22 (each 2H, d, J 9 Hz, ArCH$_2$) [M+, 422].

EXAMPLE 56 p-Nitrobenzyl (5R,6R)-3-[2-(pyrrol-1-yl)ethylthiol-6-[(S)-1-hydroxyethyl]-7-oxo-1azabicyclo[3.2.0]hept-2-ene-2-carboxylate.

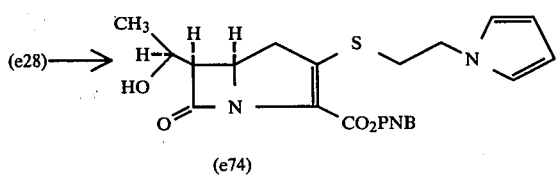

(e74)

In a reaction sequence similar to that of Example 28, the ester (e 28) (500 mg) was converted first to the thiol (e 40) which was alkylated with 1-(2-bromoethyl)pyrrole to afford the title compound (e 74). After purification on a silica column using 50% to 20% petrol-ethyl acetate to elute, compound (e 74) was obtained as a foam (78 mg); $\lambda_{max}$. (EtOH) 317 and 267 nj.; $\nu_{max}$. (CH$_2$Cl$_2$) 3580, 1780 and 1705 cm$^{-1}$; δ(CDCl$_3$) 1.36 (3H, d, J 6.5 Hz, CH$_3$CH), 1.91 (1H, br, OH), 2.53 (1H, dd, J 10 and 18 Hz, 4-CHa), 2.99 (1H, dd, J 9 and 18 Hz, 4-CH$_b$), 3.12 (2H, t, J 6.5 Hz, CH$_2$S), 3.48 (1H, dd, J 5.5 and 9 Hz, 6-CH), 4.10 (4H, m, CHCH$_3$, 5-CH and CH$_2$N), 5.19 and 5.48 (each 1H, d, J 14 Hz, CH$_2$N), 6.13 (2H, m, pyrrole β-CH), 6.67 (2H, pyrrole α-CH), 7.63 and 8.20 (each 2H, d, J 9 Hz, ArCH$_2$).

EXAMPLE 57

(5R,6R)-6-[(S)-1-Hydroxyethyl]-3-[2-(1-pyrrolyl)ethylthio]-7-oxo-1-azabicyclo[3.2.0]hept-2-ene-2-carboxylic acid.

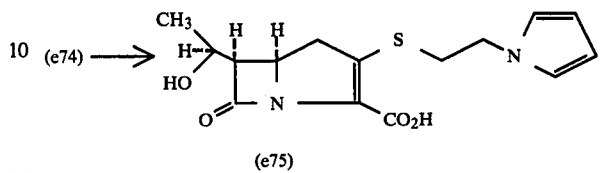

(e75)

The procedure of Example 20 was used to convert the ester (e 74) (70 mg) into the zwitterion (e 75) (13 mg). The product was purified by passing through a short column of Biogel P2 (5×2 cm) and freeze-drying the resulting solution. The title compound was obtained as a solid; $\lambda_{max}$. (H$_2$O) 300 nm.

EXAMPLE 58

Sodium salt of p-nitrobenzyl (5R,6R)-3-(2-pyrrol-1-ylethyl)-6-[(S)-1-hydroxysulphonyloxyethyl]-7-oxo-1-azabicyclo[3.2.0]hept-2-ene-2-carboxylate.

(e12) 

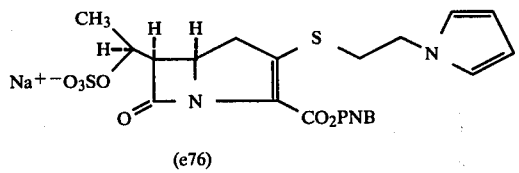

(e76)

Steps A and B

The method of Example 32 was used to convert the quaternaaryammonium salt (e 12) (2.8 g) into the thiol (e13), which was then alkylated with 1-(2-bromoethyl) pyrrole.

Step C

To a solution of the product from step B in acetone (10 ml) a solution of sodium iodide (124 mg) in acetone (5 ml) was added. The resulting solution was cooled and the solid formed (quaternary-ammonium iodide) was removed by fitration. The filtrate was concentrated in vacuo and then chromatographed on silica using a gradient elution of CHCL$_3$ to 30% EtOH-CHCL$_3$. The requisite fractions were combined and evaporated in vacuo to afford the title compound (e 76) (196 mg); $\lambda_{max}$. (H$_2$O) 316 and 273 nm; $\nu_{max}$. (KBr) 1765 and 1700 cm$^{-1}$; δ(DMF-d$_7$) 1.48 (3H, d, J 6.5 Hz, CH$_3$CH), ca. 3.2 (1H, m, 4-CHa), 3.28 (2H, m, SCH$_2$), ca. 3.7 (2H, m, 6-CH and 4-CH$_b$), 4.22 (2H, m, CH$_2$N), ca. 4.55 (2H, m, 5-CH and CHCH$_3$), 5.31 and 5.55 (each 1H, d, J 14 Hz, CH$_2$Ar) 6.00 (2H, m, pyrrole β-CH), 6.91 (2H, m, pyrrole 60 -CH), 7.80 and 8.27 (each 2H, d, J 9 Hz, ArCH$_2$).

EXAMPLE 59

Monosodium salt of
(5R,6R)-3-(2-Pyrrol-1-ylethylthio)-6-[(S)-1-hydroxysulphonyloxyethyl]-7-oxo-1-azabicyclo[3.2.0]hept-2-ene-2-carboxylic acid.

(e76) ⟶

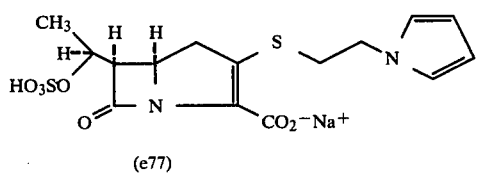

(e77)

The procedure of Example 20 was used to hydrogenolyse the ester (e 76) (150 mg). Chromatogrphy on Biogel P2 (10×2.5 cm) afforded the title compound (e 77) (46 mg). The solution was freeze-dried to give a solid; $\lambda_{max}$ (H$_2$O) 300 nm.; $\nu_{max}$ (KBr) 1750 and 1600 br cm$^{-1}$.

EXAMPLE 60 p-Nitrobenzyl (5R,6S)-3-[3-(p-nitrobenzyloxycarbonylamino)propylthio]-6-[(S)-1-hydroxyethyl]-7-oxo-1-azabicyclo[3.2.0.-]hept-2-ene-2-carboxylate

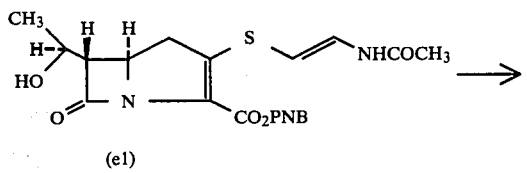

(e1)

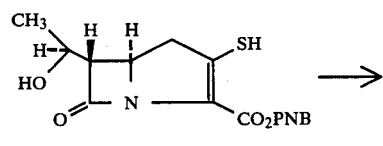

(e2)

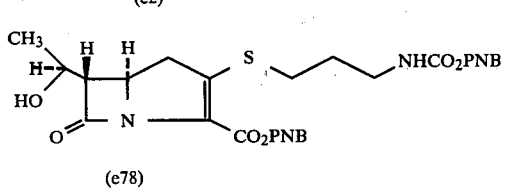

(e78)

The ester (e1, 500 mg, 1.119 mM) was dissolved in 1,4-dioxan (10 ml) containing water (30 drops). A solution of N-bromoacetamide (155 mg, 1.119 mM) in 1,4-dioxan was then added and the solution stirred at room temperature for 4.5 minutes. Chloroform (50 ml) was added and the organic phase was washed with pH 7.0, 0.05 M phosphate buffer, saturated sodium chloride solution and dried over anhydrous magnesium sulphate. Filtration and removal of the solvent at reduced pressure yielded the crude thiol (e2) as a gum, $\nu_{max}$ (CHCL$_3$) 1780, 1730 and 1700 cm$^{-1}$.

The crude thiol was dissolved in dry dimethylformamide (10 ml) and stirred at room temperature for 25 minutes with anhydrous potassium carbonate (155 mg, 1.119 mM) and 3-(N-p-nitrobenzyloxycarbonyl) amino-1-bromopropane (355 mg; 1.119 mM). Ethyl acetate was added and the organic solution washed with water, saturated sodium chloride solution and dried over anhydrous magnesium sulphate. After filtration the solvent was removed at reduced pressure to give a pale yellow oil, which was chromatographed over silica gel (50 gm). Elution with 5% ethanol/chloroform afforded the title compound (e78) (155 mg) as a white solid. This solid was digested in diethyl ether and collected by filtration (145 mg), m.p. 164°-168° C., [4 $_{max}$ (KBr) 3420, 1765, 1700 1608 cm$^{-1}$; $\lambda_{max}$(EtOH) 320 nm (68 m 13,400) and 266 nm (68 m 20,050); 67 $_H$ (d$^7$-DMF) 1.28 (3H, d, J 6.6Hz, CH$_3$CH), 1.86 (2H, m, CH$_2$CH$_2$CH$_2$), 2.99 (2H, t, SCH$_2$) 3.24 (t, CH$_2$NH), 3.33 (d, 4-CH$_2$), 3.49 (1H, t, J$_{6-8}$ 4.3Hz, 6-CH), 4.05 (1H, m, CH$_3$CH), 4.24 (1H, dt, J $_{4-5}$ 9.0Hz, J$_{5-6}$ 2.9Hz, 5-CH), 5.12 (1H, d, J$_{OH-8}$ 4.6Hz, OH), 5.23–5.65 (4H, S+AB, 2×CH$_2$Ar), 7.39 (1H, broad resonance, NH), 7.68 (2H, d, Ar protons), 7.82 (2H, d, Ar protons), 8.25 (4H, d, Ar protons); m/e 286, 153, 136, no M$^+$; (Found; C, 53.71; H, 4.60; N, 9.07 C$_{27}$H$_{28}$N$_4$O$_{10}$S requires; C, 53.99; H, 4.70; N 9.33%).

EXAMPLE 61

(5R,6S)-3-(3-Aminopropylthio)-6-[(S)-1-hydroxyethyl]-7-oxo-1-azabicyclo[3.2.0.]hept-2-ene-2-carboxylic acid

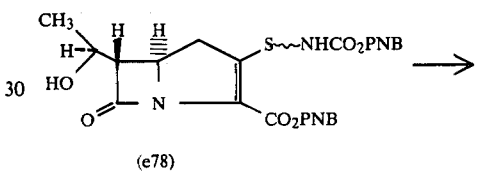

(e78)

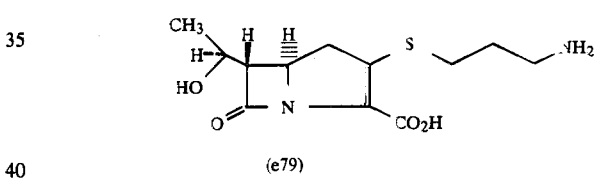

(e79)

A solution of the ester (e78), 130 mg) in 1,4-dioxan (15 ml), water (4.5 ml), ethanol (1.35 ml) and 0.05 M pH7.0 phosphate buffer (6 ml) was hydrogenated in the presence of 10% palladium on carbon (200 mg) for 2 hours. The suspension was then filtered over Celite, washing with water (20 ml). The filtrate was concentrated to about 20 ml and washed with ethyl acetate (3×25 ml). The aqueous solution was further concentrated to about 10 ml and chromatographed on a column of XAD-2, eluting with water. Fractions containing the product were combined to yield the title compound (e79) (14.5 mg) in aqueous solution, 80 $_{max}$ (H$_2$O) 299nm.

EXAMPLE 62 p-Nitrobenzyl (5R,6R)-3-[3-(p-nitrobenzyloxycarbonylamino)propylthio]-6-[(S)-1-hydroxyethyl]-7-oxo-1-azabicyclo[3.2.0.-]hept-2-ene-2-carboxylate

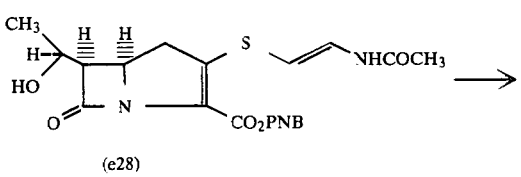

(e28)

-continued

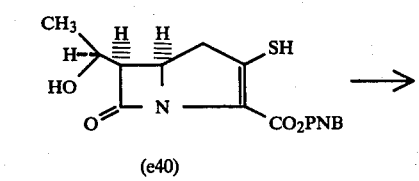
(e40)

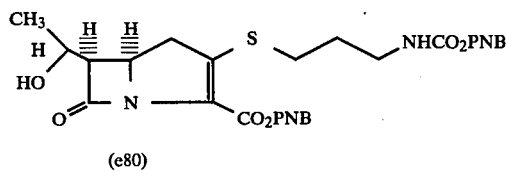
(e80)

The title compound (e80) was prepared as a white solid in 20% yield from the ester (e28), adopting the procedure described in example 60., m.p. 104°–106° C. (ethyl acetate/diethyl ether), $\lambda_{max}$ (EtOH) 317 nm (Em 12,360) 266 nm (Em 18,890); $\lambda_{max}$ (KBr) 3410, 1770, 1700, 1608 cm$^{-1}$; $\delta_H$ (d$_7$-DMF) 1.31 (3H, d, J 6Hz, CH$_3$CH), 1.9 (2H, m, CH$_2$ CH$_2$CH$_2$), 3.03 (2H, t, SCH$_2$), 3.22 (t, CH$_2$NH), 3.5 (d, 4-CH$_2$), 3.6 (m, 1H, 6-CH), 3.9–4.5 (2H, m, 8-CH+5-CH), 5.06 (1H, d, J 6Hz, OH), 5.23 (2H, S, CH$_2$Ar), 5.44 (2H, AB, CH$_2$Ar), 7.4 (1H, broad resonance, NH), 7.6–8.4 (8H, 2xAB, 2xAr); m/e 555, 514, 286, 136, no M$^+$.

EXAMPLE 63

(5R,6R)-3-(3-Aminopropylthio)-6-[(S)-1-hydroxyethyl]-7-oxo-1-azabicyclo[3.2.0]hept-2-ene-2-carboxylic acid

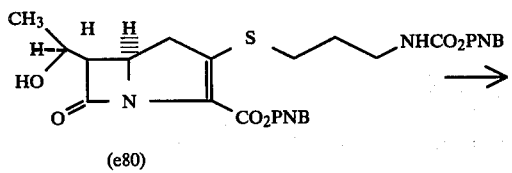
(e80)

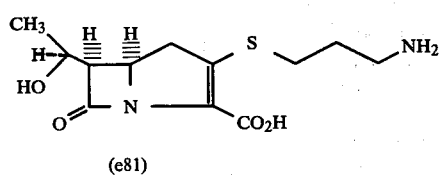
(e81)

The ester (e80) was hydrogenolysed as in example 61 to yield (5R,6R)-3-(3-aminopropylthio)-6-[(S)-1-hydroxyethyl]-7-oxo-1-azabicyclo[3.2.0]hept-2-ene-2-carboxylic acid (e81) in 26% yield as an aqueous solution (based on Em 8,500). A sample was freeze dried to give a pale yellow fluffy solid, $\lambda_{max}$ (H$_2$O) 292 nm, $\nu_{max}$ (KBr) 3420, 1750, 1600 (broad) cm$^{-1}$.

EXAMPLE 64 p-Nitrobenzyl (5R,6S)-3-(p-nitrobenzyloxycarbonylmethylthio)-6-[(S)-1-hydroxyethyl]-7-oxo-1-azabicyclo[3.2.0]hept-2-ene-2-carboxylate

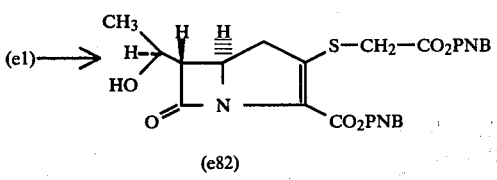
(e82)

The diester (e82) (150 mg) was prepared as a pale yellow solid by reaction of the ester (e1) (500 mg) with N-bromoacetamide, followed by p-nitrobenzyl bromoacetate, utilising the procedure outlined in example 60., $\lambda_{max}$ (EtOH) 309 nm, 265 nm (Em 15,355); $\nu_{max}$ (KBr) 3500, 1765, 1737, 1700, 1608, 1550, 1520 1348 cm$^{-1}$; $\delta_H$ (d$_7$-DMF) 8.26 (d)+7.79 (t, 8H, aromatic protons), 5.40 (s+q, 4H, CH$_2$Ar protons); 5.20 (1H, d, OH), 4.0–4.5 (s+m, 4H, CH$_2$CO$_2$PNB+5-CH+8-CH), 1.27 (3H, d, CH$_3$CH); m/e 513, 286, 168, 136, 78 no M$^+$.

EXAMPLE 65

Disodium (5R,6S)-3-(carboxymethylthio)-6-[(S)-1-hydroxyethyl]-7-oxo-1-azabicyclo[3.2.0]hept-2-ene-2-carboxylate

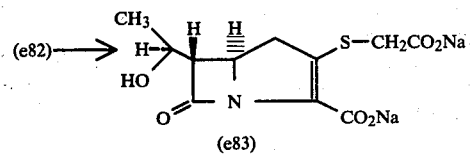
(e83)

5% Palladium on carbon catalyst (75 mg) was shaken with hydrogen in 30% aqueous 1,4-dioxan (10 ml) at ambient pressure and temperature for 0.5 hours. A solution of the diester (e82).(50 mg) in 1,4-dioxan (10 ml) was added and the hydrogenation was continued for a further 3.5 hours. Sodium bicarbonate (15 mg) was added and the mixture was filtered through Celite, washing well with water (30 ml). The filtrate was concentrated at reduced pressure to approximately 20 ml and washed with ethyl acetate (3×25 ml). The aqueous solution was further concentrated to about 10 ml and chromatographed on a column of Biogel P-2, eluting with water. Fractions containing the title compound (e83) were identified by the chromophore at $\lambda_{max}$ (H$_2$O) 300 nm in the U.V. spectrum. These fractions were combined and freeze dried to afford a pale yellow solid (9 mg).

EXAMPLE 66 p-Nitrobenzyl
(5R,6R)-3-(p-nitrobenzyloxycarbonylmethylthio)-6-
[(S)-1-hydroxyethyl]-7-oxo-1-azabicyclo
[3.2.0]hept-2-ene-2-carboxylate (e28) ⟶ 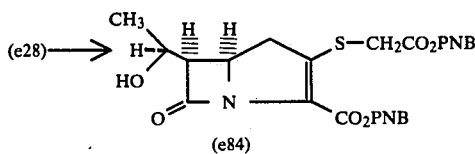
(e84)

The diester (e84) (179 mg) was prepard as a pale yellow solid by reaction of the thiol (e40), derived from the ester (e28) (500 mg) with p-nitrobenzyl bromoacetate, by the method described in example 60., $\lambda_{max}$ (EtOH) 311 nm (Em 11,120), 265 nm (Em 21,197); $\nu_{max}$ (KBr) 3490, 1760 (broad), 1700, 1608, 1555, 1520, 1348 cm$^{-1}$., $\delta_H$ (d$_7$-DMF) 8.26 (d) and 7.78 (t, 8H, aromatic protons), 5.40 (4H, q+s, CH$_2$Ar protons), 5.03 (1H, d, OH), 3.8– 4.5 (s+m, 4H, CH$_2$CO$_2$PNB+5-CH+8-CH), 3.2–3.8 (m, 4-CH$_2$+6-CH), 1.28 (3H, d, CH$_3$CH); m/e 513, 471, 286, 227, 168, 136, no M+.

EXAMPLE 67

Disodium
(5R,6R)-3-(carboxymethylthio)-6-[(S)-1-hydroxyethyl]-
7-oxo-1-azabicyclo[3.2.0]hept-2ene-2-carboxylate (e84) ⟶ 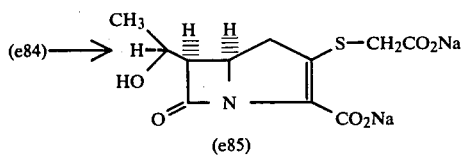
(e85)

The diester (e84) (75 mg) was hydrogenolysed in the manner described in example 65. Biogel P-2 column chromatography, eluting with water afforded the title compound (e85) (15 mg) in aqueous solution, $\lambda_{max}$ (H$_2$O) 300 nm. A sample was freeze dried to yield a yellow solid.

EXAMPLE 68 p-Nitrobenzyl
(5R,6S)-3-[2-(2-methyl-4-nitroimidazol-1-yl)ethylthio]-
6-[(S)-1-hydroxyethyl]-7-oxo-1-azabicyclo
[3.2.0]hept-2-ene-2-carboxylate (e1) ⟶ 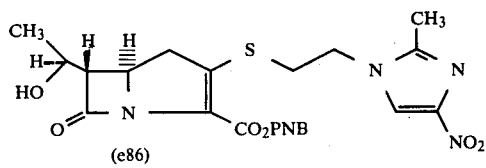
(e86)

The title compound (e86) (97 mg) was prepared as a pale yellow solid by reacting the thiol (e2), derived from ester (e1) (500 mg) with 1-(β-bromoethyl)-2-methyl-4-nitroimidazole, adopting the procedure described in example 60., $\lambda_{max}$ (EtOH) 308 nm (Em 15449), 270 nm (Em 13539), $\nu_{max}$ (KBr) 3420, 1770, 1700, 1605, 1540, 1520, 1345, 1333, 750, 738 cm$^{-1}$, $\delta_H$ (d$_7$-DMF) 8.39 (1H, S, imidazole-CH), 8.25 (2H, d, aromatic protons), 7.81 (2H, d, aromatic protons), 5.44 (2H, q, CH$_2$Ar), 5.14 (1H, d, OH), 4.43 (2H, t, CH$_2$N), (dt, 5-DH), 2.43 (3H, s, imidazole-CH$_3$), 1.27 (3H, d, CH$_3$CH), m/e 330.0846 (C$_{16}$H$_{14}$ N$_2$O$_6$ requires 330.0852), 286, 187, 128, 44, no M+.

EXAMPLE 69

(5R,6S)-3-[2-(2-Methyl-4-amino-imidazol-1-yl)ethylthio]-6-(S)-1-hydroxyethyl]-7-oxo-1-azabicyclo
[3.2.0]hept-2-ene-2-carboxylic acid (e86) ⟶ 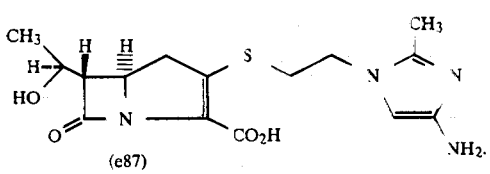
(e87)

Hyrogenolysis of the ester (e86) (70 mg) by the procedure described in example 61 gave an aqueous solution containing (5R,6S)-3-[2-(2-methyl-4:amino-imidazol-1-yl)ethylthio)-6-[(S)-1-hydroxyethyl]-7-oxo-1-azabicyclo [3.2.0]hept-2-ene-2-carboxylic acid (87). A sample was freeze-dried to yield a white fluffy solid, $\lambda_{max}$ (H$_2$O) 298 nm, $\nu_{max}$ (KBr) 3400, 1750, 1665, 1590, 1400 cm$^{-1}$.

EXAMPLE 70 p-Nitrobenzyl
(5R,6R)-3-[2-(2-methyl-4-nitroimidazol-1-yl)ethylthio]-
6-[(S)-1-hydroxyethyl]-7-oxo-1-azabicyclo
[3.2.0]hept-2-ene-2-carboxylate (e28) ⟶ 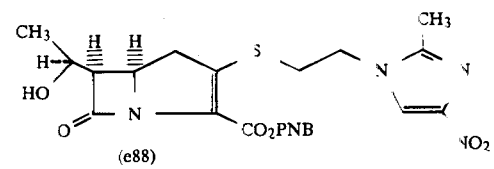
(e88)

The title compound (e88) (85 mg) was prepared as a white solid by reacting the thiol (e40), derived from the ester (e28) (500 mg) with 1-(β-bromoethyl)-2-methyl-4-nitroimidazole, utilising the procedure described in example 60., $\lambda_{max}$ (EtOH) 308 nm (Em 11,961), 275 nm, $\nu_{max}$ (CHBr$_3$) 3400, 1775, 1698, 1605, 1563, 1540, 1515, 1320, 743 cm$^{-1}$., $\delta_H$ (d$_7$-DMF) 8.39 (1H, S, imidazole CH), 8.27 (2H, d, aromatic protons), 7.81 (2H, S, aromatic protons), 5.45 (2H, q, CH$_2$Ar protons), 4.45 (2H, t, CH$_2$N), 2.44 (3H, S, imidazole CH$_3$), 1.30 (3H, d, CH$_3$CH).

EXAMPLE 71

(5R,6R)-3-[2-(2-Methyl-4-amino-imidazol-1-yl)
ethylthio]-6-[(S)-1-hydroxyethyl]-7-oxo-1-azabicyclo
[3.2.0]hept-2-ene-2-carboxylic acid (e88) ⟶

-continued

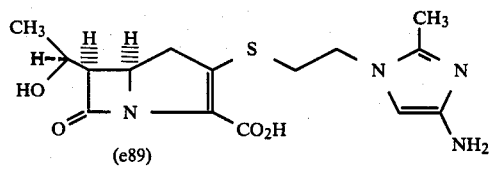
(e89)

Hydrogenolysis of the ester (e88) (60 mg) by the procedure described in example 61 gave an aqueous solution containing the title compound (e89), $\lambda_{max}$ (H$_2$O) 297 nm, $\nu_{max}$ (KBr) 3400, 1750, 1665, 1595, 1400 cm$^{-1}$.

EXAMPLE 72 p-Nitrobenzyl (5R,6S)-3-[2-(2-methyl-5-nitroimidazol-1-yl)ethylthio]-6-[(S)-1-hydroxyethyl]-7-oxo-1-azabicyclo[3.2.0.]hept-2-ene-2-carboxylate

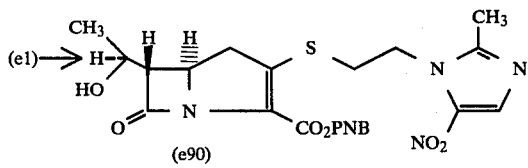
(e90)

p-Nitrobenzyl (5R,6S)-3-[2-methyl-5-nitroimidazol-1-yl)ethylthio]-6-[(S)-1-hydroxyethyl]-7-oxo-1-azabicyclo[3.2.0.]hept-2-ene-2-ene-2-carboxylate (e90) (40 mg) was obtained as a white solid by the reaction of the thiol (e2) derived from the ester (e1) (250 mg) with 1-($\beta$-bromoethyl)-2-methyl-5-nitroimidazole, utilising the procedure described in example 60., $\lambda_{max}$ (EtOH) 312 nm (Em 17925), 268 nm (Em 12885), $\nu_{max}$ (KBr) 3420, 1775, 1700, 1608, 1520, 1332, 1350, 1365, 742 cm$^{-1}$., $\delta_H$ (d$_7$-DMF) 8.25 (2H, d, aromatic protons), 8.01 (1H, s, imidazole CH), 7.80 (2H, d, aromatic protons), 5.44 (2H, q, CH$_2$Ar), 5.19 (1H, d, OH), 4.68 (2H, t, CH$_2$N), 4.2 (2H, dt+m, 5-CH+8-CH), 2.52 (3H, s, imidazole CH$_3$), 1.28 (3H, d, CH$_3$CH).

EXAMPLE 73

(5R,6S)-3-[2-(2-Methyl-5-amino-imidazol-1-yl)ethylthio]-6-[(S)-1-hydroxyethyl]-7-oxo-1-azabicyclo[3.2.0.]hept-2-ene-2-carboxylic acid

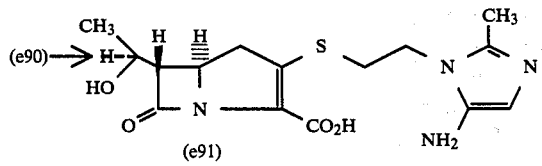
(e91)

The title compound (e91) was obtained in aqueous solution by hydrogenolysis of the ester (e90) (30 mg). The procedure outlined in example 61 was followed with the exception that hydrogenolysis time was extended to 3 hours. A sample was freeze dried to yield a white fluffy solid, $\lambda_{max}$ (H$_2$O) 297 nm, $\nu_{max}$ (KBr) 3400, 1750, 1600, 1390 cm$^{-1}$.

EXAMPLE 74 p-Nitrobenzyl (5R,6R)-3-[2-(2-methyl-5-nitroimidazol-1yl)ethylthio]-6-[(S)-1-hydroxyethyl]-7-oxo-1-azobicyclo[3.2.0.]hept-2-ene-2-carboxylate (e28) 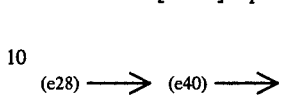 (e40) ⟶

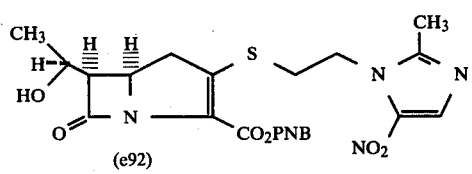
(e92)

The title compound (e92) (77 mg) was prepared by reaction of the thiol (e40) derived from the ester (e28) (227 mg) with 1-($\beta$-bromoethyl)-2-methyl-5-nitroimidazole, adopting the procedure described in example 60., $\lambda_{max}$ (EtOH) 310 nm (Em 17677), 266 nm (Em 12969), $\nu_{max}$ (KBr) 3400, 1770, 1700, 1608, 1520, 740 cm$^{-1}$, $\delta_H$ (CDCl$_3$) 8.18 (2H, d, aromatic protons), 7.93 (1H, S, imidazole CH-CH+8-CH), 2.9–3.8 (5H, m, SCH$_2$+6-CH+4-CH$_2$), 2.62 (1H, broad res., OH), 2.49 (3H, S, imidazole CH$_3$), 1.38 (3H, d, CH$_3$CH).

EXAMPLE 75

(5R,6R)-3-[2-(2-Methyl-5-aminoimidazol-1-yl)ethylthio]-6-[(S)-1-hydroxyethyl]-7-oxo-1-azabicyclo[3.2.0]hept-2-ene-2-carboxylic acid

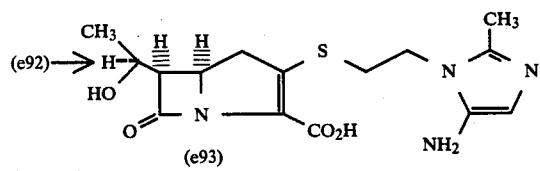
(e93)

The title compound (e93) was prepared by hydrogenolysis of the ester (e92) (30 mg), following the procedure outlined in Example 61 with the exception that the hydrogenation time was extended to 4 hours. Freeze drying gave a white solid, $\lambda_{max}$ (H$_2$O) 293 nm, $\nu_{max}$ (KBr) 3400, 1750, 1600, 1390 cm$^{-1}$.

EXAMPLE 76 p-Nitrobenzyl (5R,6S)-3-[(2-p-nitrobenzyloxycarbonylaminothiazol-4-yl)methylthio]-6-[(S)-1-hydroxyethyl]-7-oxo-1-azabicyclo[3.2.0]hept-2-ene-2-carboxylate (e1)  (e2) ⟶

-continued

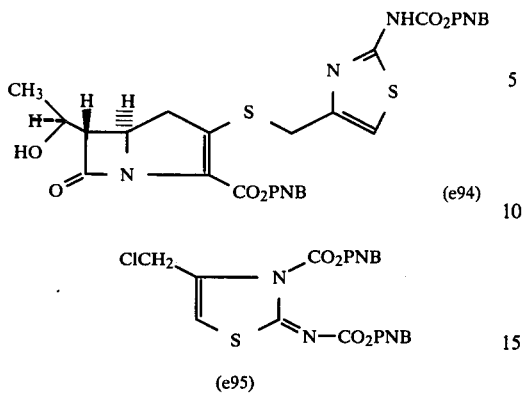

Following the procedure described in example 60, reaction of the thiol (e2) derived from the ester (e1) (250 mg) with the intermediate (e 95) gave, after silica gel column chromatography, p-nitrobenzyl (5R,6S)-3-[(2-p-nitrobenzyloxycarbonylaminothiazol-4-yl)methylthio]-6-[(S)-1-hydroxyethyl]-7-oxo-1-azabicyclo[3.2.0-]hept-2-ene-2-carboxylate (e94) (70 mg) as a white solid, $\lambda_{max}$ (EtOH) 319 nm (Em 12286), 263 nm (Em 25630), $\nu_{max}$ (KBr) 3440, 1770, 1730, 1700, 1610, 1550, 1520, 1350, 1335 cm$^{-1}$, $\delta_H$ (d$_7$-DMF) 7.7–8.4 (8H, m, aromatic protons), 7.13 (1H, s, thiazole C$\underline{H}$), 5.1–5.7 (s+q+broad d, 2×C$\underline{H}_2$Ar+O$\underline{H}$5H), 4.0–4.4 (4H, s+m, SC$\underline{H}_2$+5-C$\underline{H}$+8C$\underline{H}$), 3.2–3.9 (m, 4-C$\underline{H}_2$+6-C$\underline{H}$), 1.28 (3H, d, C$\underline{H}_3$CH).

EXAMPLE 77 p-Nitrobenzyl (5R,6R)-3-[2-p-nitrobenzyloxycarbonylaminothiazol-5-yl)methylthio]-6-[(S)-1-hydroxyethyl]-7-oxo-1-azabicyclo[3.2.0.]hept-2-ene-2-carboxylate (e28) ——→ (e40) ——→

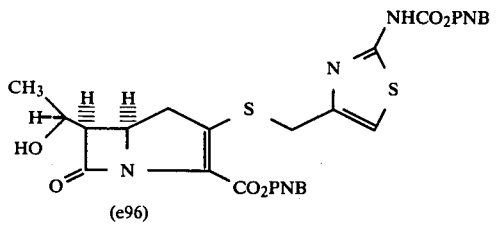

The title compound (e96) (95 mg) was prepared as a white solid by reaction of the ester (e28) (250 mg) with N-bromoacetamide, followed by intermediate (e95), utilising the procedure outlined in example 60., $\lambda_{max}$ (EtOH) 316 nm (Em 13729), 264 nm (Em 27411), $\nu_{max}$ (KBr) 3400 (broad), 3390 (sharp), 3080, 3110, 1770, 1730, 1695, 1608, 1550, 1345, 1330 cm$^{-1}$, $\delta_H$ (d$_7$-DMF) 7.7–8.4 (8H, m, aromatic protons), 7.15 (1H, s, thiazole-CH), 5.2–5.6 (4H, s +q, C$\underline{H}_2$Ar protons), 4.0–4.4 (s +m, 4H, SC$\underline{H}_2$+5-C$\underline{H}$+8-C$\underline{H}$), 1.32 (3H, D, C$\underline{H}_3$CH).

EXAMPLE 78

(5R,6R)-3-[(2-Aminothiazo-4-yl)methylthio]-6-[(S)-1-hydroxyethyl]-7-oxo-1-azabicyclo[3.2.0]hept-2-ene-2-carboxylic acid

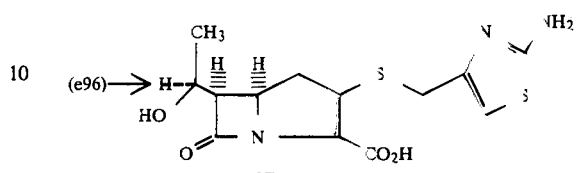

The ester (e96) (60 mg) was hydrogenolysed, as in example 61 to yield (5R,6R)-3-[(2-aminothiazol-4-yl)methylthio]-6-[(S)-1-hydroxyethyl]-7-oxo-1-azabicyclo[3.2.0] hept-2-ene-2-carboxylic acid (e97) (22 mg based on Em 8,500 at $\lambda_{max}$ 297 nm in the u.v. spectrum) as an aqueous solution. A white fluffy solid was obtained on freeze-drying, $\lambda_{max}$ (H$_2$O) 261 nm, 297 nm, $\nu_{max}$ (KBr) 3400, 1750, 1590 cm$^{-1}$.

EXAMPLE 79 p-Nitrobenzyl (5R,6S)-3-[2-phenylthiazol-4-yl)methylthio]-6-[(S)-1-hydroxyethyl]-7-oxo-1-azabicyclo[3.2.0]hept-2-ene-2-carboxylate (e1) ——→ (e2) ——→

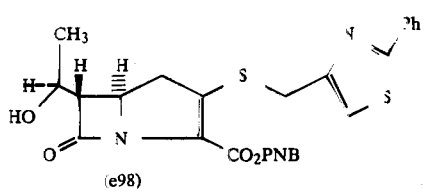

p-Nitrobenzyl (5R,6S)-3-[(2-phenylthiazol-4-yl)methylthio]-6-[(S)-1-hydroxyethyl]-7-oxo-1-azabicyclo [3.2.0.]hept-2-ene-2-carboxylate (e98) (148 mg) was prepared as a pale yellow solid by reaction of the thiol (e2) derived from the ester (e1) (500 mg) with 2-phenyl-4-iodomethyl thiazole, following the procedure described in example 60, $\lambda_{max}$(EtOH) 290 nm (Em 23059); $\nu_{max}$ (KBr) 3500, 1768, 1698, 1608, 1546, 1519, 1348, 1332 cm$^{-1}$; $\delta_H$ ($\delta_7$-DMF) 7.4–8.4 (10H, m, p-nitrobenzyl protons+phenyl protons+thiazole-C$\underline{H}$), 5.44(2H, q, C$\underline{H}_2$Ar), 5.19(1H, d, O$\underline{H}$, disappears on D$_2$O), 4.42(2H,s,SC$\underline{H}_2$), 4.0–4.4 (2H,m, 5-C$\underline{H}$+8-C$\underline{H}$), 3.5(3H,m,4-C$\underline{H}_2$+6-C$\underline{H}$), 1.29(3H,d,C$\underline{H}_3$CH); m/e 537 (relative intensity) (1%), 491 (10), 451 (10), 286 (30), 207 (55), 175 (100), 136 (20).

EXAMPLE 80 p-Nitrobenzyl(5R,6R)-3-[(2-phenylthiazol-4-yl)methylthio]-6-[(S)-1-hydroxyethyl]-7-oxo-1-azabicyclo[3.2.0-]hept-2-ene-2-carboxylate (e28) ——→ (e40) ——→

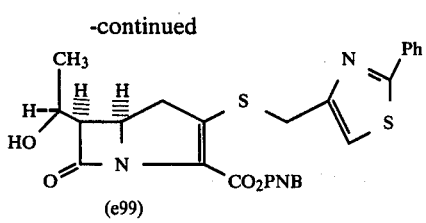

(e99)

The title compound (e99) (198 mg) was obtained as a white solid by reaction of the thio (e40), derived from the ester (e28) (500 mg) with 2-phenyl-4-iodomethyl-thiazole, adopting the procedure described in example 60, $\lambda_{max}$ (EtOH) 300 nm (Em 21622); $\nu_{max}$ (KBr) 3430, 3110, 1776, 1695, 1608, 1550, 1520, 1348, 1328 cm$^{-1}$; $\delta_H$($\delta_7$-DMF)7.4–8.3(10H,m,p-nitrobenzyl protons+phenyl protons+thiazole-CH), 5.43(2H,q,CH$_2$Ar), 5.10(1H,d,OH, disappears on D$_2$O), 4.47(2H,s,SCH$_2$), 3.9–4.4(2H,m,5-CH+8-CH), 3.5–3.9(3H,m,4-CH$_2$+6-CH), 1.33(3H,d,CH$_3$CH), m/e (relative intensity) 451 (4%), 418(2), 286(50), 207(100), 174(95), 104(55), 71(72).

EXAMPLE 81

(5R,6R)-3-[(2-Phenylthiazol-4-yl)methylthio]-6-[(S)-1-hydroxyethyl]-7-oxo-1-azabicyclo[3.2.0]hept-2-ene-2-carboxylic acid

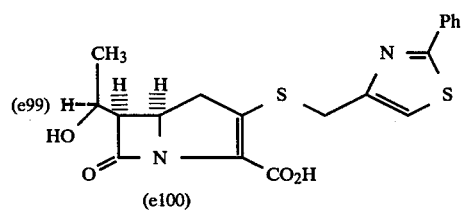

(e100)

The ester (e99) (90 mg) was hydrogenolysed, as in example 61, to yield the title compound (e100) (19 mg based on Em 17,000 at $\lambda_{max}$ 297 nm in the u.v. spectrum) as an aqueous solution. A white fluffy solid was obtained on freeze-drying, $\lambda_{max}$(H$_2$O) 297 nm, $\nu_{max}$(KBr) 3400, 1740, 1600 cm$^{-1}$.

EXAMPLE 82 p-Nitrobenzyl (5R)-3-(ethylthio)-6-Z-ethylidene-7-oxo-1-azabicyclo[3.2.0]hept-2-ene-2-carboxylate

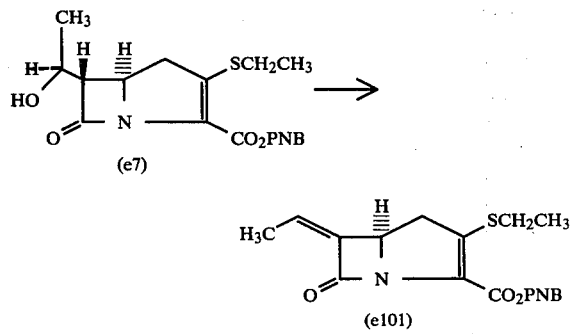

p-Nitrobenzyl (5R,6S)-3-ethylthio-6-[(S)-1-hydroxyethyl]-7-oxo-1-azabicyclo[3.2.0]hept-2-ene-2-carboxylate (e7) (237 mg; 0.60 mM) was dissolved in dry tetrahydrofuran (40 ml) and cooled to 0° C. Triphenylphosphine (634 mg; 2.42 mM) was added with stirring, followed by a solution of diethylazodicarboxylate (421 mg; 2.42 mM) in dry tetrahydrofuran (20 ml). The solution was then allowed to reach room temperature and stirred for a further 20 minutes. The solvent was removed at reduced pressure and the residue partitioned between ethyl acetate and water. The organic layer was washed with an additional volume of water, saturated sodium chloride solution and dried over anhydrous magnesium sulphate. Filtration and removal of the solvent at reduced pressure gave the crude ethylidene as an orange oil. This oil was dissolved in the minimum volume of ethyl acetate/hexane (1:1) and chromatographed over silica gel (20 mg), eluting with a gradient of 50–75% ethyl acetate/hexane. The title ethylidene derivative (e101) was obtained as a pale yellow oil (185 mg). Trituration with diethyl ether/hexane gave a pale yellow solid (130 mg), $\nu_{max}$ (CHBr$_3$) 1755, 1700, 1605 cm$^{-1}$.

EXAMPLE 83 p-Nitrobenzyl(5R,6R)-3-ethylthio-6-ethyl-7-oxo-1-azabicyclo[3.2.0]hept-2-ene-2-carboxylate (e102) and p-nitrobenzyl(5R,6S)-3-ethylthio-6-ethyl-7-oxo-1-azabicyclo[3.2.0]hept-2-ene-2-carboxylate (e103)

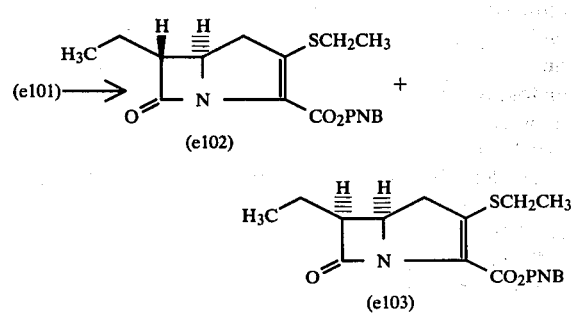

A solution of the ethylidene (e101) (127 mg) in tetrahydrofuran (10 ml) was cooled to −10° C. To this stirred solution was added a solution of sodium borohydride (52 mg) in 0.05M pH 7.0 phosphate buffer (2 ml). The reaction mixture was allowed to reach 5° C. and stirring continued at this temperature for 1 hour. Ethyl acetate (50 ml) was added and the organic solution washed with water, saturated sodium chloride solution, and dried over anhydrous magnesium sulphate. Filtration and removal of the solvent at reduced pressure gave the crude product as a pale yellow oil. Silica gel column chromatography eluting with 1:1 hexane/ethyl acetate gave a mixture of p-nitrobenzyl(5R,6R)-3-ethylthio-6-ethyl-7-oxo-1-azabicyclo[3.2.0]hept-2-ene-2-carboxylate (e102) and P-nitrobenzyl(5R,6S)-3-ethylthio-6-ethyl-7-oxo1-azabicyclo[3.2.0]hept-2-ene-2-carboxylate (e103) (ratio 5:1 by h.p.l.c.) as a colourless oil (14 mg). Crystallisation from ether/hexane gave a white solid, m.pt. 108°–115° C., $\lambda_{max}$ (EtOH) 322 nm, 267 nm, $\nu_{max}$ (CHBr$_3$) 1775, 1700, 1605, 1550 cm$^{-1}$,$\delta_H$ (CDCl$_3$), 1.06(3H,t,CH$_3$CH$_2$CH), 1.32(3H,t,CH$_3$CH$_2$S), 1.85(2H,m,CH$_3$CH$_2$CH), 2.85(2H,q,SCH$_2$), 2.7–3.3(3H, m,4-CH$_2$+6-CH), 3.97(1H,dt,5-CH), 5.37(2H,q,CH$_2$Ar), 7.65(2H, d,aromatic protons), 8.21(2H,d,aromatic protons), m/e (relative intensity) 376.1098(32%; C$_{18}$H$_{20}$N$_2$O$_5$S requires 376.1091), 347(2), 306(100), 273(20), 255(10), 170(20), 136(35), 126(40).

EXAMPLE 84

Sodium(5R,6R)-3-ethylthio-6-ethyl-7-oxo-1-azabicyclo[3.2.0]hept-2-ene-2-carboxylate

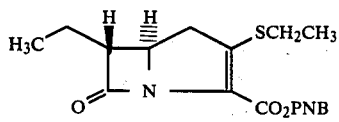 (e102)

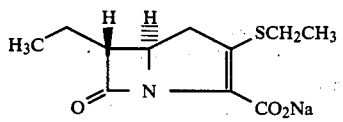 (e104)

5% Palladium on carbon catalyst (15 mg) was shaken with hydrogen in 30% aqueous 1,4-dioxan (5 ml) at ambient pressure and temperature for 20 minutes. A solution of the ester (e102) (10 mg) in 1,4-dioxan (5 ml) was added and hydrogenation was continued for a further 3.5 hours. Sodium bicarbonate (3 mg) was added and the suspension filtered through Celite, washing well with water (25 ml). The filtrate was concentrated at reduced pressure to approximately 15 ml and washed with ethyl acetate (3×25 ml). The aqueous solution was further concentrated to about 10 ml and column chromatographed over Biogel P-2, eluting with water. Fractions containing sodium (5R,6R)-3-ethylthio-6-ethyl-7-oxo-1-azabicyclo[3.2.0]hept-2-ene-2-carboxylate (e104) were identified by the chromophore at $\lambda_{max}$ ($H_2O$) 300 nm in the u.v. spectrum and combined (1.6 mg based on Em 8,000).

What we claim is:

1. A compound of the formula (I):

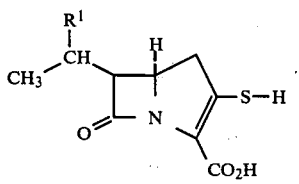 (I)

and salts and esters thereof wherein $R^1$ is $OSO_3H$ or a salt or an alkyl ester thereof of 1 to 4 carbon atoms, or $OCONHR^3$, wherein $R^3$ is alkyl of 1 to 6 carbon atoms, benzyl unsubstituted or substituted by alkoxy of 1 to 3 carbon atoms, fluoro, bromo, chloro or nitro; or phenyl unsubstituted or substituted by alkyl of 1 to 3 carbon atoms, alkoxy of 1 to 3 carbon atoms, fluoro, bromo, chloro or nitro: with the proviso that when $R^1$ is $OSO_3H$ or a salt or alkyl ester thereof of 1 to 4 carbon atoms, the C-6 and C-5 hydrogen atoms are cis.

2. A compound according to claim 1 in the form of a pharmaceutically acceptable salt or in-vivo hydrolysable ester.

3. A compound according to claim 1 wherein $R^1$ is $OSO_3H$ or a pharmaceutically acceptable salt thereof or a methyl or ethyl ester thereof, or $OCONHR^3$, wherein $R^3$ is alkyl of 1 to 4 carbon atoms, benzyl, phenyl or p-nitrobenzyl.

4. A compound according to claim 1 wherein $R^1$ is in the form of a quaternary ammonium salt of the sulphate moiety.

5. A compound according to claim 1 wherein $R^1$ is benzyldimethyl-n-hexadecylammonium or the methyl or ethyl ester of the moiety $OSO_3H$.

6. A compound according to claim 1 in the form of a cleavable ester at the $C_2$ carboxyl.

7. A compound according to claim 1 in the form of an ester cleavable by hydrogenolysis, hydrolysis or biological methods 8. A compound according to claim 1 in the form of an ester, wherein the ester moiety is of the sub-formula (a), (b), (c) or (d):

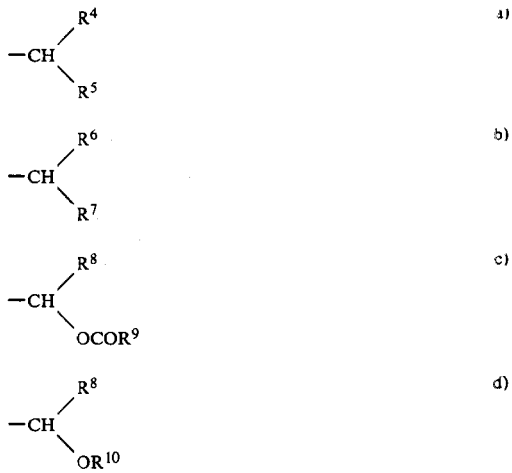

wherein $R^4$ is hydrogen, alkyl of up to 3 carbon atoms, alkenyl of up to 3 carbon atoms or alkynyl of up to 3 carbon atoms; $R^5$ is hydrogen or methyl; $R^6$ is phenyl unsubstituted or substituted by fluoro, chloro, bromo, nitro, methyl or methoxy; $R^7$ is hydrogen or phenyl unsubstituted or substituted by fluoro, chloro, bromo, nitro, methyl or methoxy; $R^8$ is hydrogen or methyl; $R^9$ is alkyl of 1 to 4 carbon atoms, phenyl or alkoxy of 1 to 4 carbon atoms; or $R^8$ is joined to $R^9$ to form a phthalidyl, dimethylphthalidyl or dimethoxyphthalidyl moiety; and $R^{10}$ is alkyl of 1 to 4 carbon atoms, phenyl, chlorophenyl, nitrophenyl or $CHR^4R^5$ is phenacyl or bromophenacyl.

9. A compound according to claim 8 wherein $R^4$ is hydrogen, methyl, ethyl, vinyl or ethenyl; $R^5$ is hydrogen; $R^6$ is phenyl, p-bromophenyl, p-methoxyphenyl or p-nitrophenyl; $R^7$ is hydrogen; $R^9$ is methyl, t-butyl or ethoxy or is joined to $R^8$ to form a phthalidyl, dimethylphthalidyl or dimethoxyphthalidyl moiety; and $R^{10}$ is methyl.

10. A compound according to claim 8 wherein the ester moiety is methyl or ethyl.

11. A compound according to claim 8 wherein the ester moiety is benzyl or p-nitrobenzyl.

12. A compound according to claim 8 wherein the ester moiety is acetoxymethyl, pivaloyloxymethyl, α-ethoxycarbonyloxymethyl or phthalidyl.

13. A compound according to claim 8 wherein the ester moiety is methoxymethyl.

14. A compound according to claim 8 wherein the ester moiety is p-nitrobenzyl or phthalidyl.

15. A compound according to claim 1 in the form of an alkali metal salt or alkaline earth metal salt 16. A compound according to claim 1 in the form of the sodium or potassium salt.

17. A compound according to claim 1 wherein $R^1$ is a pharmaceutically acceptable salt of $OSO_3H$ and the compound is in the form of a di-pharmaceutically acceptable salt.

18. A salt according to claim 17 in the form of the di-sodium or di-potassium salt.

19. The compound according to claim 1 which is

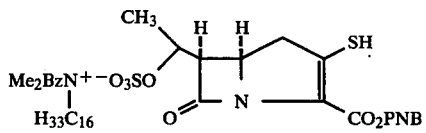

wherein PNB is p-nitrobenzyl.

20. A pharmaceutical composition useful for treating bacterial infections in humans and animals which comprises an antibacterially effective amount of a compound of the formula

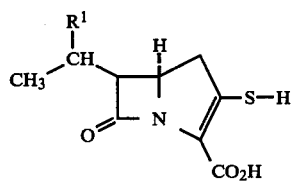

or a pharmaceutically acceptable salt or pharmaceutically acceptable ester thereof wherein $R^1$ is $OSO_3H$ or a salt or an alkyl ester thereof of 1 to 4 carbon atoms, $[OR^2, SR^3, OCOR^2, OCO_2R^3]$ or $OCONHR^3$, wherein $R^3$ is alkyl of 1 to 6 carbon atoms, benzyl unsubstituted or substituted by alkoxy of 1 to 3 carbon atoms, fluoro, bromo, chloro or nitro; or phenyl unsubstituted or substituted by alkyl of 1 to 3 carbon atoms, alkoxy of 1 to 3 carbon atoms, fluoro, bromo, chloro or nitro: with the proviso that when $R^1$ is $OSO_3H$ or a salt or alkyl ester thereof of 1 to 4 carbon atoms, the C-6 and C-5 hydrogen atoms are cis, in combination with a pharmaceutically acceptable carrier.

21. A composition according to claim 20 wherein the compound is in the form of a pharmaceutically acceptable salt or in-vivo hydrolyzable ester.

22. A composition according to claim 20 wherein $R^1$ is $OSO_3H$ or a pharmaceutically acceptable salt thereof or a methyl or ehtyl ester thereof, or $OCONHR^3$, wherein $R^3$ is alkyl of 1 to 4 carbon atoms, benzyl, phenyl or p-nitrobenzyl.

23. A composition according to claim 20 wherein the compound is in the form of an ester, wherein the ester moiety is of the sub-formula (a), (b), (c) or (d):

$$-CH\genfrac{}{}{0pt}{}{R^4}{R^5} \quad (a)$$

$$-CH\genfrac{}{}{0pt}{}{R^6}{R^7} \quad (b)$$

$$-CH\genfrac{}{}{0pt}{}{R^8}{OCOR^9} \quad (c)$$

-continued $$-CH\genfrac{}{}{0pt}{}{R^8}{OR^{10}} \quad (d)$$

wherein $R^4$ is hydrogen, alkyl of up to 3 carbon atoms, alkenyl of up to 3 carbon atoms or alkynyl of up to 3 carbon atoms; $R^5$ is hydrogen or methyl; $R^6$ is phenyl unsubstituted or substituted by fluoro, chloro, bromo, nitro, methyl or methoxy; $R^7$ is hydrogen or phenyl unsubstituted or substituted by fluoro, chloro, bromo, nitro, methyl or methoxy; $R^8$ is hydrogen or methyl; $R^9$ is alkyl of 1 to 4 carbon atoms, phenyl or alkoxy of 1 to 4 carbon atoms; or $R^8$ is joined to $R^9$ to form a phthalidyl, dimethylphthalidyl or dimethoxyphthalidyl moiety; and $R^{10}$ is alkyl of 1 to 4 carbon atoms, phenyl, chlorophenyl, nitrophenyl or $CHR^4R^5$ is phenacyl or bromophenacyl.

24. A composition according to claim 22 wherein $R^4$ is hydrogen, methyl, ethyl, vinyl or ethenyl; $R^5$ is hydrogen; $R^6$ is phenyl, p-bromophenyl, p-methoxyphenyl or p-nitrophenyl; $R^7$ is hydrogen; $R^9$ is methyl, t-butyl or ethoxy or is joined to $R^8$ to form a phthalidyl, dimethylphthalidyl or dimethoxyphthalidyl moiety; and $R^{10}$ is methyl.

25. A composition according to claim 22 wherein the ester moiety is methyl or ethyl.

26. A composition according to claim 22 wherein the ester moiety is benzyl or p-nitrobenzyl.

27. A composition according to claim 22 wherein the ester moiety is acetoxymethyl, pivaloyloxymethyl, α-ethoxycarbonyloxymethyl or phthalidyl.

28. A composition according to claim 22 wherein the ester moiety is methoxymethyl.

29. A composition according to claim 22 wherein the ester moiety is p-nitrobenzyl or phthalidyl.

30. A composition according to claim 20 wherein the compound is in the form of an alkali metal salt or alkaline earth metal salt 31. A composition according to claim 20 wherein the compound is in the form of the sodium or potassium salt.

32. A composition according to claim 20 wherein $R^1$ is a pharmaceutically acceptable salt of $OSO_3H$ and the compound is in the form of a di-pharmaceutically acceptable salt.

33. A composition according to claim 32 wherein the salt is in the form of the di-sodium or di-potassium salt.

34. A composition according to claim 20 wherein the compound is

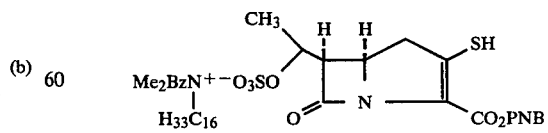

wherein PNB is p-nitrobenzyl.

35. A method of treating bacterial infections in humans and animals which comprises administering to a human or animal in need thereof an antibacterially effective amount of a compound of the formula (I):

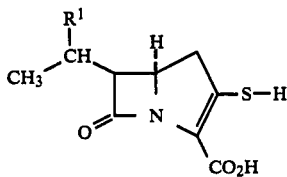

(I)

or a pharmaceutically acceptable salt or pharmaceutically acceptable ester thereof wherein $R^1$ is $OSO_3H$ or a salt or an alkyl ester thereof of 1 to 4 carbon atoms, or $OCONHR^3$, wherein $R^3$ is alkyl of 1 to 6 carbon atoms, benzyl unsubstituted or substituted by alkoxy of 1 to 3 carbon atoms, fluoro, bromo, chloro or nitro; or phenyl unsubstituted or substituted by alkyl of 1 to 3 carbon atoms, alkoxy of 1 to 3 carbon atoms, fluoro, bromo, chloro or nitro: with the proviso that when $R^1$ is $OSO_3H$ or a salt or alkyl ester thereof of 1 to 4 carbon atoms, the C-6 and C-5 hydrogen atoms are cis, in combination with a pharmaceutically acceptable carrier.

36. A method according to claim 35 wherein the compound is in the form of a pharmaceutically acceptable salt or in-vivo hydrolyzable ester.

37. A method according to claim 17 wherein $R^1$ is $OSO_3H$ or a pharmaceutically acceptable salt thereof or a methyl or ethyl ester thereof, [$OR^2$, $SR^3$, $OCOR^2$, $OCO_2R^3$] or $OCONHR^3$, wherein $R^3$ is alkyl of 1 to 4 carbon atoms, benzyl, phenyl or p-nitrobenzyl.

38. A method according to claim 35 wherein the compound is in the form of an ester, wherein the ester moiety is of the sub-formula (a), (b), (c) or (d):

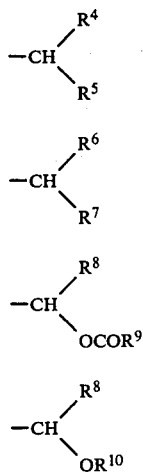

wherein $R^4$ is hydrogen, alkyl of up to 3 carbon atoms, alkenyl of up to 3 carbon atoms or alkynyl of up to 3 carbon atoms; $R^5$ is hydrogen or methyl; $R^6$ is unsubstituted or substituted by fluoro, chloro, bromo, nitro, methyl or methoxy; $R^7$ is hydrogen or phenyl unsubstituted or substituted by fluoro, chloro, bromo, nitro, methyl or methoxy; $R^8$ is hydrogen or methyl; $R^9$ is alkyl of 1 to 4 carbon atoms, phenyl or alkoxy of 1 to 4 carbon atoms; or $R^8$ is joined to $R^9$ to form a phthalidyl, dimethylphthalidyl or dimethoxyphthalidyl moiety; and $R^{10}$ is alkyl of 1 to 4 carbon atoms, phenyl, chlorophenyl, nitrophenyl or $CHR^4R^5$ is phenacyl or bromophenacyl.

39. A method according to claim 38 wherein $R^4$ is hydrogen, methyl, ethyl, vinyl or ethenyl; $R^5$ is hydrogen; $R^6$ is phenyl, p-bromophenyl, p-methoxyphenyl or p-nitrophenyl; $R^7$ is hydrogen; $R^9$ is methyl, t-butyl or ethoxy or is joined to $R^8$ to form a phthalidyl, dimethylphthalidyl or dimethoxyphthalidyl moiety; and $R^{10}$ is methyl.

40. A method according to claim 38 wherein the ester moiety is methyl or ethyl.

41. A method according to claim 38 wherein the ester moiety is benzyl or p-nitrobenzyl.

42. A method according to claim 38 wherein the ester moiety is acetoxymethyl, pivaloyloxymethyl, α-ethoxycarbonyloxymethyl or phthalidyl.

43. A method according to claim 38 wherein the ester moiety is methoxymethyl.

44. A method according to claim 38 wherein the ester moiety is p-nitrobenzyl or phthalidyl.

45. A method according to claim 35 wherein the compound is in the form or an alkali metal salt or alkaline earth metal salt.

46. A method according to claim 35 wherein the compound is in the form of the sodium or potassium salt.

47. A method according to claim 35 wherein $R^1$ is a pharmaceutically acceptable salt of $OSO_3H$ and the compound is in the form of a di-pharmaceutically acceptable salt.

48. A method according to claim 47 wherein the salt is in the form of the di-sodium or di-potassium salt.

49. A method according to claim 35 wherein the compound is

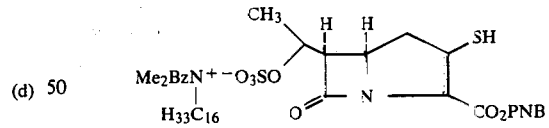

wherein PNB is p-nitrobenzyl.

* * * * *